(12) United States Patent
Rosenberg et al.

(10) Patent No.: US 8,822,196 B2
(45) Date of Patent: *Sep. 2, 2014

(54) ANTI-VASCULAR ENDOTHELIAL GROWTH FACTOR RECEPTOR-2 CHIMERIC ANTIGEN RECEPTORS AND USE OF SAME FOR THE TREATMENT OF CANCER

(71) Applicant: The United States of America, as represented by the Secretary, Department of Health and Human Services, Bethesda, MD (US)

(72) Inventors: Steven A. Rosenberg, Potomac, MD (US); Dhanalakshmi Chinnasamy, North Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/875,560

(22) Filed: May 2, 2013

(65) Prior Publication Data

US 2013/0225668 A1    Aug. 29, 2013

Related U.S. Application Data

(62) Division of application No. 13/499,349, filed as application No. PCT/US2010/048701 on Sep. 14, 2010, now Pat. No. 8,465,743.

(60) Provisional application No. 61/247,625, filed on Oct. 1, 2009.

(51) Int. Cl.
| C12N 15/62 | (2006.01) |
| C07K 14/705 | (2006.01) |
| C07K 16/28 | (2006.01) |
| C12N 15/63 | (2006.01) |
| C12N 15/79 | (2006.01) |

(52) U.S. Cl.
USPC ....... 435/252.3; 435/7.23; 435/326; 435/334; 536/23.4

(58) Field of Classification Search
None
See application file for complete search history.

(56) References Cited

U.S. PATENT DOCUMENTS

| 3,832,253 A | 8/1974 | Di Palma et al. |
| 3,854,480 A | 12/1974 | Zaffaroni |
| 4,235,871 A | 11/1980 | Papahadjopoulos et al. |
| 4,450,150 A | 5/1984 | Sidman |
| 4,452,775 A | 6/1984 | Kent |
| 4,501,728 A | 2/1985 | Geho et al. |
| 4,667,014 A | 5/1987 | Nestor, Jr. et al. |
| 4,748,034 A | 5/1988 | de Rham |
| 4,837,028 A | 6/1989 | Allen |
| 5,019,369 A | 5/1991 | Presant et al. |
| 5,075,109 A | 12/1991 | Tice et al. |
| 5,087,616 A | 2/1992 | Myers et al. |
| 5,225,539 A | 7/1993 | Winter |
| 5,239,660 A | 8/1993 | Ooi |
| 5,449,752 A | 9/1995 | Fujii et al. |
| 5,540,926 A | 7/1996 | Aruflo et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,693,761 A | 12/1997 | Queen et al. |
| 5,714,352 A | 2/1998 | Jakobovits |
| 5,840,301 A | 11/1998 | Rockwell et al. |
| 5,861,499 A | 1/1999 | Rockwell et al. |
| 6,265,150 B1 | 7/2001 | Terstappen et al. |
| 7,446,190 B2 | 11/2008 | Sadelain et al. |
| 7,498,414 B2 | 3/2009 | Zhu |
| 8,465,743 B2 * | 6/2013 | Rosenberg et al. ........ 424/134.1 |
| 2002/0197266 A1 | 12/2002 | Debinski |
| 2003/0036506 A1 | 2/2003 | Kranz et al. |
| 2004/0242851 A1 | 12/2004 | Zhu |
| 2005/0234225 A1 | 10/2005 | Zhu |
| 2006/0269529 A1 | 11/2006 | Niederman et al. |
| 2009/0142358 A1 | 6/2009 | Zhu |
| 2010/0105136 A1 | 4/2010 | Carter et al. |
| 2012/0213783 A1* | 8/2012 | Rosenberg et al. ........ 424/134.1 |

FOREIGN PATENT DOCUMENTS

| EP | 0 239 400 B1 | 8/1994 |
| GB | 2 188 638 A | 10/1987 |
| WO | WO 2007/095337 A2 | 8/2007 |
| WO | WO 2008/045437 A2 | 4/2008 |
| WO | WO 2008/095141 A2 | 8/2008 |

OTHER PUBLICATIONS

Abstracts presented in iSBTc 24th Annual Meeting, Oct. 29-31, 2009.

Capecchi, "High efficiency transformation by direct microinjection of DNA into cultured mammalian cells," *Cell*, 22 (Part 2), 479-488 (1980).

(Continued)

*Primary Examiner* — Phuong Huynh
(74) *Attorney, Agent, or Firm* — Leydig, Voit & Mayer, Ltd.

(57) ABSTRACT

The invention provides chimeric antigen receptors (CARs) comprising an antigen binding domain of a KDR-1121 or DC101 antibody, an extracellular hinge domain, a T cell receptor transmembrane domain, and an intracellular domain T cell receptor signaling domain. Nucleic acids, recombinant expression vectors, host cells, populations of cells, antibodies, or antigen binding portions thereof, and pharmaceutical compositions relating to the CARs are disclosed. Methods of detecting the presence of cancer in a host and methods of treating or preventing cancer in a host are also disclosed.

19 Claims, 19 Drawing Sheets

(56) References Cited

OTHER PUBLICATIONS

Carpenito et al., "Control of large, established tumor xenografts with genetically retargeted human T cells containing CD28 and CD137 domains," *PNAS*, 106 (9), 3360-3365 (2009).
Chinnasamy et al., "Gene therapy using genetically modified lymphocytes targeting VEGFR-2 inhibits the growth of vascularized syngenic tumors in mice," *J. Clin. Invest.*, 120 (11), 1-16 (2010).
Chu et al., "SV40 DNA transfection of cells in suspension: analysis of efficiency of transcription and translation of T-antigen," *Gene*, 13 (2), 197-202 (1981).
Clarkson et al., "T-Cell Costimulatory Pathways in Allograft Rejection and Tolerance," *Transplantation*, 80(5), 555-563 (2005).
Clay et al., "Efficient transfer of a tumor antigen-reactive TCR to human peripheral blood lymphocytes confers anti-tumor reactivity," *J. Immunol.*, 163 (1), 507-513 (1999).
Dias et al., "Autocrine stimulation of VEGFR-2 activates human leukemic cell growth and migration," *J. Clin. Invest.*, 106 (4), 511-521 (2000).
Felgner et al., "Lipofection: A highly efficient, lipid-mediated DNA-transfection procedure," *Proc. Natl. Acad. Sci. USA*, 84 (21), 7413-7417 (1987).
Ferrara et al., "The biology of VEGF and its receptors," *Nat. Med.*, 9 (6), 669-676 (2003).
Finney et al., "Activation of resting human primary T cells with chimeric receptors: costimulation from CD28, inducible costimulator, CD134, and CD137 in series with signals from the TCRζ chain," *J. Immunol.*, 172 (1), 104-113 (2004).
Friedmann-Morvinski et al., "Redirected primary T cells harboring a chimeric receptor require costimulation for their antigen-specific activation," *Blood*, 105 (8), 3087-3093 (2005).
Gao et al., "UpGene: Application of a web-based DNA codon optimization algorithm," *Biotechnol. Prog.*, 20 (2), 443-448 (2004).
GenBank Accession No. J04492, Apr. 27, 1993.
Genbank Accession No. NM_007642, Mar. 25, 2012.
GenBank Accession No. NM_001113391, Mar. 7, 2012.
Graham et al., "A new technique for the assay of infectivity of human adenovirus 5 DNA," *Virology*, 52 (2), 456-467 (1973).
Gross et al., "Expression of immunoglobulin-T-cell receptor chimeric molecules as functional receptors with antibody-type specificity," *Proc. Natl. Acad. Sci. USA*, 86 (24), 10024-10028 (1989).
Hanenberg at al., "Colocalization of retrovirus and target cells on specific fibronectin fragments increases genetic transduction of mammalian cells," *Nat. Med.*, 2 (8), 876-882 (1996).
Haskard et al., "The production of human monoclonal autoantibodies from patients with rheumatoid arthritis by the EBV-hybridoma technique," *J. Immunol. Methods*, 74 (2), 361-367 (1984).
Hudecz, "Synthesis of peptide bioconjugates," *Methods Mol. Biol.*, 298, 209-223 (2005).
Hughes et al., "Transfer of a TCR gene derived from a patient with a marked antitumor response conveys highly active T-cell effector functions," *Hum. Gene Ther.*, 16 (4), 457-472 (2005).
Huse et al., "Generation of a large combinatorial library of the immunoglobulin repertoire in phage lambda," *Science*, 246, 1275-1281 (1989).
Inoue et al., "Treatment of human metastatic transitional cell carcinoma of the bladder in a murine model with the anti-vascular endothelial growth factor receptor monoclonal antibody DC101 and paclitaxel," *Clin. Cancer Research*, 6 (7), 2635-2643 (2000).
International Search Report, Application No. PCT/US2010/048701, dated Sep. 11, 2010.
Jain, "Normalization of tumor vasculature: an emerging concept in antiangiogenic therapy," *Science*, 307, 58-62 (2005).
Kershaw et al., "Generation of gene-modified T cells reactive against the angiogenic kinase insert domain-containing receptor (KDR) found on tumor vasculature," *Hum. Gene Ther.*, 11 (18), 2445-2452 (2000).
Kershaw et al., "Supernatural T cells: genetic modification of T cells for cancer therapy," *Nat. Rev. Immunol.*, 5 (12), 928-940 (2005).
Kirin et al., "Amino acid and peptide bioconjugates of copper(II) and zinc(II) complexes with a modified N,N-bis(2-picolyl)amine ligand," *Inorg. Chem.*, 44 (15), 5405-5415 (2005).
Klein et al., "High-velocity microprojectiles for delivering nucleic acids into living cells," *Nature*, 327, 70-73 (1987).
Köhler et al., "Derivation of specific antibody-producing tissue culture and tumor lines by cell fusion," *Eur. J. Immunol.*, 6 (7), 511-519 (1976).
Kroczek et al., "T-cell costimulatory molecules: Optimal targets for the treatment of allergic airway disease with monoclonal antibodies," *J. Allergy Clin. Immunol.*, 116(4), 906-909 (2005).
Li et al., "Lentiviral rescue of vascular endothelial growth factor receptor-2 expression in Flk1-/- embryonic stem cells shows early priming of endothelial precursors," *Stem Cells*, 25 (12), 2987-2995 (2007).
Lu et al., "Identification of the residues in the extracellular region of KDR important for interaction with vascular endothelial growth factor and neutralizing anti-KDR antibodies," *J. Biol. Chem.*, 275 (19), 14321-14330 (2000).
Lu et al., "Tailoring in vitro selection for a picomolar affinity human antibody directed against vascular endothelial growth factor receptor 2 for enhanced neutralizing activity," *J. Biol. Chem.*, 278 (44), 43496-43507 (2003).
Maher et al., "Human T-lymphocyte cytotoxicity and proliferation directed by a single chimeric TCRζ/CD28 receptor," *Nat. Biotechnol.*, 20 (1), 70-75 (2002).
Mannino et al., "Liposome mediated gene transfer," *BioTechniques*, 6 (7), 682-690 (1988).
Niederman et al., "Antitumor activity of cytotoxic T lymphocytes engineered to target vascular endothelial growth factor receptors," *PNAS*, 99 (10), 7009-7014 (2002).
Onodera et al., "A simple and reliable method for screening retroviral producer clones without selectable markers," *Hum. Gene Ther.*, 8 (10), 1189-1194 (1997).
Pedersen et al., "Comparison of surface accessible residues in human and murine immunoglobulin Fv domains. Implication for humanization of murine antibodies," *J. Mol. Biol.*, 235 (3), 959-973 (1994).
Porter et al., "Comparison of efficiency of infection of human gene therapy target cells via four different retroviral receptors," *Hum. Gene Ther.*, 7 (8), 913-919 (1996).
Prewett et al., "Antivascular endothelial growth factor receptor (fetal liver kinase 1) monoclonal antibody inhibits tumor angiogenesis and growth of several mouse and human tumors," *Cancer Research*, 59, 5209-5218 (1999).
Reiter et al., "Engineering interchain disulfide bonds into conserved framework regions of Fv fragments: improved biochemical characteristics of recombinant immunotoxins containing disulfide-stabilized Fv," *Protein Eng.*, 7 (5), 697-704 (1994).
Roder et al., "The EBV-hybridoma technique," *Methods Enzymol.*, 121, 140-167 (1986).
Shigekawa et al., "Electroporation of eukaryotes and prokaryotes: a general approach to the introduction of macromolecules into cells," *BioTechniques*, 6 (8), 742-751 (1988).
Szoka et al., "Comparative properties and methods of preparation of lipid vesicles (liposomes)," *Ann. Rev. Biophys. Bioeng.*, 9, 467-508 (1980).
Tong et al., "Vascular normalization by vascular endothelial growth factor receptor 2 blockade induces a pressure gradient across the vasculature and improves drug penetration in tumors," *Cancer Res.*, 64 (11), 3731-3736 (2004).
Wadhwa et al., "Receptor mediated glycotargeting," *J. Drug Target.*, 3 (2), 111-127 (1995).
Wang et al., "Optimizing adoptive polyclonal T cell immunotherapy of lymphomas, using a chimeric T cell receptor possessing CD28 and CD137 costimulatory domains," *Hum. Gene Ther.*, 18 (8), 712-725 (2007).
Witte et al., "Monoclonal antibodies targeting the VEGF receptor-2 (Flk1/KDR) as an anti-angiogenic therapeutic strategy," *Cancer and Metastasis Reviews*, 17, 155-161 (1998).

(56) References Cited

OTHER PUBLICATIONS

Zhao et al., "Primary human lymphocytes transduced with NY-ESO-1 antigen-specific TCR genes recognize and kill diverse human tumor cell lines," *J. Immunol.*, 174 (7), 4415-4423 (2005).

Zhao et. al., "A herceptin-based chimeric antigen receptor with modified signaling domains leads to enhanced survival of transduced T lymphocytes and antitumor activity," *J. Immunol.*, 183 (9), 5563-5574 (2009).

Zhu et al., "Inhibition of human leukemia in an animal model with human antibodies directed against vascular endothelial growth factor receptor 2. Correlation between antibody affinity and biological activity," *Leukemia*, 17 (3), 604-611 (2003).

* cited by examiner

US 8,822,196 B2

ANTI-VASCULAR ENDOTHELIAL GROWTH FACTOR RECEPTOR-2 CHIMERIC ANTIGEN RECEPTORS AND USE OF SAME FOR THE TREATMENT OF CANCER

CROSS-REFERENCE TO RELATED APPLICATIONS

This patent application is a Divisional of U.S. patent application Ser. No. 13/499,349, filed Apr. 23, 2012, now U.S. Pat. No. 8,465,743, which is the U.S. national phase of International Patent Application No. PCT/US2010/048701, filed Sep. 14, 2010, which claims the benefit of U.S. Provisional Patent Application No. 61/247,625, filed Oct. 1, 2009, each of which is incorporated by reference in its entirety herein.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 62,893 Byte ASCII (Text) file named "712636ST25.TXT," dated Apr. 12, 2013.

BACKGROUND OF THE INVENTION

Solid tumors account for more than 85% of cancer mortality (Jain, R. K. *Science* 307: 58-62 (2005)). The growth and metastasis of many cancers, e.g., solid tumors, is facilitated by the formation of new blood vessels, also known as angiogenesis. Accordingly, there is a need in the art for compositions and methods of treating or preventing cancer that target tumor angiogenesis.

BRIEF SUMMARY OF THE INVENTION

An embodiment of the invention provides chimeric antigen receptors (CARs) comprising an antigen binding domain of a KDR-1121 or DC101 antibody, an extracellular hinge domain, a T cell receptor transmembrane domain, and an intracellular T cell receptor signaling domain.

Further embodiments of the invention provide related nucleic acids, recombinant expression vectors, host cells, populations of cells, antibodies, or antigen binding portions thereof, and pharmaceutical compositions relating to the CARs of the invention.

Additional embodiments of the invention provide methods of detecting the presence of cancer in a host and methods of treating or preventing cancer in a host.

BRIEF DESCRIPTION OF THE SEVERAL VIEWS OF THE DRAWING(S)

Figure 3:
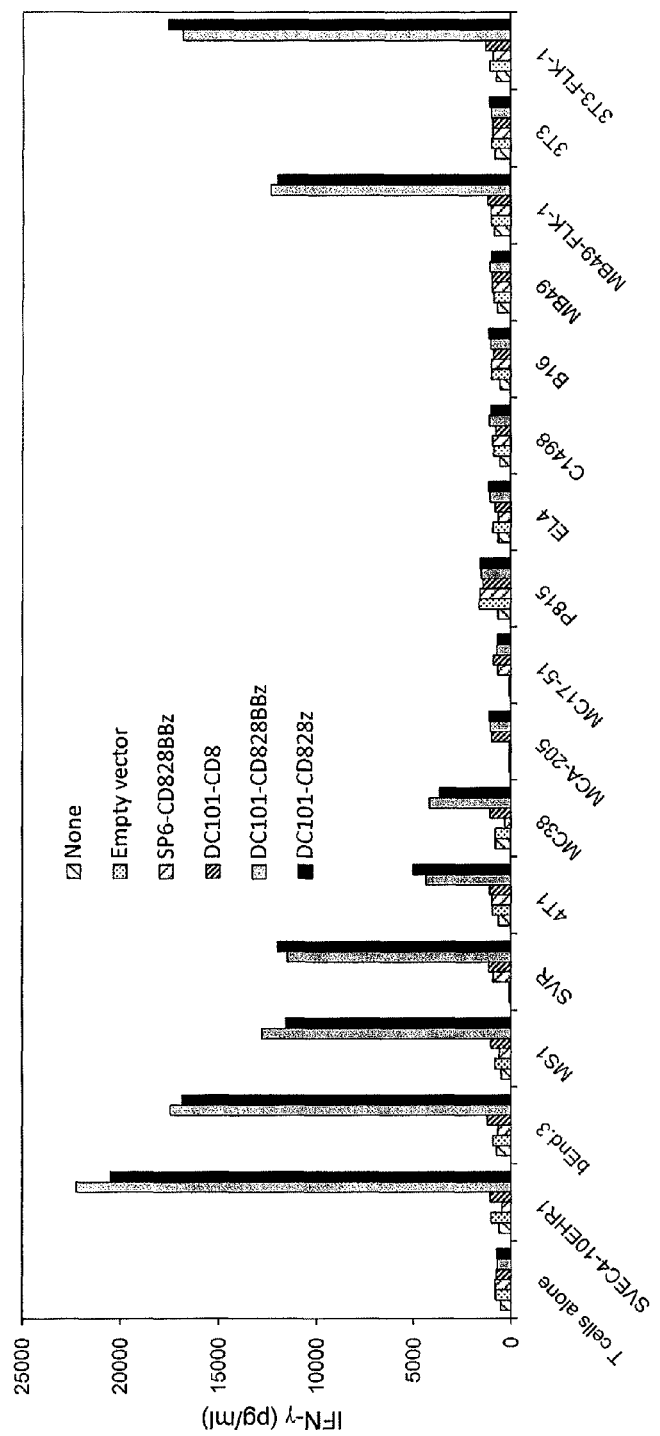

FIG. 3 is a graph of IFN-γ secretion (pg/ml) by cells untransduced (right slanting line) or transduced with an empty vector (dotted), SP6-CD828BBZ (left slanting line), DC101-CD8 (zebra stripe), DC101-CD828BBZ (grey), or DC101-CD828Z (black) when cultured alone or co-cultured with SVEC4-10EHR1, bEnd.3, MS1, SVR, 4T1, MC38, MCA-205, MC17-51, P815, EL4, C1498, B16, MB49, MB49-FLK-1, 3T3, or 3T3-FLK-1 cells.

Figure 4:
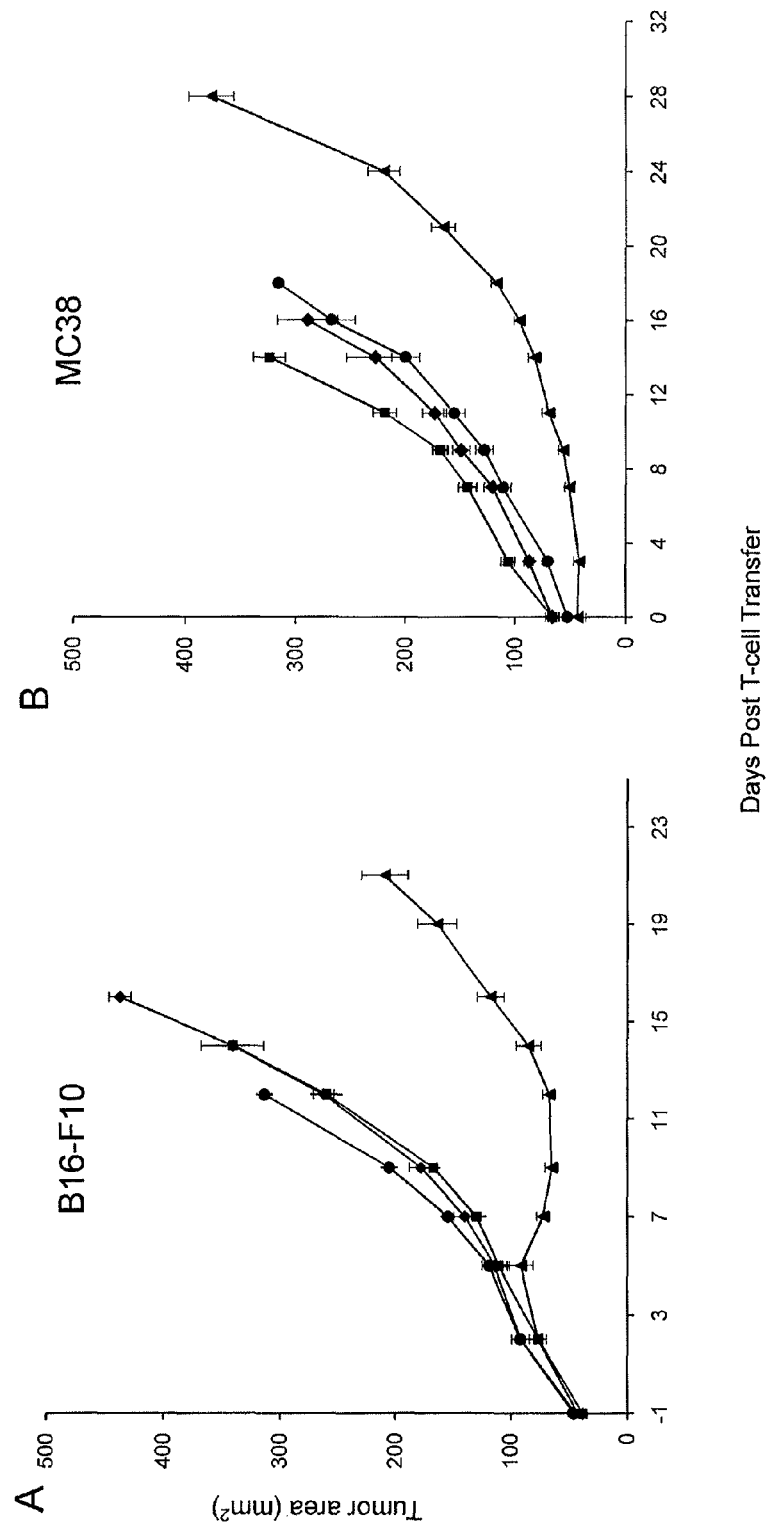

FIG. 4A is a graph of tumor area (mm$^2$) of mice bearing B16-F10 tumors that were untreated (closed circle), treated with rhIL-2 alone (closed diamond), or treated with T cells transduced with DC101 CAR (closed triangle), or empty vector (closed square), at days after T cell transfer.

FIG. 4B is a graph of tumor area (mm$^2$) of mice bearing MC38 tumors that were untreated (closed circle), treated with rhIL-2 alone (closed diamond), or treated with T cells transduced with DC101 CAR (closed triangle), or empty vector (closed square), at days after T cell transfer.

Figure 5:
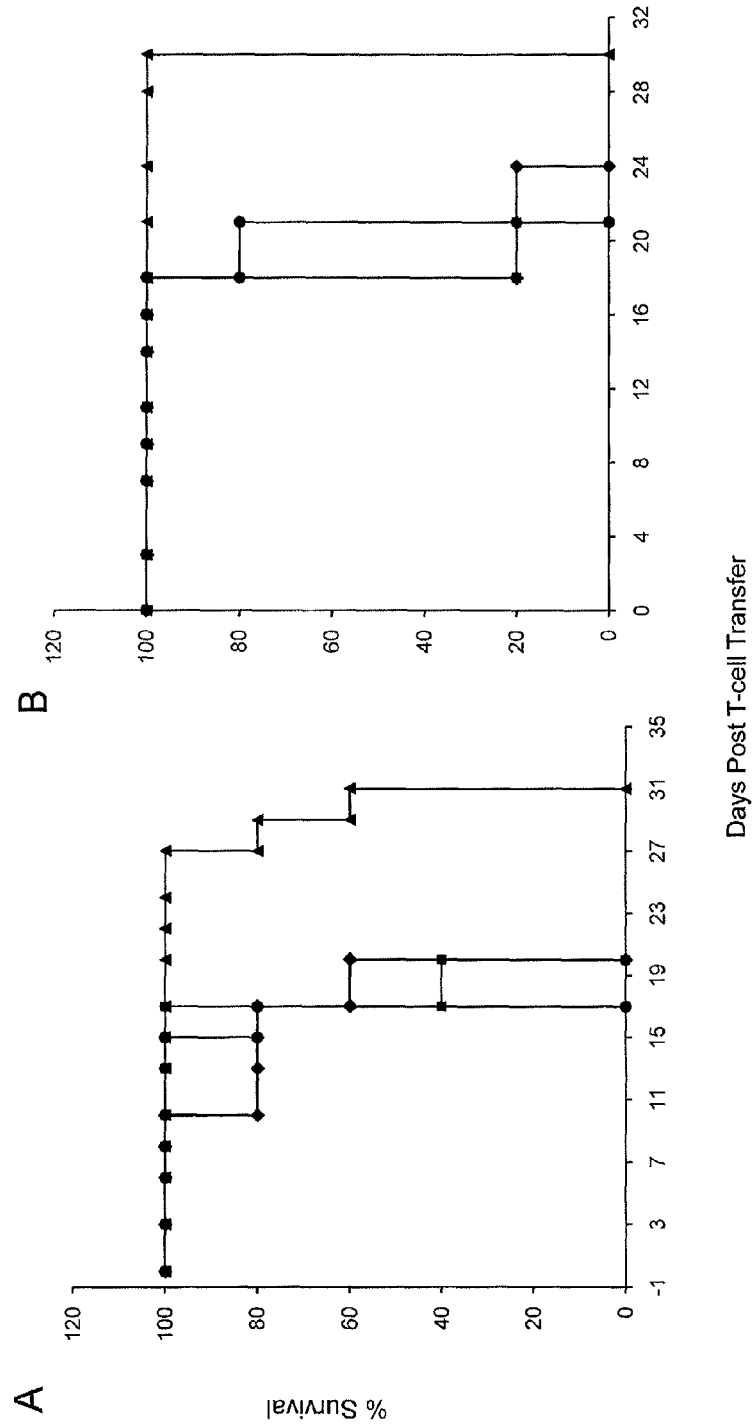

FIG. 5A is a graph of percent survival of mice bearing B16-F10 tumors that were untreated (closed circle), treated with rhIL-2 alone (closed diamond), or treated with T cells transduced with DC101 CAR (closed triangle), or empty vector (closed square), at days after T cell transfer.

FIG. 5B is a graph of percent survival of mice bearing MC38 tumors that were untreated (closed circle), treated with rhIL-2 alone (closed diamond), or treated with T cells transduced with DC101 CAR (closed triangle), or empty vector (closed square), at days after T cell transfer.

Figure 6:
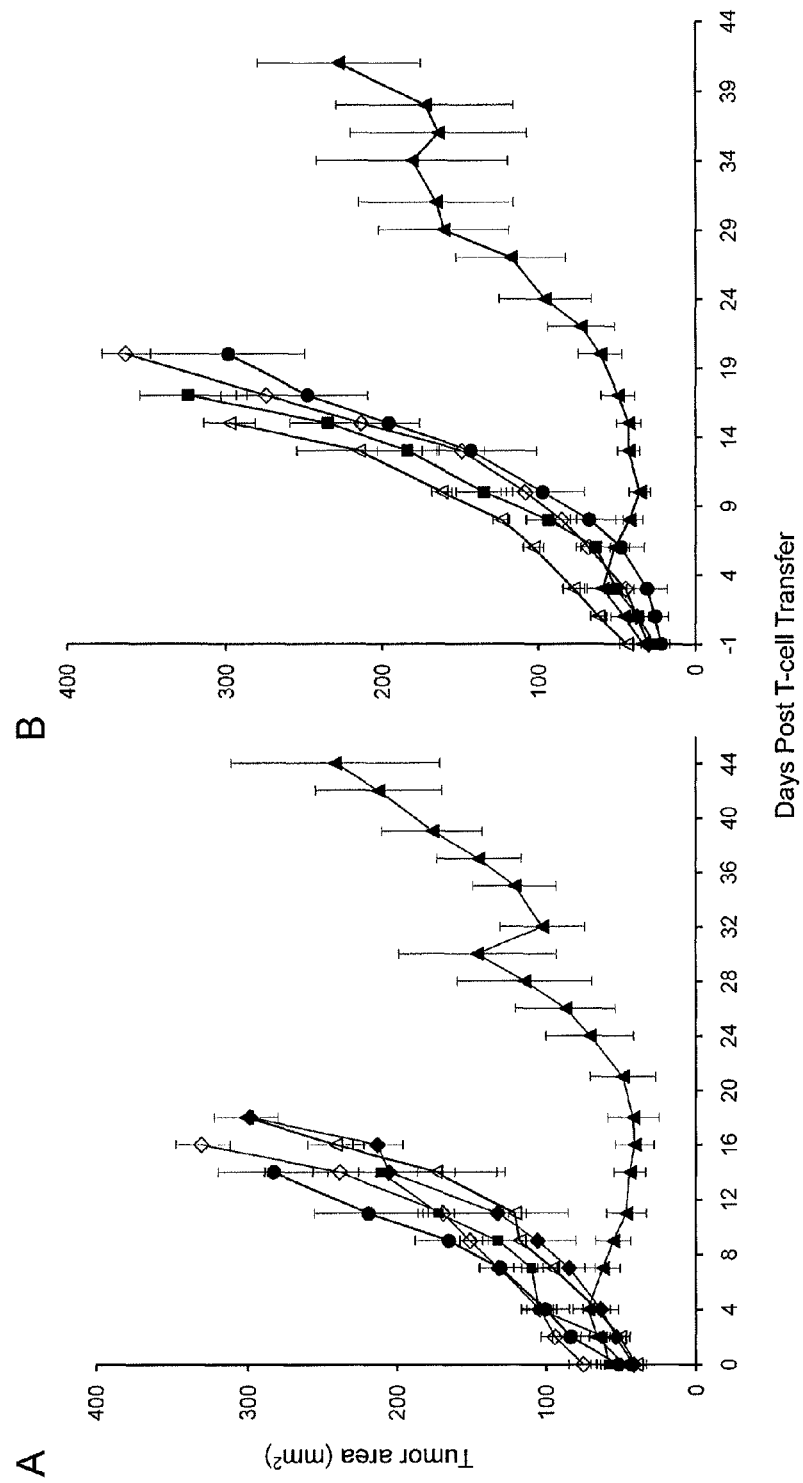

FIG. 6A is a graph of tumor area (mm$^2$) of mice bearing B16-F10 tumors that were untreated (closed circle), treated with rhIL-2 alone (closed diamond), treated with DC101 antibody (open triangle), treated with rat IgG1 antibody (open diamond), or treated with T cells transduced with DC101 CAR (closed triangle), or empty vector (closed square), at days after T cell transfer.

FIG. 6B is a graph of tumor area (mm$^2$) of mice bearing B16-F10 tumors that were untreated (closed circle), or treated with T cells transduced with DC101-CD828BBZ CAR vector (closed triangle), SP6-CD8S8BBZ CAR vector (open diamond), DC101-CD8 vector (open triangle), or an empty vector (closed square), at days after T cell transfer.

Figure 7:
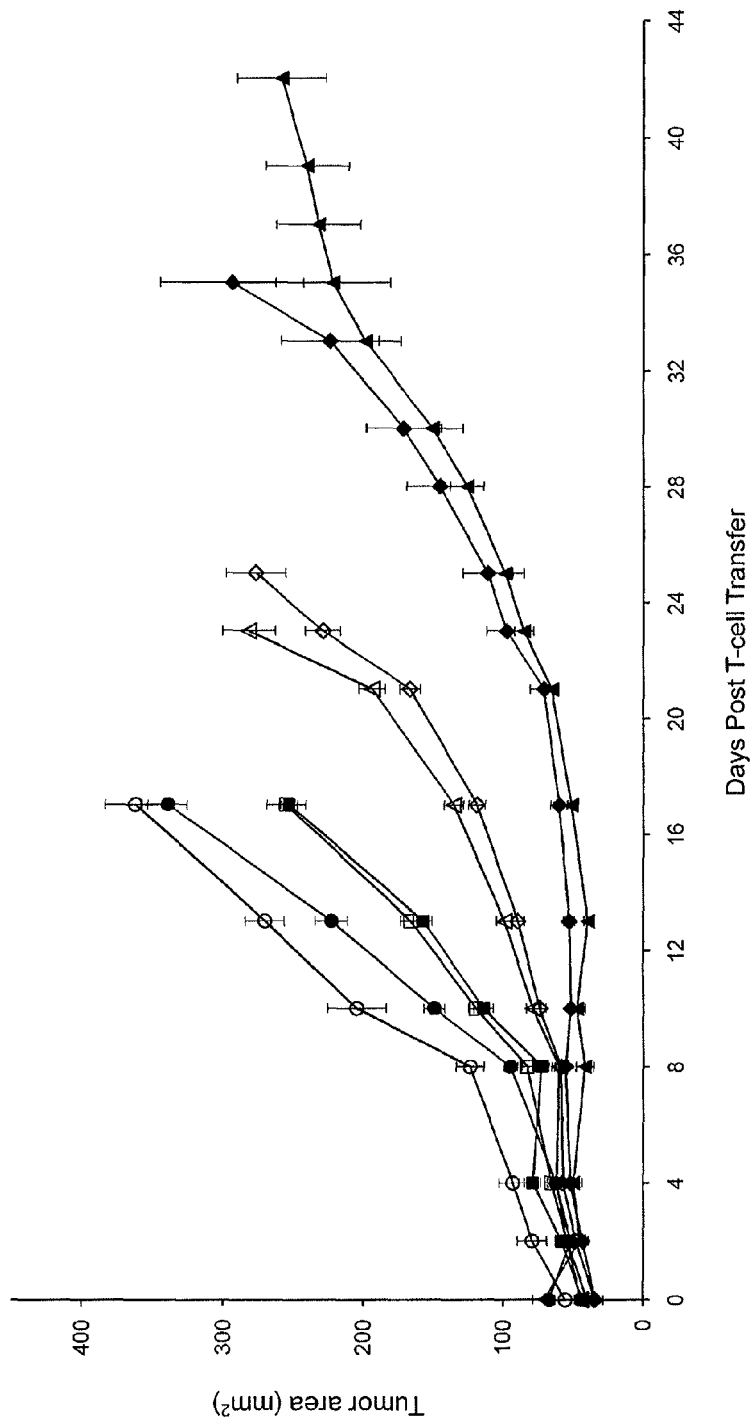

FIG. 7 is a graph of tumor area (mm$^2$) of mice bearing B16-F10 tumors that were treated with T cells transduced with DC101-mCD828BBZ (diamond), DC101-CD828Z (triangle), or an empty vector (square), at days after T cell transfer. Control groups received no T cell therapy (circle). Closed symbols indicate exogenous rhIL-2 administration and open symbols indicate no rhIL-2 administration.

Figure 8:
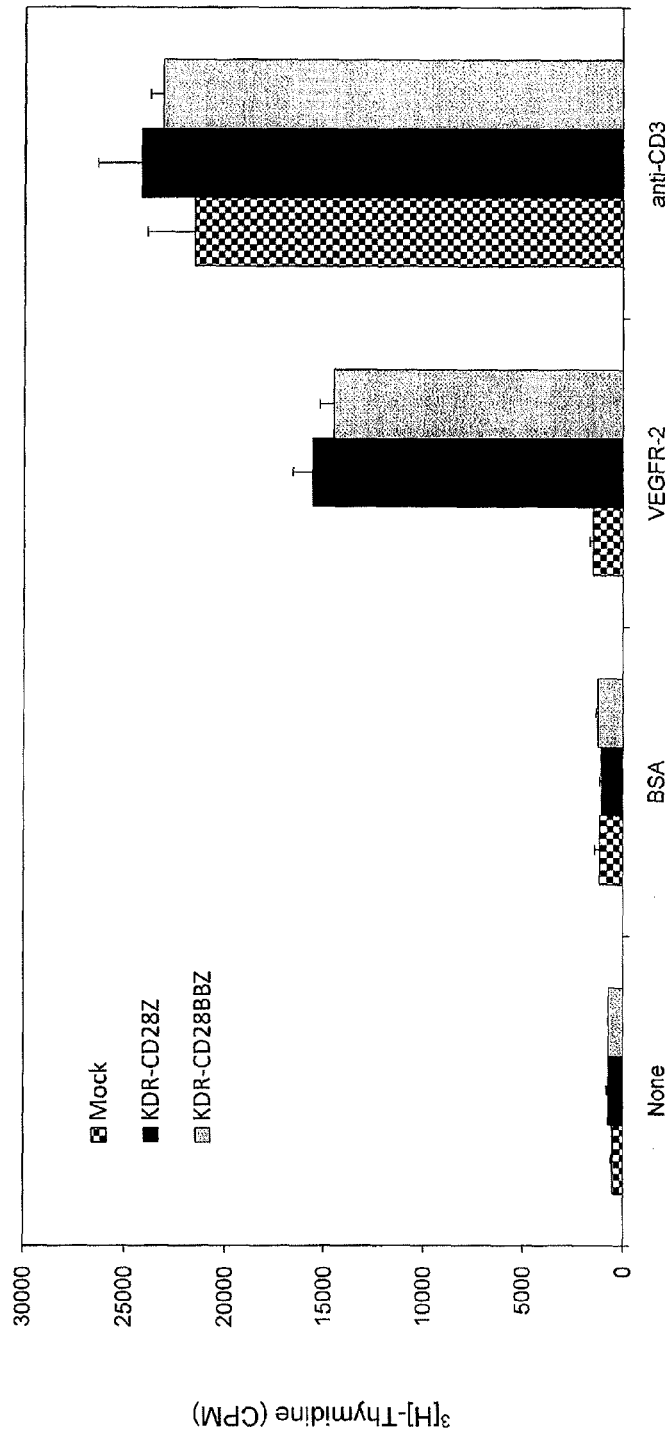

FIG. 8 is a graph of incorporation of $^3$[H]-thymidine (CPM) by cells mock transduced (checkered), or transduced with KDR-CD28Z (black), or KDR-CD28BBZ (grey), as a measure of proliferation when cultured on plates bound with no antigen (none) or bound with BSA, VEGFR-2, or anti-CD3.

Figure 9:
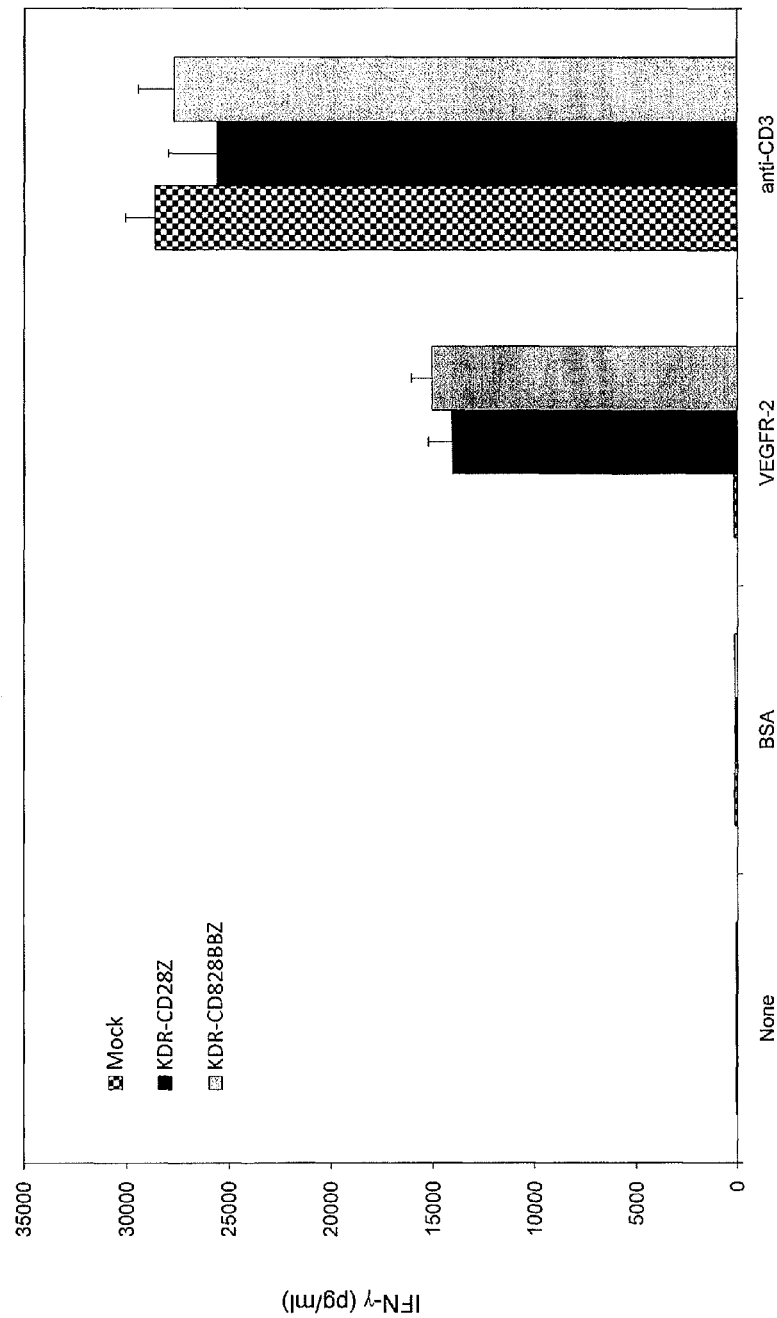

FIG. 9 is a graph of IFN-γ secretion (pg/ml) by cells mock transduced (checkered), or transduced with KDR-CD28Z (black), or KDR-CD28BBZ (grey), when cultured on plates bound with no antigen (none) or bound with BSA, VEGFR-2, or anti-CD3.

Figure 10:
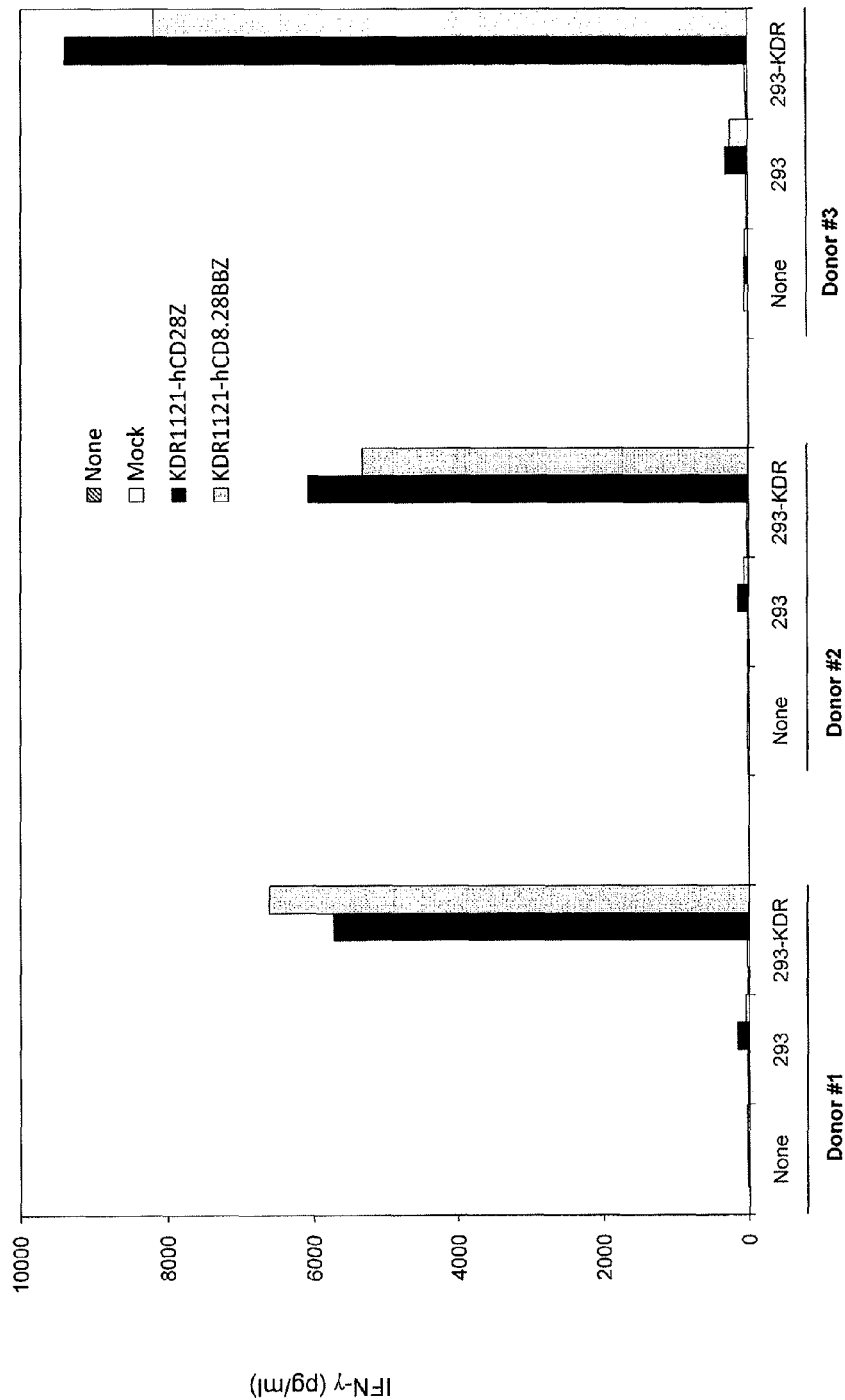

FIG. 10 is a graph of IFN-γ secretion (pg/ml) by cells untransduced (dark grey), mock transduced (white), or transduced with KDR1121-hCD28Z (black), or KDR1121-hCD828BBZ (light grey) when cultured alone (none) or co-cultured with 293 cells or 293-KDR cells for each of Donor Nos. 1-3.

Figure 11:
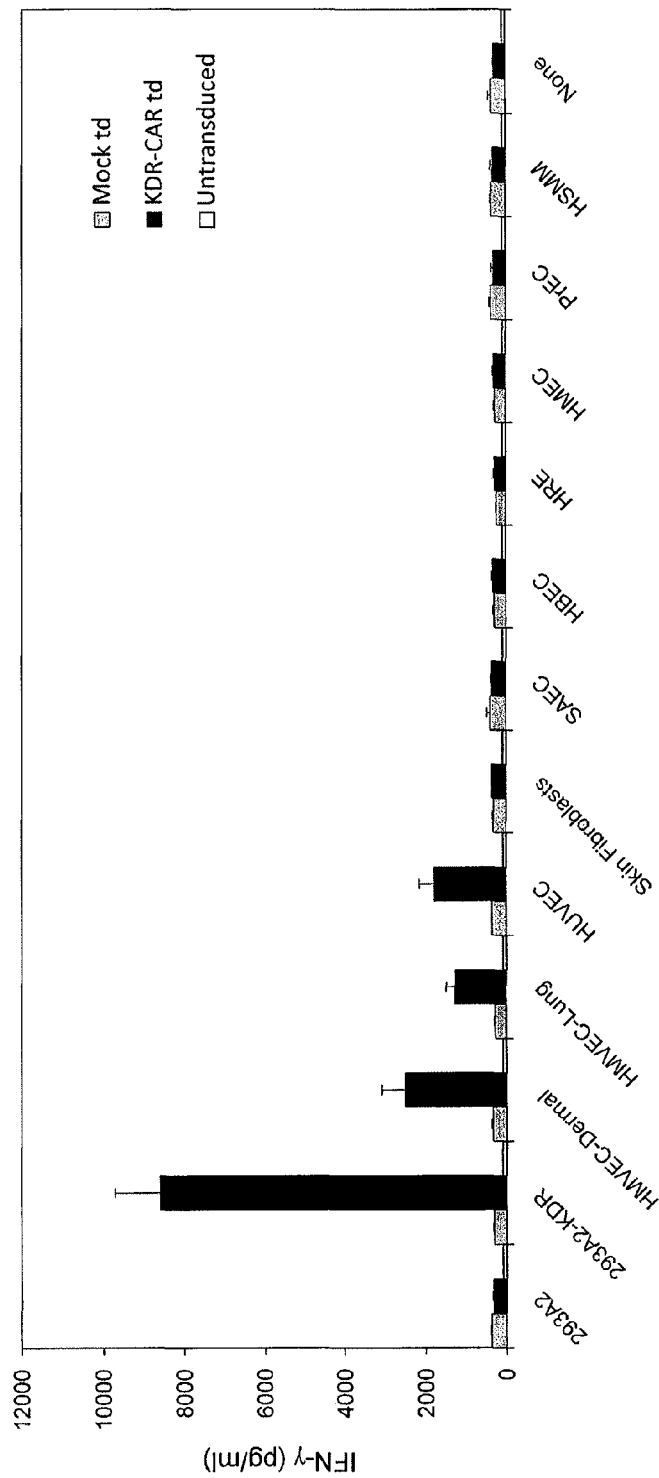

FIG. 11 is a graph of IFN-γ secretion (pg/ml) by T cells untransduced (white), mock transduced (grey), or transduced with KDR-CD28Z (black) when cultured alone (none) or co-cultured with target cells 293A2, 293A2-KDR, HMVEC-Dermal, HMVEC-Lung, HUVEC, skin fibroblasts, SAEC, HBEC, HRE, HMEC, PrEC, or HSMM cells.

Figure 12:
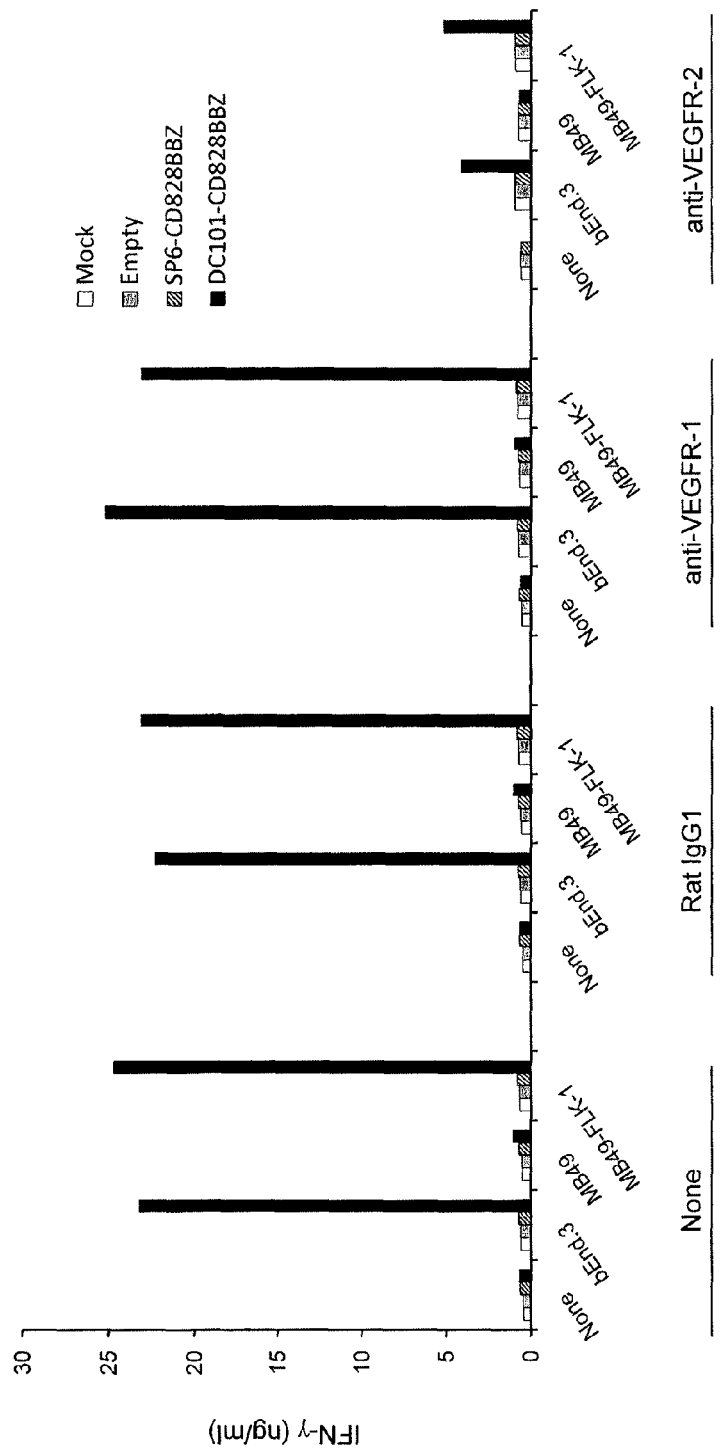

FIG. 12 is a graph of IFN-γ secretion (ng/ml) upon incubation of no cells (none) or target cells (bEnd.3, MB49, or MB49-FLK-1) alone (underlined none) or with 10 μg/ml of rat IgG1, anti-mouse VEGFR-1 antibody, or anti-mouse VEGFR-2 antibody (DC101) and then coculture with primary mouse T cells mock-transduced (white bars) or transduced with an empty vector (grey bars) or a retroviral vector encoding SP6-CD828BBZ CAR (hatched bars), or DC101-CD828BBZ (black bars).

Figure 13:
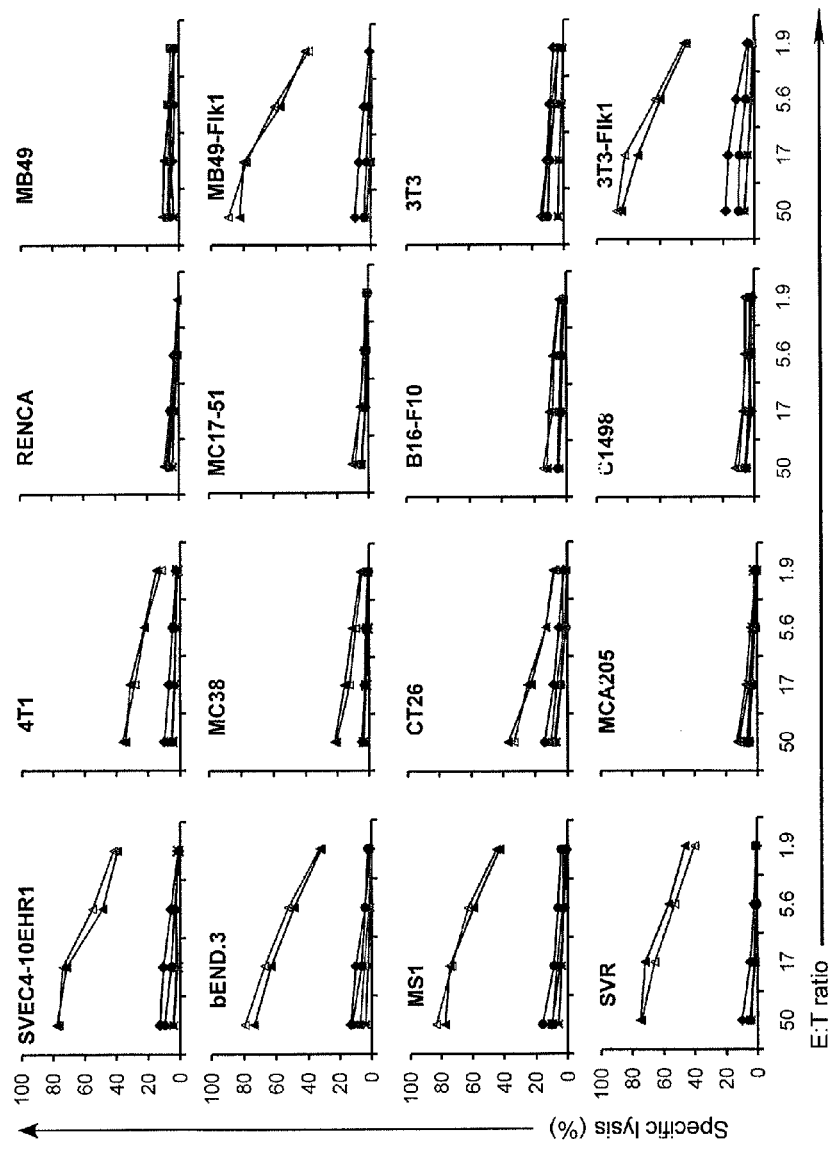

FIG. 13 shows graphs of specific lysis (%) (y axis) of target mouse cells (SVEC4-10EHR1, 4T1, RENCA, MB49, bEND.3, MC38, MC17-51, MB49-Flk1, MS1, CT26, B16-F10, 3T3, SVR, MCA205, C1498, 3T3-Flk1) expressing VEGFR-2 incubated with primary mouse T cells mock transduced (*) or transduced with an empty vector (square), SP6-CD828BBZ (circle), DC101-CD8 (diamond), DC101-CD828Z (closed triangle) or DC101-CD828BBZ (open triangle) at varying effector-to-target ratios (x axis). Each data point reflects the mean of triplicates.

Figure 14:
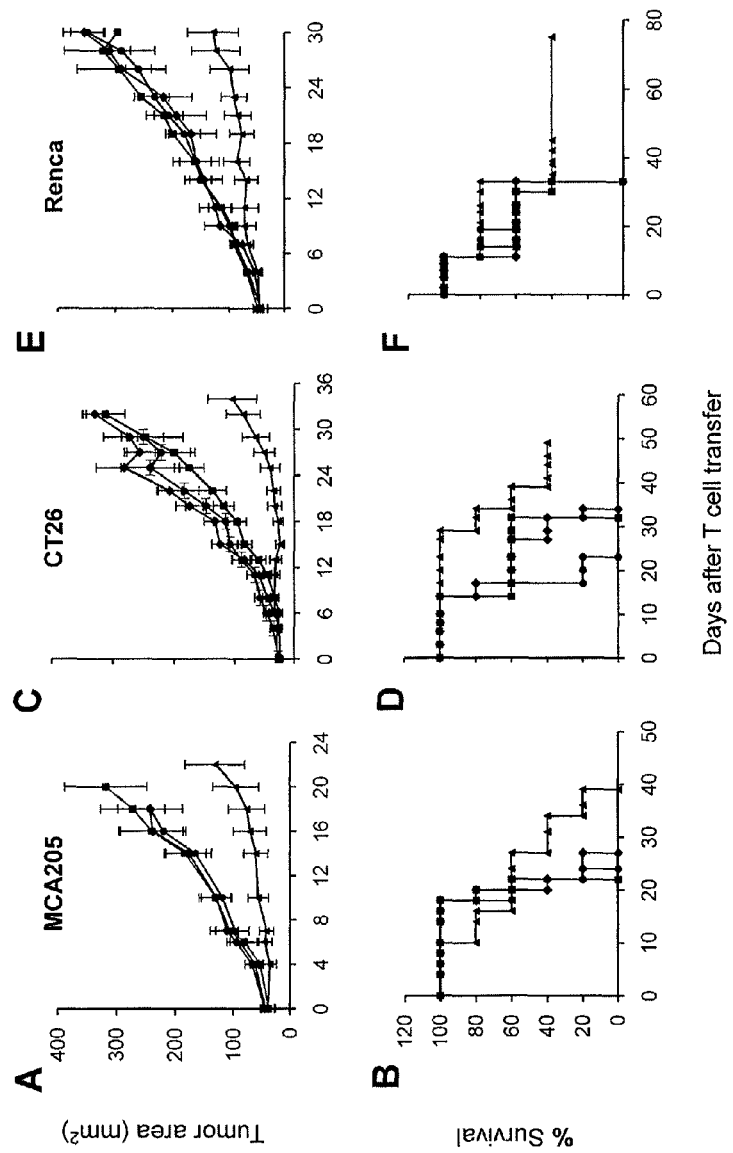

FIG. 14A is a graph of tumor area ($mm^2$) of mice bearing MCA205 tumors that were untreated (closed circle), treated with rhIL-2 alone (closed diamond), or treated with T cells transduced with DC101-CD828BBZ CAR (closed triangle), or empty vector (closed square), at days after T cell transfer.

FIG. 14B is a graph of percent survival of mice bearing MCA205 tumors that were untreated (closed circle), treated with rhIL-2 alone (closed diamond), or treated with T cells transduced with DC101-CD828BBZ CAR (closed triangle), or empty vector (closed square), at days after T cell transfer.

FIG. 14C is a graph of tumor area ($mm^2$) of mice bearing CT26 tumors that were untreated (closed circle), treated with rhIL-2 alone (closed diamond), or treated with T cells transduced with DC101-CD828BBZ CAR (closed triangle), or empty vector (closed square), at days after T cell transfer.

FIG. 14D is a graph of percent survival of mice bearing CT26 tumors that were untreated (closed circle), treated with rhIL-2 alone (closed diamond), or treated with T cells transduced with DC101-CD828BBZ CAR (closed triangle), or empty vector (closed square), at days after T cell transfer.

FIG. 14E is a graph of tumor area ($mm^2$) of mice bearing RENCA tumors that were untreated (closed circle), treated with rhIL-2 alone (closed diamond), or treated with T cells transduced with DC101-CD828BBZ CAR (closed triangle), or empty vector (closed square), at days after T cell transfer.

FIG. 14F is a graph of percent survival of mice bearing RENCA tumors that were untreated (closed circle), treated with rhIL-2 alone (closed diamond), or treated with T cells transduced with DC101-CD828BBZ CAR (closed triangle), or empty vector (closed square), at days after T cell transfer.

Figure 15:
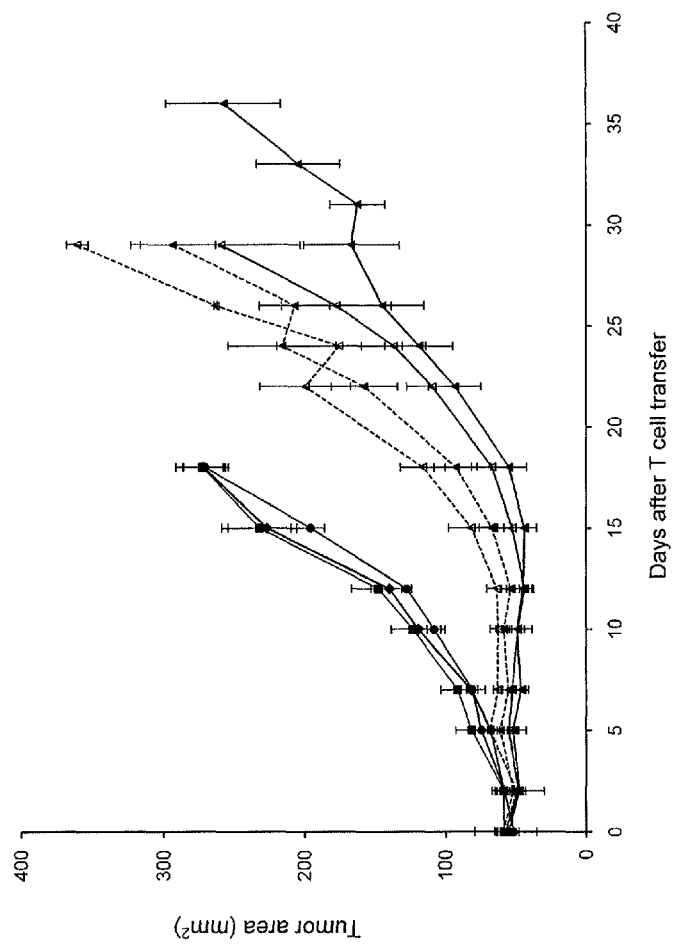

FIG. 15 is a graph of tumor area ($mm^2$) of mice bearing B16-F10 tumors that were treated with $2\times10^7$ (closed triangles on solid line), $1\times10^7$ (open triangles on solid line), $5\times10^6$ (closed triangles on dotted line), or $2\times10^6$ (open triangles on dotted line) syngeneic T cells transduced with DC101-CD828BBZ plus rhIL-2, untreated (closed circle), treated with rhIL-2 alone (closed diamond), or treated with $2\times10^7$ T cells transduced with an empty vector plus rhIL-2 (closed square), at days after T cell transfer. Each treatment group included a minimum of 5 mice. Serial, blinded tumor measurements were obtained and the products of perpendicular diameters were plotted ±SEM.

Figure 16:
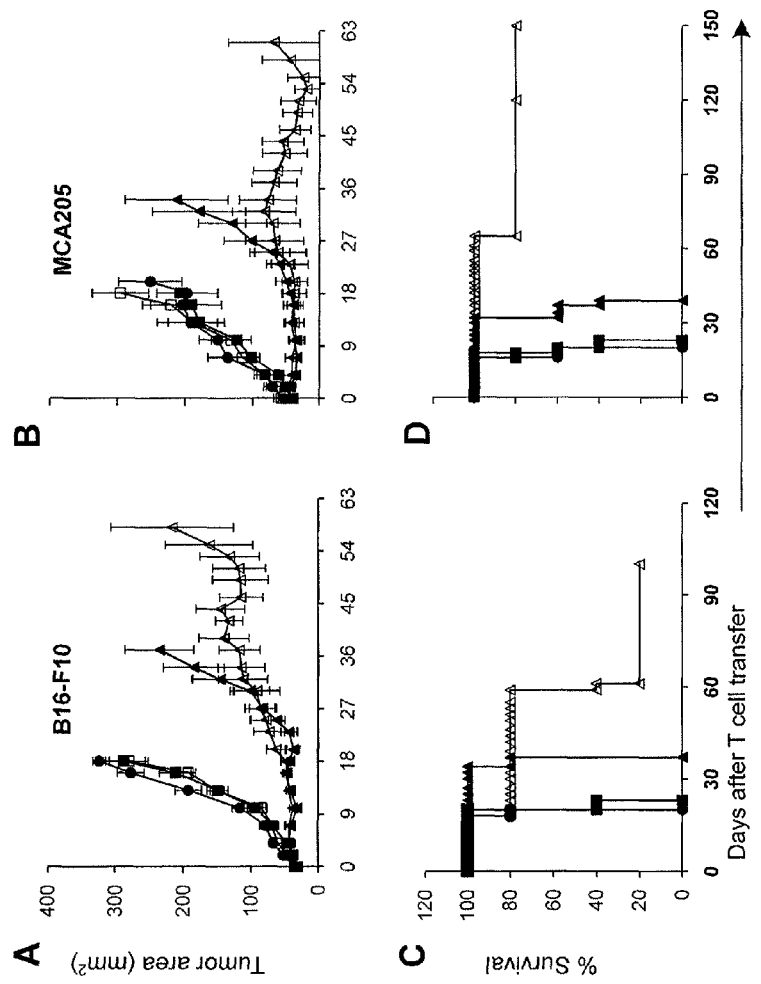

FIG. 16A is a graph of tumor area ($mm^2$) of mice bearing subcutaneous B16-F10 tumors sublethally irradiated at 5Gy TBI and which received no T cells or rhIL-2 (closed circles) or which were injected with a single dose of $2\times10^7$ DC101-CD28BBZ (closed triangles) or empty vector (closed squares) transduced syngeneic mouse T cells in conjunction with rhIL-2; or 3 sequential doses of $5\times10^6$ DC101-CAR (open triangles) or empty vector (open squares) transduced T cells at a 7 to 10 day interval and 2 daily doses of rhIL-2 for 3 days concomitant to cell transfer at 0-63 days after T cell transfer. Each treatment group included a minimum 5 mice. Serial, blinded tumor measurements were obtained and the products of perpendicular diameters were plotted ±SEM.

FIG. 16B is a graph of tumor area ($mm^2$) of mice bearing subcutaneous MCA205 tumors sublethally irradiated at 5Gy TBI and which received no T cells or rhIL-2 (closed circles) or which were injected with a single dose of $2\times10^7$ DC101-CD28BBZ (closed triangles) or empty vector (closed squares) transduced syngeneic mouse T cells in conjunction with rhIL-2; or 3 sequential doses of $5\times10^6$ DC101-CAR (open triangles) or empty vector (open squares) transduced T cells at a 7 to 10 day interval and 2 daily doses of rhIL-2 for 3 days concomitant to cell transfer at 0-63 days after T cell transfer. Each treatment group included a minimum of 5 mice. Serial, blinded tumor measurements were obtained and the products of perpendicular diameters were plotted ±SEM.

FIG. 16C is a graph of survival (%) of mice bearing subcutaneous B16-F10 tumors sublethally irradiated at 5Gy TBI and which received no T cells or rhIL-2 (closed circles) or which were injected with a single dose of $2\times10^7$ DC101-CD28BBZ (closed triangles) or empty vector (closed squares) transduced syngeneic mouse T cells in conjunction with rhIL-2; or 3 sequential doses of $5\times10^6$ DC101-CAR (open triangles) or empty vector (open squares) transduced T cells at a 7 to 10 day interval and 2 daily doses of rhIL-2 for 3 days concomitant to cell transfer at 0-120 days after T cell transfer. Each treatment group included a minimum of 5 mice. Serial, blinded tumor measurements were obtained and the products of perpendicular diameters were plotted ±SEM.

FIG. 16D is a graph of survival (%) of mice bearing subcutaneous MCA205 tumors sublethally irradiated at 5Gy TBI and which received no T cells or rhIL-2 (closed circles) or which were injected with a single dose of $2\times10^7$ DC101-CD28BBZ (closed triangles) or empty vector (closed squares) transduced syngeneic mouse T cells in conjunction with rhIL-2; or 3 sequential doses of $5\times10^6$ DC101-CAR (open triangles) or empty vector (open squares) transduced T cells at a 7 to 10 day interval and 2 daily doses of rhIL-2 for 3 days concomitant to cell transfer at 0-150 days after T cell transfer. Each treatment group included a minimum of 5 mice. Serial, blinded tumor measurements were obtained and the products of perpendicular diameters were plotted ±SEM.

Figure 17:
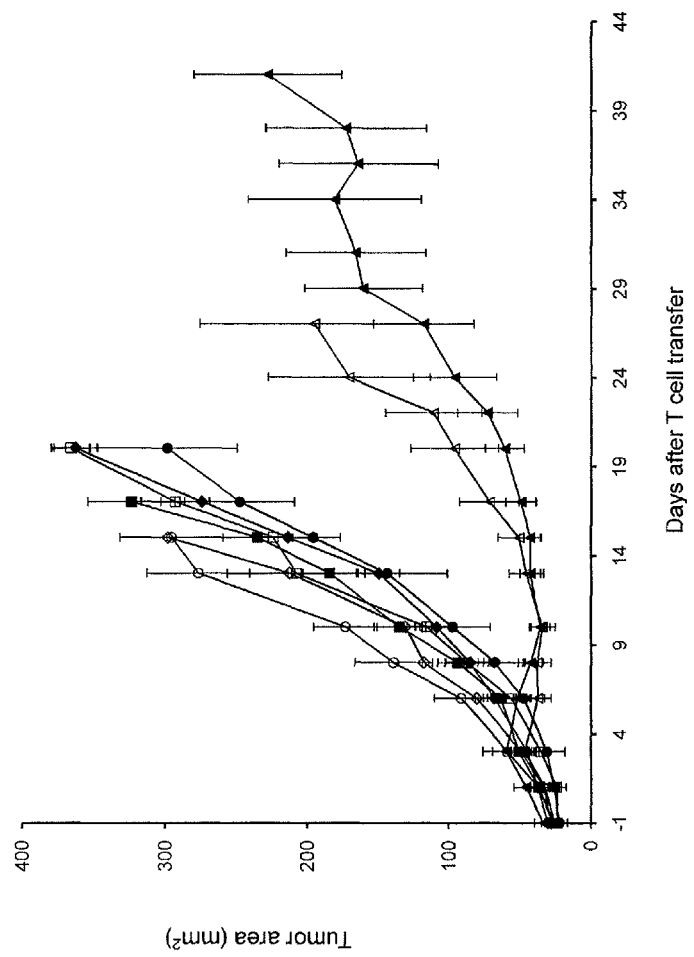

FIG. 17 is a graph of tumor area ($mm^2$) of mice bearing B16-F10 tumors that did not receive 5 Gy TBI prior to transfer of $2\times10^7$ syngeneic T cells transduced with DC101-CAR (open triangles), SP6-CAR (open diamonds), or an empty vector (open squares) plus rhIL-2, or not treated with T cells (open circles). Mice in groups represented in closed symbols received 5 Gy TBI prior to T cell transfer.

Figure 18:
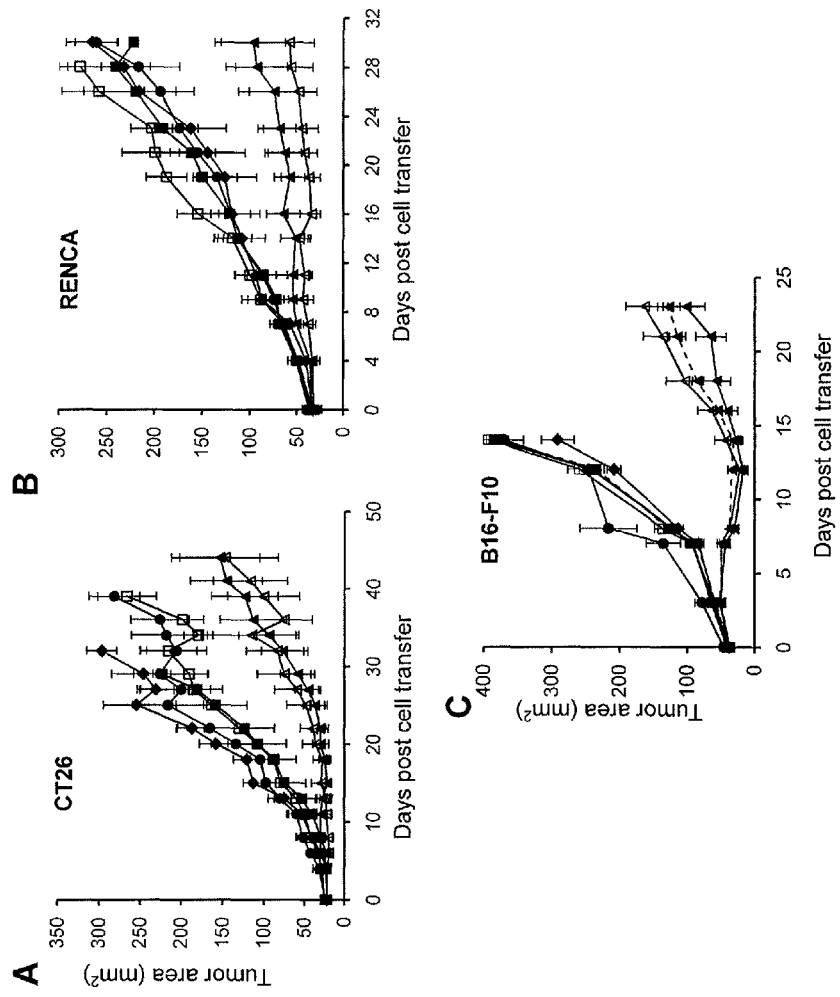

FIG. 18A is a graph of tumor area ($mm^2$) of BALB/c mice bearing CT26 tumors treated with a single dose of $5\times10^6$ unseparated $CD3^+$ T cells transduced with the DC101-CD828BBZ (closed triangles) or an empty vector (closed squares) or $2\times10^7$ purified $CD8^+$ T cells transduced with either DC101-CD828BBZ (open triangles) or an empty vector (open squares) at 0-50 days after T cell transfer. All T cell treatment groups received 2 daily doses of rhIL-2 for 3 days. Control groups received rhIL-2 alone (diamonds) or no treatment (circles).

FIG. 18B is a graph of tumor area (mm²) of BALB/c mice bearing RENCA tumors treated with a single dose of 5×10⁶ unseparated CD3⁺ T cells transduced with the DC101-CD828BBZ (closed triangles) or an empty vector (closed squares) or 2×10⁷ purified CD8⁺ T cells transduced with either DC101-CD828BBZ (open triangles) or an empty vector (open squares) at 0-32 days after T cell transfer. All T cell treatment groups received 2 daily doses of rhIL-2 for 3 days. Control groups received rhIL-2 alone (diamonds) or no treatment (circles).

FIG. 18C is a graph of tumor area (mm²) of C57BL/6 mice bearing B16-F10 tumors treated with a single dose of 2×10⁷ unseparated CD3⁺ T cells transduced with the DC101-CD828BBZ (closed triangles on solid line) or an empty vector (closed squares) or 2×10⁷ purified CD8⁺ T cells transduced with either DC101-CD828BBZ (open triangles on solid line) or an empty vector (open squares) at 0-25 days after T cell transfer. Some groups received a mixture of 1×10⁷ CD4⁺ T cells and 1×10⁷ CD8⁺ T cells transduced with DC101-CD828BBZ (closed triangles on dotted line) or an empty vector (open circles). All T cell treatment groups received 2 daily doses of rhIL-2 for 3 days. Control groups received rhIL-2 alone (closed diamonds) or no treatment (closed circles).

Figure 19:
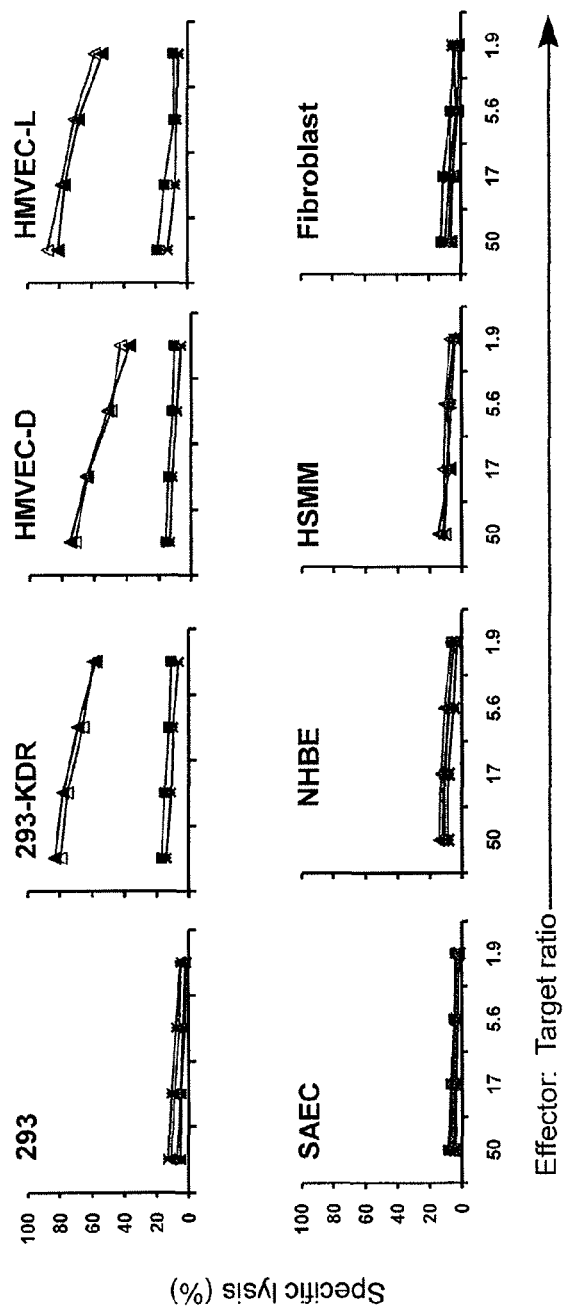

FIG. 19 shows graphs of specific lysis (%) (y axis) of target human cells (293, 293-KDR, HMVEC-D, HMVEC-L, SAEC, NHBE, HSMM, and Fibroblast) incubated with primary human T cells mock transduced (*) or transduced with SP6-CD828BBZ (square), KDR1121-CD828Z (closed triangle), or KDR1121-CD828BBZ (open triangle) at varying effector-to-target ratios (x axis). Each data point reflects the mean of triplicates.

DETAILED DESCRIPTION OF THE INVENTION

An embodiment of the invention provides chimeric antigen receptors (CARs) comprising an antigen binding domain of a KDR-1121 or DC101 antibody, an extracellular hinge domain, a T cell receptor transmembrane domain, and an intracellular T cell receptor signaling domain.

A chimeric antigen receptor (CAR) is an artificially constructed hybrid protein or polypeptide containing the antigen binding domains of an antibody (scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response" as used herein means that the CAR can specifically bind to and immunologically recognize an antigen, such that binding of the CAR to the antigen elicits an immune response.

The CARs of the invention have antigen specificity for vascular endothelial growth factor receptor-2 (VEGFR-2) (also known as kinase domain region (KDR) in humans and fetal liver kinase-1 (Flk-1) in mice). VEGFR-2 is a receptor for vascular endothelial growth factor (VEGF), has seven extracellular domains, and is selectively expressed by vascular endothelial cells. VEGFR-2 is overexpressed by tumor endothelial cells in tumor blood vessels. VEGFR-2 additionally can be expressed by normal, non-tumor, or non-cancerous cells. However, in such a situation, the expression of VEGFR-2 by normal, non-tumor, or non-cancerous cells is not as robust as the expression by tumor or cancer cells. In this regard, the tumor or cancer cells can over-express VEGFR-2 or express VEGFR-2 at a significantly higher level, as compared to the expression of VEGFR-2 by normal, non-tumor, or non-cancerous cells. VEGFR-2 enhances tumor vascularization, growth, and metastasis. Without being bound to a particular theory, it is believed that by eliciting an antigen-specific response against VEGFR-2, the inventive CARs target and destroy VEGFR-2 expressing endothelial cells in the tumor vasculature, attack tumor vasculature, reduce or eliminate tumors, facilitate infiltration of immune cells to the tumor site, and enhance/extend anti-tumor responses.

Antiangiogenic tumor therapy provides many advantages. For example, because endothelial cells are genetically stable, drug resistance is believed to be unlikely. Additionally, the bloodstream provides easy access to the vascular endothelium and side effects and toxicity to normal tissues is believed to be limited. Moreover, the destruction of tumor blood vessels is believed to accelerate tumor cell death. Angiogenic endothelial cells are also believed to homogenously up-regulate antigen, e.g., VEGFR-2 expression. Moreover, antioangiogenic tumor therapy is applicable to many cancers, e.g., solid tumors that include a vascular supply.

The invention provides a CAR comprising an antigen binding domain of a KDR-1121 antibody or DC101 antibody. KDR-1121 (also known as IMC-1121B) is a human, anti-VEGFR-2 antibody. KDR-1121 binds to VEGFR-2 domain 3 and blocks VEGF/KDR interaction. DC101 is a rat anti-mouse VEGFR-2 antibody. Exemplary suitable KDR-1121 and DC101 antibodies are disclosed in U.S. Pat. Nos. 7,498,414; 5,840,301; 5,861,499 and WO 2007/095337, each of which is hereby incorporated by reference. In this regard, a preferred embodiment of the invention provides CARs comprising an antigen-binding domain comprising, consisting of, or consisting essentially of, a single chain variable fragment (scFv) of KDR-1121 (SEQ ID NO: 1) or DC101 (SEQ ID NO: 2).

In an embodiment of the invention, the CAR comprises an extracellular hinge domain, transmembrane domain, and optionally, an intracellular hinge domain comprising CD8 and an intracellular T cell receptor signaling domain comprising CD28, 4-1BB, and CD3ζ. CD28 is a T cell marker important in T cell co-stimulation. CD8 is also a T cell marker. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs). In this regard, a preferred embodiment of the invention provides an extracellular hinge domain, transmembrane domain, and optional intracellular hinge domain comprising, consisting essentially of, or consisting of SEQ ID NO: 3 (human CD8 extracellular hinge sequence, transmembrane sequence, and intracellular hinge sequence) or SEQ ID NO: 4 (mouse CD8 extracellular hinge and transmembrane sequences). The intracellular T cell receptor signaling domain comprises, consists essentially of, or consists of, SEQ ID NO: 5 (human CD28, 4-1BB, and CD3ζ intracellular T cell receptor signaling sequences) or SEQ ID NO: 6 (mouse CD28, 4-1BB, and CD3ζ intracellular T cell receptor signaling sequences).

In another embodiment of the invention, the CAR comprises an extracellular hinge domain, transmembrane domain, and intracellular T cell signaling domain comprising CD28 and CD3ζ. In this regard, a preferred embodiment of the invention provides an extracellular hinge domain, transmembrane domain, and intracellular T cell signaling domain comprising, consisting essentially of, or consisting of, SEQ ID NO: 7 (human CD28 extracellular hinge, transmembrane, and intracellular T cell signaling sequences) and SEQ ID NO: 8 (human CD3ζ intracellular T cell receptor signaling sequence).

In another embodiment of the invention, the CAR comprises an extracellular hinge domain and transmembrane domain comprising CD8 and an intracellular T cell receptor signaling domain comprising CD28 and CD3ζ. In this regard, a preferred embodiment of the invention provides an extracellular hinge domain and transmembrane domain comprising, consisting essentially of, or consisting of, SEQ ID NO: 4 (mouse CD8 extracellular hinge and transmembrane sequences). The intracellular T cell receptor signaling domain comprises, consists of, or consists essentially of, SEQ ID NO: 9 (mouse CD28 and CD3ζ sequence).

Additional embodiments of the invention provide CARs comprising, consisting of, or consisting essentially of, any of the amino acid sequences set forth in Table 1.

TABLE 1

| SEQ ID NO | scFv | Further Components |
| --- | --- | --- |
| 10 (KDR-hCD828BBZ) | KDR-1121 | Human CD8 extracellular hinge, transmembrane and intracellular hinge domains<br>Human CD28, human 4-1BB, and human CD3ζ intracellular T cell receptor signaling domains |
| 11 (KDR-hCD28Z) | KDR-1121 | Human CD28 extracellular hinge and transmembrane domains<br>Human CD28 and human CD3ζ intracellular T cell receptor signaling domains |
| 12 (DC101-mCD828BBZ) | DC101 | Mouse CD8 extracellular hinge and transmembrane domains<br>Mouse CD28, mouse 4-1BB, and mouse CD3ζ intracellular T cell receptor signaling domains |
| 13 (DC101-mCD828Z) | DC101 | Mouse CD8 extracellular hinge and transmembrane domains<br>Mouse CD28 and mouse CD3ζ intracellular signaling domains |
| 14 (DC101-hCD828BBZ) | DC101 | Human CD8 extracellular hinge, transmembrane and intracellular hinge domains<br>Human CD28, human 4-1BB, and human CD3ζ intracellular T cell receptor signaling domains |
| 15 (DC101-hCD28Z) | DC101 | Human CD28 extracellular hinge and transmembrane domains<br>Human CD28 and human CD3ζ, intracellular T cell receptor signaling domains |

The invention also provides related nucleic acids, recombinant expression vectors, host cells, populations of cells, antibodies, or antigen binding portions thereof, and pharmaceutical compositions relating to the CARs of the invention.

Another embodiment of the invention provides a method of detecting the presence of cancer in a host, comprising: (a) contacting a sample comprising one or more cells from the host with the CARs, the nucleic acids, the recombinant expression vectors, the host cells, the population of cells, the antibodies, and/or the antigen binding portions thereof of the invention, thereby forming a complex, (b) and detecting the complex, wherein detection of the complex is indicative of the presence of cancer in the host.

Another embodiment of the invention provides a method of treating or preventing cancer in a host, comprising administering to the host the CARs, the nucleic acids, the recombinant expression vectors, the host cells, the population of cells, the antibodies, and/or the antigen binding portions thereof of the invention in an amount effective to treat or prevent cancer in the host.

The host referred to herein can be any host. The host may be a mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs, polypeptides, and proteins described herein. The term "functional variant" as used herein refers to a CAR, polypeptide, or protein having substantial or significant sequence identity or similarity to a parent CAR, polypeptide, or protein, which functional variant retains the biological activity of the CAR, polypeptide, or protein of which it is a variant. Functional variants encompass, for example, those variants of the CAR, polypeptide, or protein described herein (the parent CAR, polypeptide, or protein) that retain the ability to recognize target cells to a similar extent, the same extent, or to a higher extent, as the parent CAR, polypeptide, or protein. In reference to the parent CAR, polypeptide, or protein, the functional variant can, for instance, be at least about 30%, 50%, 75%, 80%, 90%, 98% or more identical in amino acid sequence to the parent CAR, polypeptide, or protein.

A functional variant can, for example, comprise the amino acid sequence of the parent CAR, polypeptide, or protein with at least one conservative amino acid substitution. Alternatively or additionally, the functional variants can comprise the amino acid sequence of the parent CAR, polypeptide, or protein with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR, polypeptide, or protein.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The CAR, polypeptide, or protein can consist essentially of the specified amino acid sequence or sequences described herein, such that other components e.g., other amino acids, do not materially change the biological activity of the functional variant.

The CARs, polypeptides, and proteins of embodiments of the invention (including functional portions and functional variants) can be of any length, i.e., can comprise any number of amino acids, provided that the CARs, polypeptides, or proteins (or functional portions or functional variants thereof) retain their biological activity, e.g., the ability to specifically bind to antigen, detect diseased cells in a host, or treat or prevent disease in a host, etc. For example, the polypeptide can be about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The CARs, polypeptides, and proteins of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs, polypeptides, and proteins of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs, polypeptides, and/or proteins of embodiments of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the CARs, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive CARs, polypeptides, and proteins can be synthetic, recombinant, isolated, and/or purified.

An embodiment of the invention further provides an antibody, or antigen binding portion thereof, which specifically binds to an epitope of the CARs of the invention. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive CAR.

Methods of testing antibodies for the ability to bind to any functional portion of the inventive CAR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994).

An embodiment of the invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which is a truncated Fab fragment including the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Further provided by an embodiment of the invention is a nucleic acid comprising a nucleotide sequence encoding any of the CARs, polypeptides, or proteins described herein (including functional portions and functional variants thereof). In this regard, an embodiment of the invention provides nucleic acids comprising, consisting of, or consisting essentially of the nucleotide sequences of Table 2:

TABLE 2

| SEQ ID NO | scFv | Further Components |
| --- | --- | --- |
| 16 (KDR-hCD828BBZ) | KDR-1121 | Human CD8 extracellular hinge, transmembrane and intracellular hinge domains<br>Human CD28, human 4-1BB, and human CD3ζ, intracellular T cell receptor signaling domains |
| 17 (KDR-hCD28Z) | KDR-1121 | Human CD28 extracellular hinge and transmembrane domains<br>Human CD28 and human CD3ζ intracellular T cell receptor signaling domains |
| 18 (DC101-mCD828BBZ) | DC101 | Mouse CD8 extracellular hinge and transmembrane domains<br>Mouse CD28, mouse 4-1BB, and mouse CD3ζ intracellular T cell receptor signaling domains |

TABLE 2-continued

| SEQ ID NO | scFv | Further Components |
| --- | --- | --- |
| 19 (DC101-mCD828Z) | DC101 | Mouse CD8 extracellular hinge and transmembrane domains<br>Mouse CD28 and mouse CD3ζ intracellular signaling domains |
| 20 (DC101-hCD828BBZ) | DC101 | Human CD8 extracellular hinge, transmembrane and intracellular hinge domains<br>Human CD28, human 4-1BB, and human CD3ζ intracellular T cell receptor signaling domains |
| 21 (DC101-hCD28Z) | DC101 | Human CD28 extracellular hinge and transmembrane domains<br>Human CD28 and human CD3ζ, intracellular T cell receptor signaling domains |

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl)uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the CARs, polypeptides, or proteins, or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector.

In an embodiment, the recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2µ plasmid, λ, SV40, bovine papilloma virus, and the like.

The recombinant expression vector may comprise regulatory sequences, such as transcription and translation initiation and termination codons, which are specific to the type of host (e.g., bacterium, fungus, plant, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the CAR, polypeptide, or protein (including functional portions and functional variants thereof), or to the nucleotide sequence which is complementary to or which hybridizes to the nucleotide sequence encoding the CAR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Included in the scope of the invention are conjugates, e.g., bioconjugates, comprising any of the inventive CARs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, polypeptide, or protein, the host cell may be a mammalian cell. The host cell may be a human cell. While the host cell can be of any cell type, can originate from any type of tissue, and can be of any developmental stage, the host cell may be a peripheral blood lymphocyte (PBL). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), peripheral blood mononuclear cells (PBMCs), peripheral blood leukocytes (PBLs), tumor infiltrating cells, memory T cells, naïve T cells, and the like. The T cell may be a $CD8^+$ T cell or a $CD4^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs, polypeptides, proteins (including functional portions and variants thereof), nucleic acids, recombinant expression vectors, host cells (including populations thereof), and antibodies (including antigen binding portions thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the CARs, polypeptides, proteins, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive CAR materials can comprise more than one inventive CAR material, e.g., a polypeptide and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

The inventive CAR materials can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive CAR material in the pharmaceutical formulations can vary, e.g., from less than about 1%, usually at or at least about 10%, to as much as about 20% to about 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, *Remington: The Science and Practice of Pharmacy*, Lippincott Williams & Wilkins; 21st ed. (May 1, 2005).

The following formulations for oral, aerosol, parenteral (e.g., subcutaneous, intravenous, intraarterial, intramuscular, intradermal, interperitoneal, and intrathecal), and topical administration are merely exemplary and are in no way limiting. More than one route can be used to administer the inventive CAR materials, and in certain instances, a particular route can provide a more immediate and more effective response than another route.

Formulations suitable for oral administration can comprise or consist of (a) liquid solutions, such as an effective amount of the inventive CAR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive CAR material in a flavor, usually sucrose and acacia or tragacanth, as well as pastilles comprising the inventive CAR material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The inventive CAR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive CAR material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations, including those that are useful for transdermal drug release, are well known to those of skill in the art and are suitable in the context of embodiments of the invention for application to skin. The inventive CAR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR materials in each or various rounds of administration. By way of example and not intending to limit the invention, the dose of the inventive CAR material can be about 0.001 to about 1000 mg/kg body weight of the subject being treated/day, from about 0.01 to about 10 mg/kg body weight/day, about 0.01 mg to about 1 mg/kg body weight/day.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed or IFN-γ is secreted by T cells expressing the inventive CAR, polypeptide, or protein upon administration of a given dose of such T cells to a mammal, among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously. An exemplary therapeutic agent that can be co-administered with the CAR materials is IL-2. It is believed that IL-2 enhances the therapeutic effect of the inventive CAR materials. For purposes of the inventive methods, wherein host cells or populations of cells are administered to the host, the cells can be cells that are allogeneic or autologous to the host.

It is contemplated that the inventive pharmaceutical compositions, CARs, polypeptides, proteins, nucleic acids, recombinant expression vectors, host cells, or populations of cells can be used in methods of treating or preventing a disease in a host. Without being bound to a particular theory, the inventive CARs have biological activity, e.g., ability to recognize antigen, e.g., VEGFR-2, such that the CAR (or related inventive polypeptide or protein) when expressed by a cell is able to mediate an immune response against the cell expressing the antigen, e.g., VEGFR-2, for which the CAR is specific. In this regard, an embodiment of the invention provides a method of treating or preventing a disease in a host, comprising administering to the host any of the inventive CAR materials in an amount effective to treat or prevent the disease in the host.

An embodiment of the invention further comprises lymphodepleting the host prior to administering the inventive CAR materials.

With respect to the inventive methods, the cancer can be any cancer, including any of acute lymphocytic cancer, acute myeloid leukemia, alveolar rhabdomyosarcoma, bladder cancer, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and urinary bladder cancer. Preferably, the cancer is characterized by an angiogenic phenotype, e.g., a solid tumor or hematologic malignancy.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Methods of testing a CAR for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor α (TNF-α) or interleukin 2 (IL-2)). In addition, CAR function can be evaluated by measurement of cellular cytoxicity, as described in Zhao et al., *J. Immunol.*, 174: 4415-4423 (2005). Methods of testing a CAR for the ability to recognize target cells and for antigen specificity are described herein in the Examples section.

A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a host, the sample comprising cells of the host can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the host, e.g., the cells of any organ or tissue, including blood cells or endothelial cells.

In addition to the aforedescribed pharmaceutical compositions, the inventive CAR materials can be formulated as inclusion complexes, such as cyclodextrin inclusion complexes, or liposomes. Liposomes can serve to target the inventive CAR materials to a particular tissue. Liposomes also can be used to increase the half-life of the inventive CAR materials. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

A number of transfection techniques are generally known in the art (see, e.g., Graham et al., *Virology*, 52: 456-467 (1973); Sambrook et al., supra; Davis et al., *Basic Methods in Molecular Biology*, Elsevier (1986); and Chu et al., *Gene*, 13: 97 (1981). Transfection methods include calcium phosphate co-precipitation (see, e.g., Graham et al., supra), direct micro injection into cultured cells (see, e.g., Capecchi, *Cell*, 22: 479-488 (1980)), electroporation (see, e.g., Shigekawa et al., *BioTechniques*, 6: 742-751 (1988)), liposome mediated gene transfer (see, e.g., Mannino et al., *BioTechniques*, 6: 682-690 (1988)), lipid mediated transduction (see, e.g., Feigner et al., *Proc. Natl. Acad. Sci. USA*, 84: 7413-7417 (1987)), and nucleic acid delivery using high velocity microprojectiles (see, e.g., Klein et al., *Nature*, 327: 70-73 (1987)).

One of ordinary skill in the art will readily appreciate that the inventive CAR materials of the invention can be modified in any number of ways, such that the therapeutic or prophylactic efficacy of the inventive CAR materials is increased through the modification. For instance, the inventive CAR materials can be conjugated either directly or indirectly through a linker to a targeting moiety. The practice of conjugating compounds, e.g., inventive CAR materials, to targeting moieties is known in the art. See, for instance, Wadwa et al., *J Drug Targeting* 3: 111 (1995) and U.S. Pat. No. 5,087,616.

Alternatively, the inventive CAR materials can be modified into a depot form, such that the manner in which the inventive CAR materials is released into the body to which it is administered is controlled with respect to time and location within the body (see, for example, U.S. Pat. No. 4,450,150). Depot forms of inventive CAR materials can be, for example, an implantable composition comprising the inventive CAR materials and a porous or non-porous material, such as a polymer, wherein the inventive CAR materials are encapsulated by or diffused throughout the material and/or degradation of the non-porous material. The depot is then implanted into the desired location within the body and the inventive CAR materials are released from the implant at a predetermined rate.

The following examples further illustrate the invention but, of course, should not be construed as in any way limiting its scope.

EXAMPLES

Mice

Inbred female C57BL/6 (B6) mice were purchased from the National Cancer Institute-Frederick Cancer Research and Development Center (Frederick, Md.). BALB/c mice were purchased from the Jackson Laboratory (Bar Harbor, Me.). All animals were housed in specific, pathogen-free conditions in the National Institutes of Health animal facility, Bethesda, Md. Mice of 7-9 weeks of age were used in all experiments, which were performed according to animal experimental ethics committee guidelines of the National Institutes of Health, Bethesda, Md.

Cell Culture

The murine tumor lines used in these examples were B16-F10 (melanoma), MCA-205 (sarcoma), MC38 (colon adenocarcinoma), MB49 (bladder carcinoma), MC17-51 (sarcoma), CT-26 (colon carcinoma), Renca (renal carcinoma), 4T1 (mammary adenocarcinoma), C-1498 (myeloid leukemia), P815 (mastocytoma), EL-4 (lymphoma) and NIH-3T3 (mouse embryonic fibroblast). B16-F10, MCA-205, MC38, and NIH-3T3 cells were obtained from the cell culture depository of the Surgery Branch, National Cancer Institute, National Institutes of Health (Bethesda, Md.). CT26 and Renca cells were obtained from Dr. Weiss (NCI-Frederick, Frederick, Md.). SVEC4-10EHR1, MS1, and SVR were transformed mouse endothelial cell lines purchased from American Type Culture Collection (ATCC, Manassas, Va.). eBEND.3 is also a transformed mouse endothelial cell line (kindly provided by Dr. Frank Cuttita, Angiogenesis Core Facility at NCI, NIH, Gaithersburg, Md.). MB49-Flk1 and NIH3T3-Flk1 cells stably expressing mouse VEGF-2 protein were generated by transducing the MB49 and NIH-3T3 cell lines with a VSV-G pseudotyped lentiviral vector encoding full length mouse VEGFR-2 (X. Li et al., *Stem Cells* 25: 2987 (2007)) (kindly provided by Prof. Lena Claesson-Welsh, Uppsala University, Sweden).

Peripheral Blood Lymphocytes (PBL) used in these examples were cryopreserved PBMC obtained by leukapheresis of metastatic melanoma patients treated at the Surgery Branch, National Cancer Institute, NIH, Bethesda, Md. The following normal primary human cells used in these examples were procured from LONZA Walkersville, Inc. (Walkersville, Md.): microvascular endothelial cells (HM-VEC) derived from lung (HMVEC-L) or dermis (HMVEC-D), umbilical vein endothelial cells (HUVEC), small airway epithelial cells (SAEC), bronchial epithelial cells (HBEC), renal epithelial cells (HRE), mammary epithelial cells (HMEC), prostate epithelial cell (PrEC), smooth muscle myoblasts (HSMM), human primary skin fibroblasts. Other cell lines used were human embryonic kidney fibroblast cell lines 293 and 293-KDR, which is a stable transfectant expressing KDR (kindly provided by Dr. Maria Parkhurst, Surgery Branch, National Cancer Institute, NIH, Bethesda, Md.). The retroviral packaging cell lines 293GP and PG13 were obtained from ATCC. The human ecotropic packaging cell line Phoenix™ Eco was kindly provided by Gary Nolan, Stanford University, Stanford, Calif. (also available from Orbigen Inc., San Diego, Calif.).

All of the mouse tumor lines described above were maintained in R10 (RPMI1640 medium supplemented with 10% heat-inactivated fetal bovine serum (FBS), 100 U/ml penicillin, and 100 μg/ml streptomycin (all from Invitrogen™ Corporation, Grand Isle, N.Y.). All of the mouse endothelial cell lines, NIH-3T3 cells, 293, 293-KDR, 293GP, PG13, and Phoenix™ Eco cells were maintained in D10 (DMEM from Invitrogen™ Corporation supplemented with 10% heat-inactivated FBS, 100 U/ml penicillin, and 100 μg/ml streptomycin). All of the primary human cells were maintained in their respective culture media purchased from their manufacturer (Lonza Walkersville, Inc.). Mouse T cells were cultured in RPMI 1640 containing 10% heat-inactivated FBS, 100 U/ml penicillin, 100 μg/ml streptomycin, 0.05 mM 2-mercaptoethanol, 0.1 mM MEM non-essential amino acids, 1 mM pyruvate, 2 nM L-glutamine (all from Invitrogen™ Corporation), supplemented with 30 IU/ml of recombinant human interleukin (rhIL)-2 (Chiron, Emeryville, Calif.), hereafter referred as CM-M. Primary human lymphocytes were cultured in culture medium (CM-H) containing 50% RPMI1640, 50% AIM-V medium, 0.05 mM mercaptoethanol (all from Invitrogen™ Corporation), 300 IU/ml rhIL-2, and 10% heat inactivated human AB serum (Gemini Bio-Products, West Sacramento, Calif.). All of the cells were cultured at 37° C. under 5% $CO_2$ and 95% humidity.

Example 1

This example demonstrates a method of making a nucleotide sequence encoding a CAR comprising an antigen binding domain of a DC101 antibody, an extracellular hinge domain, a T cell receptor transmembrane domain, and an intracellular T cell receptor signaling domain.

All of the constructs were cloned into a retroviral vector (MSGV) containing a Murine Stem Cell Virus (MSCV) long terminal repeat (LTR) (known to be relatively resistant to in vivo silencing), incorporating the splicing and optimized start codon of the MFG-design of vectors described previously (Hughes, M S. et al. *Hum. Gene Ther.* 16: 457-472 (2005)).

The DC101-CD828BBZ CAR includes a single chain antibody (ScFv) against mouse VEGFR-2, hereafter referred as DC101 ScFv. DC101 ScFv comprises the heavy chain ($V_H$) and light chain ($V_L$) variable regions of a rat IgG specific to mouse VEGFR-2, (DC101; Imclone Systems Inc.) fused by a 218 bp linker. The DC101-CD828BBZ CAR is linked in-frame to the hinge and transmembrane (TM) regions of the mouse CD8α chain (corresponds to nucleotides 580 to 795 of Genbank identifier NM 001081110), which, in turn, is fused to the mouse intracellular signaling sequences derived from CD28 (corresponds to nucleotides 618 to 740 of Genbank identifier NM 007642), 4-1BB (corresponds to nucleotides 779 to 913 of Genbank identifier J04492), and CD3ζ (corresponds to nucleotides 313 to 635 of Genbank identifier NM 001113391) molecules.

The DC101-CD828Z construct has the same components as DC101-CD828BBZ CAR in a similar configuration and order except that it lacks the 4-1BB signaling domain.

A full length, 806 bp scFv cDNA designated DC101 ScFv was constructed using the polymerase chain (PCR) amplification and assembly technique as follows. The coding sequences for variable regions of heavy ($V_H$) and light chains ($V_L$) were amplified separately and recombined using a linker by a subsequent PCR reaction. The first set of PCR reactions were performed to amplify the leader sequence (LS) and variable region ($V_H$) of the heavy chain and also the variable region of light chain ($V_L$). The plasmids DC101 HC (clone 8.6) pCR2.1-TOPO and DC101 LC (clone 3.2) pCR2.1-TOPO, containing the heavy and light chain coding sequences, respectively, of the DC101 antibody (kindly provided by Dale Ludwig, Imclone Systems Inc.) were used as templates in the first PCR reaction to generate the LS plus $V_H$, and $V_L$ components of DC101 ScFv. The heavy chain forward primer, Heavy-F (SEQ ID NO: 22), was designed to span through the 5' end of the heavy chain leader sequence and contains an XhoI site at its 5' end. The light chain reverse primer, VL-R (SEQ ID NO: 23), contains a NotI site at its 3' end. The light chain forward primer, VL-F (SEQ ID NO: 24), was designed to include part of the 218 bp linker sequence and is compatible with the heavy chain reverse primer, VH-R (SEQ ID NO: 25).

In the second PCR reaction, the first PCR products, i.e., the heavy chain LS plus the $V_H$ and $V_L$ fragments, were assembled and amplified using the Heavy-F and VL-R primer set which resulted in the final DC101 ScFv fragment. The synthesized DC101 ScFv DNA fragments were sequence confirmed.

The nucleotide sequences of the mouse CD8α hinge and transmembrane domains and the intracellular signaling domains of mouse CD28, 4-1BB, and CD3ζ as described earlier were assembled in-frame in order in two different configurations, i.e., CD828BBZ or CD828Z. Both of these fragments were designed to have a NotI site at 5' end and the SalI and BamH1 sites at 3' end and were synthesized by GeneArt AG (Regensburg, Germany). The plasmids encoding these sequences were digested with NotI and BamHI restriction enzymes (New England Biolabs, Ipswich, Mass.) and ligated individually into the similarly digested MSGV vector plasmid described by Zhao et al. 2009 (in press). This subcloning step created two interim retroviral constructs, namely: MSGV-4D5-CD828BBZ and MSGV-4D5-CD828Z. To generate DC101 CAR encoding retroviral vectors MSGV-DC101-CD828BBZ (referred as DC101-CD828BBZ) and MSGV-DC101-CD828Z (referred as DC101-CD828Z), the XhoI and NotI-digested DC101 ScFv fragment was directly ligated into the MSGV-4D5-CD828BBZ and MSGV-4D5-CD828Z plasmids, replacing the 4D5 fragment.

This example demonstrated a method of making a nucleotide sequence encoding a CAR comprising a DC101 ScFv segment, mouse CD8α hinge and transmembrane segments, and intracellular mouse T cell signaling CD28, 4-1BB, and CD3ζ segments. This example also demonstrated a method of making a nucleotide sequence encoding a CAR comprising a DC101 ScFv segment, mouse CD8α hinge and transmembrane segments, and intracellular mouse T cell signaling CD28 and CD3ζ segments.

Example 2

This example demonstrates a method of making a nucleotide sequence encoding a CAR comprising an antigen binding domain of a KDR-1121 antibody, an extracellular hinge domain, a T cell receptor transmembrane domain, and an intracellular T cell receptor signaling domain.

The human VEGFR-2 (KDR) specific scFv was derived from KDR-1121 antibody, a fully human IgG against human KDR protein, hereafter referred as KDR1121-ScFv. The amino acid sequences of KDR-1121 $V_L$ and $V_H$ were derived from a published report (D. Lu et al., *J. Biol. Chem.* 278: 43496 (2003)). The codon optimized KDR ScFv comprising the $V_L$ and $V_H$ sequences linked by a 218 bp linker was designed and synthesized using a web-based DNA codon optimization algorithm (Gao, W. et al. *Biotechnol. Prog.* 20, 443-448 (2004)) using the primers generated by the software (SEQ ID NOs: 29-72). The synthesized KDR1121ScFv DNA fragments were sequence confirmed and subcloned in-frame into a MSGV-based vector containing the human CD28 hinge and transmembrane sequences linked to the human CD28 and CD3ζ intracellular signaling moieties described previously (J. Maher et al., *Nat. Biotechnol.* 20: 70 (2002)) to generate the MSGV-KDR1121CD28Z vector.

To obtain the MSGV-KDR1121CD28BBZ vector, the KDR1121ScFv was cloned in-frame into a similar MSGV vector (Zhao et. al *J. Immunol.* 2009 in press) containing the hinge and transmembrane sequences of the human CD8α chain linked to the cytoplasmic signaling domains of human CD28, 4-1BB, and CD3ζ molecules using standard molecular biology techniques. The sequence integrity of all of the vectors described in this paper was confirmed by DNA sequencing.

This example demonstrated a method of making a nucleotide sequence encoding a CAR comprising a KDR-1121 ScFv segment, human CD8α hinge and transmembrane segments, and intracellular human T cell signaling CD28, 4-1BB, and CD3ζ segments. This example also demonstrated a method of making a nucleotide sequence encoding a CAR comprising a KDR-1121 ScFv segment, human CD8α hinge and transmembrane segments, and intracellular human T cell signaling CD28 and CD3ζ segments.

Example 3

This example demonstrates a method of making a virus comprising a recombinant expression vector encoding a CAR comprising an antigen binding domain of a DC101 antibody, an extracellular hinge domain, a T cell receptor transmembrane domain, and an intracellular T cell receptor signaling domain.

PG13 cells were transfected with 9 mg of plasmid DNA (MSGV-DC101CD828BBZ or MSGV-DC101CD828Z prepared as described in Example 1 using the Lipofectamine™ 2000 transfection reagent (Invitrogen™). The supernatant from these transfected cells was harvested 24 hours later, filtered with a 0.45 µm pore-sized microfilter (MiUex-Ha; MiUipore, Bedford, M A), and used to transduce Phoenix™ Eco cells in the presence of 8 µg/ml protamine sulfate (Sigma). The transduction was repeated the next day. Sixteen hours later, the MSGV-DC101CD828BBZ or MSGV-DC101CD828Z CAR transduced Phoenix™ Eco cells were harvested and subjected to limiting dilution cloning. Clones were expanded, and high titer clones were selected by the dot-blot titration method as described previously (M. Onodera et al., *Hum. Gene Ther.* 8: 1189 (1997)). Retroviral supernatant from the 6 highest titer clones was generated. Briefly, 10 cm$^2$ tissue culture plates (Nunc™, Cole-Parmer®, Vernon Hills, Ill.) were seeded at 5×10$^6$ cells in 10 ml of D10. A medium exchange (10 ml) was performed on the next day. The supernatant from each clone was harvested 24 hours later and was evaluated by transducing mouse T cells as described below in Example 5 and measuring CAR expression on the surface of transduced T cells as described below under Example 6. A Phoenix™ Eco producer clone for each of the two constructs possessing the capability to transduce mouse T cells at high frequency and express the CAR at a high level were selected for production of retroviral supernatants to transduce mouse T cells in subsequent experiments.

This example demonstrated a method of making a virus comprising a recombinant expression vector encoding a CAR comprising a DC101 ScFv segment, mouse CD8α hinge and transmembrane segments, and intracellular mouse T cell signaling CD28, 4-1BB, and CD3ζ segments. This example also demonstrated a method of making a virus comprising a recombinant expression vector encoding a CAR comprising a DC101 ScFv segment, mouse CD8α hinge and transmembrane segments, and intracellular mouse T cell signaling CD28 and CD3ζ segments.

Example 4

This example demonstrates a method of making a virus comprising a recombinant expression vector encoding a CAR comprising an antigen binding domain of a KDR-1121 antibody, an extracellular hinge domain, a T cell receptor transmembrane domain, and an intracellular T cell receptor signaling domain.

A set of recombinant retroviral vectors expressing a CAR specific for human VEGFR-2 (KDR) was constructed. The KDR CAR vector termed KDR1121-hCD828BBZ included a ScFv from a fully human antibody KDR1121 (D. Lu et al., *J. Biol. Chem.* 278: 43496 (2003)) that was specific to the human KDR antigen. The KDR1121ScFv was linked to the hinge and transmembrane sequences from human CD8α, which, in turn, was fused to the intracellular sequences derived from the human CD28, 4-1BB, and CD3ζ domains of a TCR.

A second vector, referred to as KDR1121-hCD28Z, included KDR1121ScFv linked to the hinge and transmembrane sequences and the intracellular signaling domain of a human CD28 molecule, followed by the cytoplasmic sequences of a CD3ζ domain of a TCR.

MSGV-KDR1121-CD828BBZ and MSGV-KDR1121-CD828Z retroviral vectors producing stable PG13 producer cell clones were generated essentially as described in Example 3 with the following changes. Phoenix™ Eco cells were transfected with 9 mg of plasmid DNA (MSGV-KDR1121-CD828BBZ or MSGV-KDR1121-CD828Z) using the Lipofectamine™ 2000 transfection reagent (Invitrogen™). The supernatant from these transfected cells was harvested 24 hours later and used to transduce PG13 cells. The transduction was repeated the next day. Sixteen hours later, transduced PG13 cells were subjected to limited dilution cloning. Six high titer virus producing PG13 clones for each of the two constructs were identified by dot blot titration method (M. Onodera et al., Hum. Gene Ther. 8: 1189 (1997)). The supernatants were obtained from each of these clones as described in Example 3 and were evaluated by transducing human T cells as described below under Example 5 and measuring CAR expression on the surface of transduced T cells as described below in Example 15. A PG13 producer clone for each of the constructs possessing the capability to transduce mouse T cells at a high frequency and express the KDR CAR at high levels were selected for production of retroviral supernatants to transduce human T cells in subsequent experiments.

This example demonstrated a method of making a virus comprising a recombinant expression vector encoding a CAR comprising a KDR-1121 ScFv segment, human CD8α hinge and transmembrane segments, and intracellular human T cell signaling CD28, 4-1BB, and CD3ζ segments. This example also demonstrated a method of making a virus comprising a recombinant expression vector encoding a CAR comprising a KDR-1121 ScFv segment, human CD8α hinge and transmembrane segments, and intracellular human T cell signaling CD28 and CD3ζ segments.

Comparative Example 1

This example demonstrates a method of making a virus comprising a recombinant expression vector encoding an antigen binding domain of a DC101 antibody, an extracellular hinge domain, and a T cell receptor transmembrane domain, but lacking an intracellular T cell receptor signaling domain. This example also demonstrates a method of making a virus comprising a recombinant expression vector encoding a CAR comprising an antigen binding domain of a SP6 antibody, an extracellular hinge domain, a T cell receptor transmembrane domain, and an intracellular T cell receptor signaling domain.

To generate MSGV-DC101-CD8 (referred as DC101-CD8), the DC101-CD8 nucleotide sequence was amplified from the MSGV-DC101-CD828Z plasmid by PCR reaction using the primer set Heavy F (SEQ ID NO: 22) and a reverse primer (SEQ ID NO:26), which contain a TAA stop codon followed by a SalI restriction site. The PCR product was digested with XhoI and SalI and ligated into a similarly digested MSGV-DC101-CD828Z plasmid replacing the DC101-CD828Z fragment. The DC101-CD8 construct lacks an intracellular T cell signaling sequence and includes only the DC101 ScFv, mouse CD8α hinge, and mouse CD8α TM sequences.

The MSGV-SP6-CD828BBZ CAR (designated as SP6-CD828BBZ or SP6 CAR) was created as follows. The SP6 ScFv fragment was amplified by PCR from a plasmid encoding the SP6-ScFv (G. Gross, T. Waks, Z. Eshhar, Proc. Natl. Acad. Sci. U.S.A 86: 10024 (1989)) using the primers: SP6 forward (SEQ ID NO:27), which contains a XhoI site and SP6 reverse (SEQ ID NO:28), which contains a NotI site. A plasmid encoding the SP6 ScFv was kindly provided by Prof. Z. Eshhar (The Weizmann Institute of Science, Israel). The PCR product was then digested with XhoI and NotI enzymes and cloned into the similarly digested MSGV-DC101CD828BBZ plasmid replacing the DC101 ScFv. SP6 ScFv recognizes a hapten 2, 4, 6-trinitrophenyl (TNP). The SP6-CD828BBZ (SP6 CAR) construct includes SP6 ScFv and mouse CD8α hinge and transmembrane segments, and intracellular mouse T cell signaling CD28, 4-1BB, and CD3ζ segments.

Retroviruses encoding the DC101-CD8 and SP6-28Z CAR were produced transiently. Briefly, 293GP cells were plated on a poly-D-lysine coated dish (BD Biosciences, San Jose, Calif.) at a density of $5\times10^6$ cells in 10 ml of D10. On the following day, the culture media was replaced with 10 ml of D10 without antibiotics, and the cells were transfected with either the MSGV-DC101-CD8 or the MSGV-SP6-CD828BBZ plasmid along with a plasmid encoding the RD 114 envelope protein (C. D. Porter et al., Hum. Gene Ther. 7: 913 (1996)) using Lipofectamine™ 2000 (Invitrogen™ Corp.). The transfected cells were incubated at 37° C. and after 6 to 8 hours, the culture media was replaced with D10. The cells were incubated for another 36 to 48 hours at 37° C. Supernatant containing retroviruses was collected from the dishes and centrifuged to remove cellular debris and used to transduce mouse T cells.

This example demonstrated a method of making a virus comprising a recombinant expression vector encoding a DC101 ScFv segment and human CD8α hinge and transmembrane segments, but lacking intracellular human T cell signaling CD28, 4-1BB, and CD3ζ segments. This example also demonstrated a method of making a virus comprising a recombinant expression vector encoding a CAR comprising a SP6 ScFv segment, human CD8α hinge and transmembrane segments, and intracellular human T cell signaling CD28, 4-1BB, and CD3ζ segments.

Example 5

This example demonstrates a method of making a host cell comprising a recombinant expression vector encoding a CAR comprising an antigen binding domain of a DC101 or KDR-1121 antibody, an extracellular hinge domain, a T cell receptor transmembrane domain, and an intracellular T cell receptor signaling domain.

Spleens were harvested and crushed through a 40-μm nylon filter. After red-cell lysis, CD3$^+$ splenocytes were purified by using a mouse T cell negative isolation kit (Dynal®, Invitrogen™) and cultured in CM-M in the presence of 2 μg/ml ConA (Sigma-Aldrich®, St Louis, Mo.) and 1 ng/ml recombinant mouse (rm) IL-7 (R&D Systems®, Minneapolis, Minn.). After 24 hours, cells were harvested, centrifuged at 1200 rpm for 5 minutes at room temperature, and resuspended in fresh CM-M at $1\times10^6$ cells/ml. Cryopreserved human PBLs were thawed at 37° C. in CM-H, washed, and resuspended at a concentration of $1\times10^6$/ml in CM-H supplemented with 50 ng/ml mouse anti-human CD3 antibody (Orthoclone OKT®3, Ortho Biotech, Horsham, Pa.). After 2 days of culture, the cells were collected and resuspended in fresh T cell culture medium without OKT3 at $1\times10^6$ cells/ml.

Mouse and human lymphocytes were transduced using retroviruses produced as described in Example 3 or Example 4 using a similar transduction protocol on culture dishes that had been precoated with retroviral vectors as previously described (H. Hanenberg et al., Nat. Med. 2: 876 (1996)). To coat culture plates with vector, non-tissue culture-treated six-well plates (BD Biosciences) were first treated with 25 μg/ml recombinant fibronectin fragment (RetroNectin; Takara Bio. Inc, Japan). To these plates was then added 4-5 ml of retroviral vector supernatant, and the plates were spun at 2000 g for 2 hours at 32° C. Then the supernatant was removed, and stimulated mouse T cells or human lymphocytes were added to each well at 1×10⁶ cells/ml (2-3 ml/well) and the plates were spun at 1500 rpm for 10 min at room temperature. Cells were then incubated overnight at 37° C., and the procedure was repeated the following day (total of two transductions), after which the cells were expanded at 37° C. in a 5% $CO_2$ incubator and split as necessary to maintain cell density between 0.5 and 2×10⁶ cells/ml. Four or five days after transduction, lymphocytes were assayed for the presence of transgene product by flow cytometry and for activity by antigen-specific proliferation and cytokine release assays.

This example demonstrated a method of making a host cell comprising a recombinant expression vector encoding a CAR comprising a KDR-1121 or DC101 ScFv segment, CD8α hinge and transmembrane segments, and intracellular T cell signaling CD28, 4-1BB, and CD3ζ segments. This example also demonstrated a method of making a virus comprising a recombinant expression vector encoding a CAR comprising a KDR-1121 or DC101 ScFv segment, CD8α hinge and transmembrane segments, and intracellular T cell signaling CD28 and CD3ζ segments.

Example 6

This example demonstrates that host cells transduced with the nucleic acids of Example 1 expressed a CAR comprising a DC101 ScFv segment, hinge and transmembrane segments, and intracellular T cell signaling segments.

Mouse T cells were retrovirally transduced with retroviral vectors DC101-CD828Z or DC101-CD828BBZ CAR as described in Example 5 or were transduced with the DC101-CD8 or SP6-CD828BBZ vectors described in Comparative Example 1, or with an empty MSGV vector (lacking any of the CAR sequences). Surface expression of the retrovirally encoded transgene products in transduced CD3⁺ primary mouse T cells was determined by flow cytometry using the soluble mouse VEGFR-2-human IgG-FC fusion protein and PE-conjugated anti-human IgG-FC.

On day 4 post-transduction, cells were costained with anti-mouse CD8 antibody and CAR-specific reagents and were FACS analysed to determine the expression of transgene products in CD8⁺ and CD8⁻ T cell subsets. Detection of DC101 CAR on retrovirally transduced mouse T cells on day 4 after transduction was achieved by indirect immunofluorescence with soluble mouse (m) VEGFR2-hIgG.FC fusion protein (R&D Systems®, Minneapolis, Md.), followed by staining with a phycoerythrin (PE)-labeled goat anti-human IgG-FC antibody (eBioscience™, San Diego, Calif.). Briefly, 5×10⁵ cells were incubated with 2 μg of bovine serum albumin (BSA; Sigma-Aldrich®) or species-specific soluble mVEGFR2-hIgG.FC protein at 4° C. for 45 min. Cells were then washed in FACS buffer (phosphate buffered saline containing 1% FBS) and stained with PE-conjugated anti human IgG-FC (αhIgG.FC). At this step, mouse T cells were co-stained with peridinin chlorophyll (PerCP)-labeled anti-mouse CD8 (BD Pharmingen, San Diego, Calif.) at appropriate concentrations recommended by the manufacturer at 4° C. for 20-30 min, then washed and resuspended in FACS buffer. Cells incubated with 2 μg bovine serum albumin (BSA) and subsequently stained with PE-conjugated anti human IgG-FC (αhIgG-FC) and PerCP labeled anti-mouse CD8 served as a control.

To determine the expression of SP6 CAR, transduced mouse T cells were washed and suspended in FACs buffer. Aliquots of 5×10⁵ cells were incubated with biotin-labeled polyclonal goat anti-mouse F(ab)₂ antibodies (anti-Fab, Jackson Immunoresearch, West Grove, Pa.) or biotin-labeled normal polyclonal goat IgG antibodies (Jackson Immunoresearch) at 4° C. for 30 min. The cells were washed once, resuspended in FACS buffer, and costained with fluorescein isothocyanate (FITC)-labeled streptavidin (BD Pharmingen) and APC-labeled anti-mouse CD8 (BD Pharmingen) for 25 min at 4° C., then washed in FACS buffer, and resuspended in FACS buffer. Both CD4+ and CD8⁺ cells exhibited similar CAR expression profiles.

The results are shown in Tables 3 and 4A-4B.

TABLE 3

|  |  | DC101-CD8 | DC101-CD828Z | DC101-CD828BBZ | SP6-CD828BBZ |
|---|---|---|---|---|---|
| % Transduction | CD3+CD4+ | 83.2 ± 1.9 | 84 ± 1.7 | 79.0 ± 4.5 | 84.8 ± 2.7 |
|  | CD3+CD8+ | 80.8 ± 2.1 | 86 ± 1.6 | 78.2 ± 5.1 | 84.2 ± 3.9 |
| Mean Fluorescence | CD3+CD4+ | 114.3 ± 7.8 | 95 ± 7.3 | 76.5 ± 4.9 | 86.8 ± 6.1 |
| Intensity (MFI) | CD3+CD8+ | 108.5 ± 9.4 | 92 ± 6.2 | 75.8 ± 5.6 | 83.5 ± 4.8 |

In Table 3, transduction efficiency and level of expression of CAR in transduced mouse T cells are represented as percent transgene positive cells (% Transduction) and mean fluorescent intensity of expression (MFI), respectively. Data are represented as mean±SEM derived from 5 different experiments. As shown in Table 3, the DC101 CAR-expressing vectors efficiently and consistently transduced ConA/IL-7 activated mouse T cells (range about 79 to about 86%), which were mostly (~90%) CD8⁺ at 5 days post-transduction.

TABLE 4A

|  | Empty Vector | DC101-CD8 | DC101-CD828Z | DC101-CD828BBZ |
|---|---|---|---|---|
| % Cells Transduced (CD8+) (sVEGFR2-FC + αhIgG.FC-PE) | — | 72 | 81 | 69 |
| % Cells Transduced (CD8−) (sVEGFR2-FC + αhIgG.FC-PE) | — | 8 | 7 | 8 |
| % Cells Transduced (CD8+) (BSA + αHLGg.FC-PE) | — | — | — | — |
| % Cells Transduced (CD8−) (BSA + αHLGg.FC-PE) | — | — | — | — |

TABLE 4B

|  | SP6-CD828BBZ |
|---|---|
| % Cells Transduced (CD8+) (IsoAb-FITC) | — |
| % Cells Transduced (CD8-) (IsoAb-FITC) | — |
| % Cells Transduced (CD8+) (GAM-FITC) | 68 |
| % Cells Transduced (CD8-) (GAM-FITC) | 7.5 |

As shown in Table 4A, the intensity of CAR expression derived from the DC101 CAR comprising the 4-1BB signaling moiety was consistently lower than that derived from vectors lacking 4-1BB sequence in all the transduction experiments (n=5).

This example demonstrated the transduction efficiency of transducing host cells with the nucleic acids of Example 1 expressing a CAR comprising a DC101 ScFv segment, extracellular hinge and transmembrane segments, and intracellular T cell signaling segments.

Example 7

This example demonstrates that DC101-CD828Z and DC101-CD828BBZ CAR modified T cells are effective in generating an antigen-specific response in vitro as measured by proliferation.

The ability of DC101-CAR engineered T cells to proliferate in response to immobilized VEGFR-2 protein was measured. Untreated microtiter plates were coated individually with 5 μg/ml of bovine serum albumin (BSA, Sigma-Aldrich®), 5 μg/ml soluble mouse VEGFR2-hIgG.FC fusion protein (R&D Systems®), 5 μg/ml soluble mouse VEGFR2-hIgG.FC fusion protein (R&D Systems®), 2 μg/ml of a purified anti-mouse CD3 antibody (clone 145-2C11, BD Pharmingen), or 2 μg/ml purified mouse anti-human CD3 antibody (Orthoclone OKT®3) diluted in PBS for 3 hours at 37° C. Mouse T cells were transduced as described in Example 5 with retroviral vectors: SP6-CD828BBZ, DC101-CD8, DC101-CD828BBZ, DC101-CD828Z, or empty vector.

Four days after transduction, cells were washed and resuspended in their respective CM and plated at $10^5$ cells per well in 200 μl CM on antigen-coated micro titer plates. Cells were cultured for 3 days and pulsed with 1 μCi (0.037 MBq) [methyl-$^3$H] thymidine/well ((PerkinElmer® Life Sciences, Boston, Mass.) for the last 18 hours of culture. Cells were harvested on a Tomtec® cell harvester (PerkinElmer®, Wallac, Turku, Finland) and analyzed on a Wallac MicroBeta® liquid scintillation counter (PerkinElmer®, Waltham, Mass.) to determine the amount of incorporated radioactive thymidine. The assays were performed in triplicate wells. The results are shown in FIG. 1 (values are represented as mean±SEM).

Figure 1:
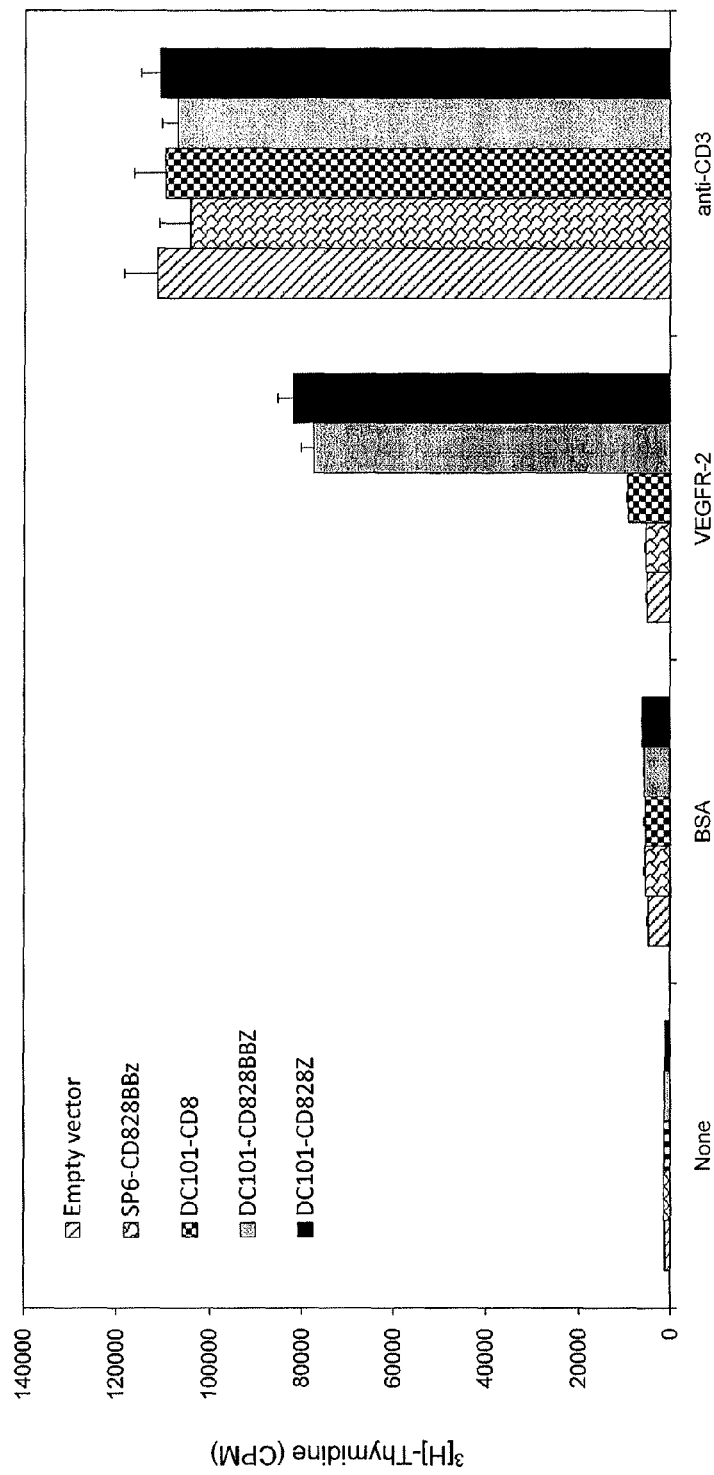
FIG. 1 is a graph of incorporation of $^3$[H]-thymidine (CPM) by cells transduced with an empty vector (diagonal stripe), SP6-CD828BBZ (herringbone), DC101-CD8 (checkered), DC101-CD828BBZ (grey), or DC101-CD828Z (black) as a measure of proliferation when cultured on plates bound with no antigen (none) or bound with BSA, VEGFR-2, or anti-CD3.

As shown in FIG. 1, while there were no differences between T cells transduced with various vectors to respond to immobilized anti-mouse CD3 antibody, only the T cells engineered with DC101-CARs containing intact intracellular signaling sequences (DC101-CD828Z and DC101-CD828BBZ) responded specifically to plate-bound target VEGFR-2 protein, as measured by proliferation. Further, the cells transduced with DC101-CARs proliferated in vitro in response to plate-bound target VEGFR-2 both with and without the 4-1BB signaling sequences.

This example demonstrated that DC101-CD828Z and DC101-CD828BBZ CAR modified T cells proliferate in vitro in response to stimulation by VEGFR-2 protein.

Example 8

This example demonstrates that DC101-CD828Z and DC101-CD828BBZ CAR modified T cells are effective in generating an antigen-specific response in vitro as measured by IFN-γ secretion.

Transduced mouse cells were tested for specific reactivity against plate-bound VEGFR-2 protein in IFN-γ release assays. Human PBL were transduced as described in Example 5 with retroviral vectors: SP6-CD828BBZ, DC101-CD8, DC101-CD828BBZ, DC101-CD828Z, or empty vector. The transduced cells were cultured on antigen-coated microtiter plates as described in Example 7 in 200 μl CM. Cell culture supernatants were harvested after 1 or 2 days and were analyzed by enzyme-linked immunosorbent assay (ELISA) for IFN-γ using commercially available ELISA kits (Endogen, Rockford, Ill.). The assays were performed in triplicate wells. The results are shown in FIG. 2 (values are represented as mean±SEM).

Figure 2:
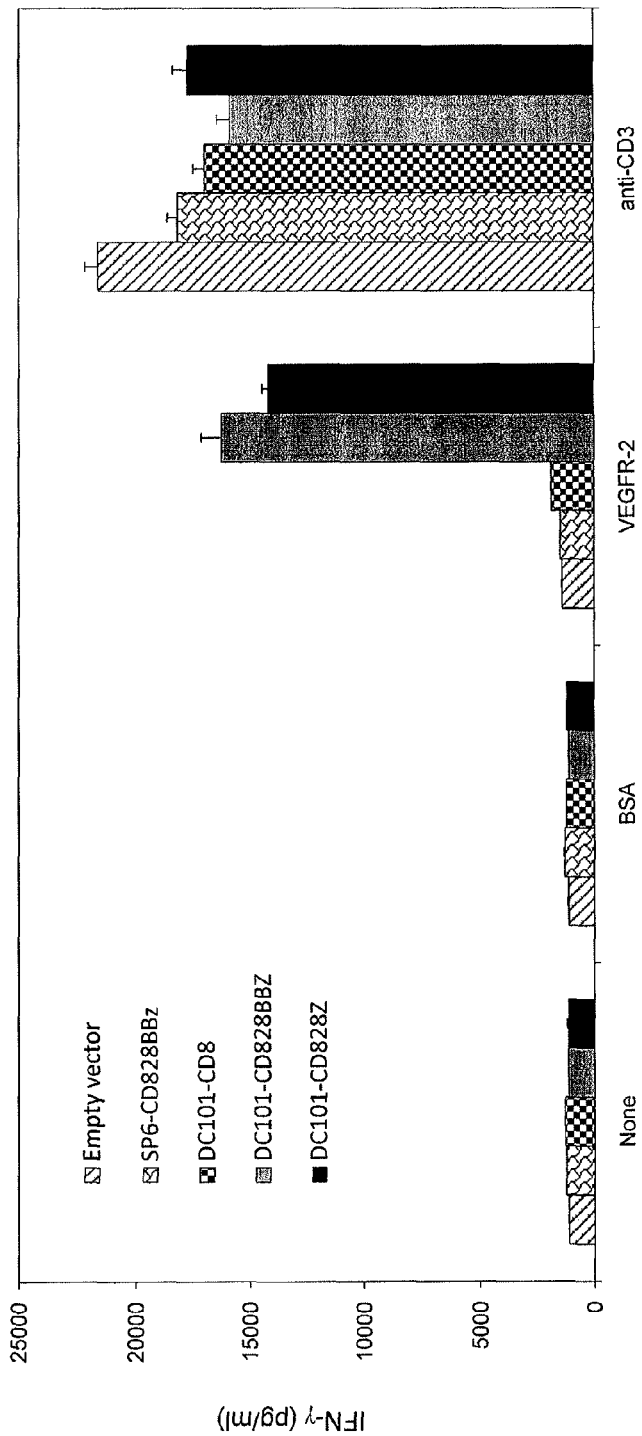
FIG. 2 is a graph of IFN-γ secretion (pg/ml) by cells transduced with an empty vector (diagonal stripe), SP6-CD828BBZ (herringbone), DC101-CD8 (checkered), DC101-CD828BBZ (grey), or DC101-CD828Z (black) when cultured on plates bound with no antigen (none) or bound with BSA, VEGFR-2, or anti-CD3.

As shown in FIG. 2, while there were no differences between T cells transduced with various vectors to respond to immobilized anti-mouse CD3 antibody, only the T cells engineered with DC101-CARs containing intact intracellular signaling sequences (DC101-CD828Z and DC101-CD828BBZ) responded specifically to plate-bound target VEGFR-2 protein, as measured by IFN-γ secretion. Further, the DC101-CARs secreted IFN-γ in response to plate-bound target VEGFR-2 both with and without the 4-1BB signaling sequences.

This example demonstrated that DC101-CD828Z and DC101-CD828BBZ CAR modified T cells secrete IFN-γ in vitro in response to stimulation by VEGFR-2 protein.

Example 9

This example demonstrates that DC101-CD828Z and DC101-CD828BBZ CAR modified T cells specifically recognize mouse cell lines expressing VEGFR-2 in vitro.

Mouse endothelial cell lines and tumor lines from various tissue origins were examined for cell surface expression of VEGFR-2 by flow cytometry. Briefly, cells were harvested (adherent cells were harvested using a cell scraper (Corning Incorporated, Corning, N.Y.)), washed in FACS buffer and resuspended in FACS buffer. Aliquots of $5 \times 10^5$ cells were incubated with 2 μg of recombinant DC101 antibody for 45 min at 4° C. Cells were then washed twice in FACS buffer and successively incubated with 2 μg soluble mVEGFR2-hIgG.FC protein and PE-labeled goat anti-human IgG.FC antibody for 30 min each at 4° C. Cells were then washed and analyzed by flow cytometry. Cells stained similarly but with rat IgG1 isotype control antibody instead of DC101 antibody in the first incubation step of the protocol served as control. Flow cytometry acquisition was performed with a FACS Calibur™ flow cytometer (BD Biosciences). Data were acquired and analyzed and analyzed using CellQuest™ software (Becton Dickson). A combination of forward angle light scatter and propidium iodide staining was used to gate out dead cells. The specificity of VEGFR-2 staining and the mean fluorescence intensity (MFI) of its expression on various cell types was determined using respective cell type stained with isotype control antibody.

The level of VEGFR-2 varied among the cell lines tested. While all transformed mouse endothelial cell lines (SVEC4-10EHR1, bEND.3, SVR, and MS1) showed high levels of VEGFR-2 expression, most of the cell lines showed either low (MC38, CT26, 4T1, and MCA205), or undetectable levels (MC17-51, B16-F10, RENCA, C4198, MB49, and NIH-3T3) of cell surface VEGFR-2 protein. Two of the VEGFR-2 negative cell lines MB49 and NIH-3T3, were stably transduced with a lentiviral vector expressing VEGFR-2 (MB49-Flk1 and 3T3-Flk1), and were used as positive controls in subsequent in vitro T cell functional assays.

Primary mouse T cells were untransduced or transduced as described in Example 5 with retroviral vectors: SP6-CD828BBZ, DC101-CD8, DC101-CD828BBZ, DC101-CD828Z, or empty vector. Four days later, cells were cultured alone or co-cultured with one of the following mouse cell lines in 200 μl CM: SVEC4-10EHR1, bEND-3, SVR, MS1, MC38, 4T1, P815, MCA205, MC17-51, EL-4, C1498, B16-F10, MB49, NIH-3T3, and cell lines transduced to express FLK-1: MB49-FLK-1 and 3T3-FLK-1. IFN-γ secretion was assayed as described in Example 8. The results are shown in FIG. 3 (presented as the mean values±SEM of triplicate wells).

As shown in FIG. 3, IFN-γ response was specifically detected in response to VEGFR-2 positive cell lines 3T3-Flk1, MB49-Flk1, SVEC4-10EHR1, bEND-3, SVR, MS1, 4T1, and MC38. The amount of IFN-γ secretion was highly correlated with the level of VEGFR-2 expressed on target cells ($R^2=0.9652$ for DC101-CD828BBZ; $R^2=0.9584$ for DC101-CD828Z). Reactivity was restricted to T cells expressing DC101-CAR containing intact T cell signaling domains. There were no significant differences in the performance of DC101-CARs with or without 4-1BB signaling sequences.

The specificity of the target antigen recognition was further confirmed by antibody blocking experiments. Target cells (bEnd.3, MB49, or MB49-FLK-1) were incubated with 10 μg/ml of either rat IgG1, anti-mouse VEGFR-1 antibody, or the anti-mouse VEGFR-2 antibody (DC101) at 37° C. for 1 hour and then cocultured with primary mouse T cells that were mock transduced or transduced with an empty vector or a retroviral vector encoding SP6-CD828BBZ CAR or DC101-CD828BBZ. The supernatants were harvested 24 hours later and assessed for IFN-γ by ELISA. As shown in FIG. 12, anti-VEGFR-2 antibody DC101 blocked the recognition of DC101-CAR transduced T cells against VEGFR-2$^+$ endothelial bEND.3 and MB49-Flk-1 tumor cell lines, while no blocking was observed either with an anti-mouse VEGFR-1 or isotype control antibodies.

This example demonstrated that DC101-CD828Z and DC101-CD828BBZ CAR modified T cells secrete IFN-γ in vitro in response to stimulation by VEGFR-2-expressing cells in vitro, and that the amount of IFN-γ secretion highly correlates with the level of VEGFR-2 expressed by target cells.

Example 10

This example demonstrates that adoptively transferred T cells expressing DC101 CARs are capable of inhibiting the growth of established tumors in vivo.

To determine therapeutic efficacy, DC101 CAR transduced cells were used to treat mice bearing established vascularized subcutaneous (s.c.) tumors.

Five hundred thousand tumor (B16-F10, MC38, MCA205, CT26, or Renca) cells were injected s.c. into groups of five mice (6-7 weeks of age). Between 10 and 12 days, when the tumor area reached an average size of approximately 50 mm$^2$, the mice were sublethally irradiated at 5 Gy TBI and injected with 20×10$^7$ syngeneic mouse T cells transduced with DC101-CD828BBZ CAR or an empty vector in conjunction with rhIL-2. Control groups received rhIL-2 alone or no treatment.

Starting volumes of tumors ranged from 40 to 80 mm$^2$. Unless indicated otherwise, lymphopenia was induced by nonmyeloablative (5 Gy) total body irradiation (TBI) of tumor-bearing mice on the day of adoptive transfer. Concomitantly, mice were treated intravenously (i.v.) with intraperitoneal (i.p.) injections of six doses of rhIL-2 (100,000 CU/0.5 mL/dose/mouse) twice a day with an interval of at least 6-8 hours for 3 days unless noted otherwise. If indicated, 5 B16-F10 tumor bearing mice were injected i.p. with a single dose of recombinant DC101 antibody or Rat IgG$_1$ both at 800 μg/dose/mouse in 500 μl PBS. All experiments were performed in a double blinded, randomized fashion, and independently at least twice with similar results. Each treatment group included five mice. Serial, blinded tumor measurements were obtained and the products of perpendicular diameters were plotted ±SEM. Statistics for tumor treatment were calculated using the Wilcoxon Rank Sum Test based on linear slopes of the tumor growth curves at each data point. Cumulative survival time was calculated by the Kaplan-Meier method and analyzed by the log-rank test. A P value of less than 0.05 was considered statistically significant.

The results are shown in FIGS. 4A-4B, 5A-5B, and 14A-14F. T cells expressing the DC101-CD828BBZ CAR (closed triangle) were capable of mediating a significant growth inhibitory effect against several poorly immunogenic tumors, including B16-F10 (FIG. 4A; P=0.009), MC38 (FIG. 4B; P=0.009), MCA205 (FIG. 14A, P=0.025), CT26 (FIG. 14C, P=0.009), and RENCA (FIG. 14E, P=0.008) tumors in syngeneic mice. T cells expressing the DC101-CD828BBZ CAR also increased the survival rates of B16-F10 (FIG. 5A), MC38 (FIG. 5B), MCA205 (FIG. 14B), CT26 (FIG. 14D), and RENCA (FIG. 14F) tumor bearing mice. There was no anti-tumor effect in untreated mice (closed circle), mice treated with T cells transduced with an empty vector (closed squares), or mice treated with IL-2 alone (closed diamond).

This example demonstrated that adoptively transferred T cells expressing DC101-CD828BBZ CAR inhibit the growth of B16-F10 and MC38 tumors and improve the survival of tumor-bearing mice in vivo.

Example 11

This example demonstrates that the anti-tumor effect of DC101 CAR-transduced T cells is cell-mediated.

Mice bearing established B16-F10 tumors were sublethally irradiated at 5 Gy TBI and received treatments similar to those described in Example 10: cells transduced with DC101-CD828BBZ CAR (closed triangle) or empty vector (closed squares) (FIG. 6A). Additional groups of 5 mice shown in this experiment received a single dose of 800 μg/mouse recombinant DC101 antibody (open triangle) or rat IgG1 control antibody (open diamond) in conjunction with rhIL-2 (FIG. 6A). Control groups received rhIL-2 alone (closed diamond) or were left untreated (closed circle), as shown in FIG. 6A.

As shown in FIG. 6A, T cells expressing the DC101-CD828BBZ CAR (closed triangle) were capable of inhibiting tumor growth. However, the other treatment groups, including treatment with recombinant DC101 antibody, had no effect on controlling the growth of established B 16 tumors.

Mice bearing B16-F10 tumors were treated with 2×10$^7$, 1×10$^7$, 5×10$^6$, or 2×10$^6$ syngeneic T cells transduced with DC101-CD828BBZ plus rhIL-2, or were untreated, treated with rhIL-2 alone, or treated with 2×10$^7$ T cells transduced with an empty vector plus rhIL-2. The treatment effect of DC101-CAR transduced T cells against the B16-F10 melanoma was a direct function of the number of cells administered (FIG. 15). Delay in tumor growth was achieved with as low as 2×10$^6$ DC101-CAR transduced T cells (P=0.008).

In most of the tumor treatment studies with a single dose of 2×10$^7$ DC101-CAR modified T cells, there was a rapid inhibition of tumor growth over a period of 2-3 weeks; during this remission period the parental tumor became necrotic and fibrous, but tiny nodules of viable tumor reappeared at the periphery of the parental tumor and eventually regenerated in many mice.

However, effective tumor treatment and tumor-free survival was achieved in mice bearing established B16-F10 or MCA205 tumors treated with 3 sequential weekly doses of $5 \times 10^6$ DC101-CAR transduced T cells and rhIL-2 (FIGS. 16A-16D). Mice bearing established subcutaneous B16 or MCA205 tumors were sublethally irradiated at 5Gy TBI and injected with a single dose of $2 \times 10^7$ DC101-CD28BBZ or empty vector-transduced syngeneic mouse T cells in conjunction with rhIL-2. Some groups received 3 sequential doses of $5 \times 10^6$ DC101-CAR or empty vector-transduced T cells at 7 to 10 days interval and 2 daily doses of rhIL-2 for 3 days concomitant to cell transfer. The no treatment group did not receive T cells or rhIL-2. The results with respect to tumor area are shown in FIGS. 16A (B16-F10) and 16B (MCA205) and the results with respect to survival are shown in FIGS. 16C (B16-F10) and 16D (MCA205).

This example demonstrated that adoptive transfer of T cells expressing DC101-CD828BBZ CAR were capable of inhibiting tumor growth while treatment with recombinant antibody failed to inhibit tumor growth.

Example 12

This example demonstrates that T cells transduced with a DC101 construct that lacks intracellular T cell signaling domains fails to induce an antitumor treatment effect in vivo.

Mice bearing established subcutaneous B16-F10 tumor were sublethally irradiated at 5 Gy TBI and treated with $20 \times 10^6$ syngeneic mouse T cells transduced with: DC101-CD828BBZ CAR vector, SP6-CD8S8BBZ CAR vector, DC101-CD8 vector (which lacks the T cell signaling domains), or an empty vector, as described in Example 10. All of the mice groups treated with T cells received rhIL-2 administration as described in Example 10. Animals in the control group were not treated with T cells or rhIL-2.

As shown in FIG. 6B, T cells expressing DC101 ScFv but lacking the intracellular T cell signaling molecules (open triangle) had no effect on controlling the growth of established B 16 tumor. Additionally, untreated mice (closed circle) and mice treated with T cells engineered with an irrelevant CAR (SP6 CAR) (open diamond) or an empty vector (closed square) failed to induce tumor inhibition (FIG. 6B). However, T cells expressing the DC101 CAR (closed triangle) were capable of inhibiting tumor growth.

This example demonstrated that adoptive transfer of T cells expressing DC101 CAR were capable of inhibiting tumor growth, while treatment with T cells expressing DC101 but lacking intracellular T cell signaling molecules and T cells expressing an irrelevant CAR each failed to inhibit tumor growth.

Example 13

This example demonstrates that cells transduced with DC101 CARs inhibited tumor growth in vivo both with and without a 4-1BB intracellular signaling domain.

As shown in FIG. 7, groups of 5 mice bearing established subcutaneous B 16-F10 tumors were sublethally irradiated at 5 Gy TBI and injected i.v. with $20 \times 10^6$ syngeneic T cells transduced with a DC101 CAR containing the 4-1BB intracellular signaling domain (DC101-mCD828BBZ, diamond) or without the 4-1BB intracellular signaling domain (DC101-CD828Z; triangle), or an empty vector (square), as described in Example 10. Control groups received no T cell therapy (circle) (FIG. 7). All of the T cell treatment groups shown in closed symbols received exogenous rhIL-2 administration and those represented in open symbols had not received rhIL-2 (FIG. 7). In all of the in vivo tumor treatment studies, mice were randomized and tumor size was measured in a blinded fashion. The products of the perpendicular diameters of the tumor are presented as the mean±SEM. Experiments were performed independently at least twice with similar results.

As shown in FIG. 7, T cells transduced with the DC101 CAR vector containing the 4-1BB intracellular signaling sequence (DC101-CD828BBZ) and those lacked the 4-1BB intracellular signaling sequence (DC101-CD28Z) performed equally well and were statistically indistinguishable (P=0.1) in delaying the growth of established bulky tumors.

This example demonstrated that adoptive transfer of T cells expressing DC101-CD828BBZ and DC101-CD28Z were each capable of inhibiting tumor growth in vivo.

Example 14

This example demonstrates that a 4-1BB signaling segment enhances the persistence of DC101 CAR modified T cells in vivo.

FACS analysis of tumor samples from two mice from each of the treatment groups that received DC101 CAR (DC101-CD828BBZ or DC101-CD828Z) transduced T cells and exogenous rhIL-2 as described in Example 10 were harvested at 30 days post-T cell transfer and individually analyzed for the presence of DC101 CAR expressing T cells by flow cytometry as described in Example 6. Tumor samples were mechanically disturbed into single cell suspensions and a low density cell fraction was prepared by gradient centrifugation over Ficoll. Cell surface expression of DC101 CAR was detected by incubating the cells successively with BSA or soluble mouse VEGFR-2-human IgG.FC fusion protein followed by PE-conjugated goat anti-human IgG.FC antibody. Cells were costained with APC-conjugated rat anti-mouse CD3. Percent CD3$^+$ T cells expressing DC101 CAR in the lymphocyte gate region of the forward and side scatter profiles is shown in Table 5.

TABLE 5

| | DC101-CD828BBZ | | DC101-CD828Z | |
|---|---|---|---|---|
| | BSA | VEGFR-2-human IgG.FC | BSA | VEGFR-2-human IgG.FC |
| Mouse 1 | — | 25.6 | — | 4.2 |
| Mouse 2 | — | 22.2 | — | 5.5 |

As shown in Table 5, mice treated with DC101-CD828BBZ CAR vector-engineered T cells had 4-5 fold more DC101 CAR-expressing CD3$^+$ CELLS in the tumor than mice treated with T cells carrying the DC101 CAR that lacked 4-1BB.

The example demonstrated that 4-1BB enhances the persistence of adoptively transferred antigen-specific T cells at the tumor site.

Example 15

This example demonstrates that DC101-CAR transduced T cells efficiently traffic to the tumor site.

C57BL/6 mice were subcutaneously injected with $2 \times 10^5$ B16-F10 tumor cells. On day 10 or 12, mice were irradiated at 5 Gy and treated intravenously with $20 \times 10^6$ DC101 CAR (DC101-CD828BBZ) or empty vector-transduced Thy1.1$^+$ syngeneic T cells in conjunction with rhIL-2, as described in Example 10.

At the time points indicated in Table 6A, tumors and spleens from an individual mouse from each group were excised and processed to obtain single cell suspensions and analysed by flow cytometry as described in Example 6. Spleens were crushed through a 40-μm nylon filter. After red-cell lysis, splenocytes were isolated. Single cell suspensions of tumors were made using a 40 μm nylon cell strainer (BD Biosciences), and lymphocytes were further separated by density gradient centrifugation using Lympholyte®-M (Cedarlane Laboratories, Burlington, Canada). Phenotype of mouse T cells isolated from spleen and tumor samples was determined by direct staining of cells with allophycocyanin (APC) conjugated rat anti-mouse CD3 and PE-labeled mouse anti-rat Thy1.1 antibody (both from BD Pharmingen) according to the manufacturer's recommendations. Aliquots of cells were stained with respective fluorochrome labeled isotype control antibodies to determine the specificity of staining. Percentage of $CD3^+$ $Thy1.1^+$ cells in the lymphocyte gated population was determined by flow cytometry. Cells were acquired and analyzed using the CellQuest software (BD Biosciences). Cells in the lymphocyte gate region of the tumor cell preparations and all the cell populations of splenocytes were included in the analysis. Quadrants were established based on the isotype control antibody staining. Representative FACS data is shown in Table 6A (percentage of $CD3^+$ $Thy1.1^+$ cells) and pooled data obtained from three different mice from independent experiments is shown in Table 6B (percentage of $CD3^+Thy1.1^+$ cells).

TABLE 6A

| | Spleen | | Tumor | |
|---|---|---|---|---|
| | DC101-CD828BBZ | Empty Vector | DC101-CD828BBZ | Empty Vector |
| Day 3 | 17 | 7 | 54 | 26 |
| Day 6 | 15.2 | 3.2 | 70.4 | 31 |
| Day 9 | 5.3 | 3.1 | 53 | 3.2 |

TABLE 6B

| | Spleen | | Tumor | |
|---|---|---|---|---|
| | DC101-CD828BBZ | Empty Vector | DC101-CD828BBZ | Empty Vector |
| Day 3 | 15.1 | 9.9 | 40.2 | 23.4 |
| Day 6 | 27.8 | 6.6 | 75.5 | 27.8 |
| Day 9 | 15.3 | 4.4 | 68 | 9.3 |

By day 3, adoptively transferred T cells trafficked similarly to spleen and tumor irrespective of their genetic modification. However, at day 6 and 9, trafficking to the tumor was far greater for the DC101 CAR-endowed T cells. This increase in trafficking to and homing of VEGFR-2-specific T cells at the tumor site was reproducibly observed in multiple experiments. These findings were further confirmed by direct visualization of adoptively transferred $Thy1.1^+$ T cells using confocal microscopy after staining the tumor sections with Thy1.1 specific antibody.

Tumor samples were obtained from C57BL/6 mice bearing B16-F10 tumors treated with DC101-CD828BBZ CAR or empty vector transduced T cells and rhIL-2 on day 4 post-ACT. Tumor sections were stained for Thy1.1 antigen expressed on transferred T cells or the endothelial cell marker CD31 together with 4',6-diamidino-2-phenylindole (DAPI) to show the nucleus and analyzed using fluorescence microscopy. Tumor samples taken on day 4 after cell transfer from mice treated with DC101-CAR transduced $Thy1.1^+$ T cells contained more $Thy1.1^+$ T cells than those treated with empty vector transduced cells. At this time point, the tumor vessels contained DC101-CAR transduced T cells in close association with endothelial cells in the tumor vessels. Furthermore, tumor sections stained with the endothelial cell marker CD31 revealed a reduced number of vessels in the tumor of mice treated with DC101-CAR transduced T cells compared to those treated with empty vector transduced T cells.

To determine if the enhanced trafficking and increase in numbers of DC101-CAR transduced T cells in the tumor are the result of any intrinsic differences in expression of chemokine receptors between CAR transduced and empty vector transduced T cells, enriched splenic $CD3^+$ T cells were transduced with an empty vector or vectors encoding DC101-CD828BBZ, DC101-CD828Z, or SP6-CD828BBZ. Five days after transduction, cells were analysed by FACS for cell surface expression of CD62L molecule and chemokine receptors (CXCR4, CXCR3, CCR9, and CCR7) that are known to be involved in homing and/or efficient trafficking of T cells in vivo.

There were no differences between the T cells transduced with retroviral vectors expressing DC101-CD828BBZ, DC101-CD828Z, SP6-CD828BBZ, or empty vector, in the levels of expression of the chemokine receptors CCR7, CCR9, CXCR-3, and CXCR-4 as well as the homing molecule L-selectin (CD62L) that are known to be involved in the trafficking of T cells. Accordingly, the enhanced trafficking and increase in numbers of DC101-CAR transduced T cells in the tumor seem to be the consequence of in vivo target antigen engagement rather than the result of any intrinsic differences in antigen-independent mechanisms such as increased expression of chemokine receptors between CAR transduced and empty vector transduced T cells.

This example demonstrated that trafficking to the tumor is far greater for the DC101 CAR endowed T cells than the cells transduced with an empty vector at days 6 and 9 following adoptive transfer.

Example 16

This example demonstrates that host cells transduced with the nucleic acids of Example 2 express a CAR comprising a KDR1121ScFv segment, extracellular hinge and transmembrane segments, and intracellular T cell signaling segments.

Detection of KDR CAR on transduced human T cells was performed 5 days post-transduction as described in Example 6, except that soluble human (h) VEGFR2-hIgG.FC fusion protein was used in the staining protocol and the cells were costained with PerCP-labeled mouse anti-human CD3 antibody (BD Pharmingen). Flow cytometry acquisition was performed with a FACS Calibur™ flow cytometer (BD Biosciences). Data were acquired and analyzed and analyzed using CellQuest™ software (Becton Dickson). A combination of forward angle light scatter and propidium iodide staining was used to gate out dead cells. The CAR-specific staining and the mean fluorescence intensity (MFI) of its expression on transduced T cells were determined using respective cell types stained with isotype control antibodies. Quadrants were established based on relevant isotype controls. The results are shown in Table 7.

TABLE 7

|  | KDR1121-hCD28Z | KDR1121-hCD828BBZ |
|---|---|---|
| % Transduction | 85 ± 1.7 | 79 ± 1.5 |
| Mean Fluorescence Intensity (MFI) | 160 ± 16 | 123 ± 21 |

As shown in Table 7, the KDR CAR encoding retroviral vectors of Example 2 transduced human PBLs at a high frequency, resulting in about 79 to about 85% of the CD3+ T cells expressing the CAR on cell surface.

Even though both vectors could transduce human PBLs at a comparable rate, the MFI of CAR expression driven from the KDR-CD828BBZ CAR vector, which possessed the 4-1BB sequence, was slightly compromised as shown in Table 8.

TABLE 8

|  | Mock transduced | KDR1121-CD28Z | KDR1121-CD828BBZ |
|---|---|---|---|
| % Cells CD3+ transduced (sKDR-hIgG-FC + αhIgG.FC-PE) | — | 84 | 79.5 |
| % Cells CD3+ transduced (BSA + αhIgG.FC-PE) | — | — | — |

This example demonstrated the transduction efficiency of transducing host cells with the nucleic acids of Example 2 expressing a CAR comprising a KDR1121ScFv segment, extracellular hinge and transmembrane segments, and intracellular T cell signaling segments.

Example 17

This example demonstrates that KDR1121-CD28Z and KDR1121-CD828BBZ CAR modified T cells are effective in generating an antigen-specific response in vitro as measured by proliferation.

Microtiter plates were coated with BSA, soluble KDR-hIgG.FC fusion protein, or anti human CD3 mAb as described in Example 7. OKT3 stimulated human PBLs were transduced with as described in Example 5 with retroviral vectors: KDR-CD28Z or KDR-CD28BBZ or mock transduced. Seven days later, cells were cultured on antigen coated micro titer plates for 3 days, pulsed with $^3$[H]-thymidine for 18 hours, and analyzed for thymidine incorporation as a measure of proliferation, as described in Example 7. The assays were performed in triplicate and values are represented as mean±SEM. The results are shown in FIG. 8.

As shown in FIG. 8, while there were no differences between T cells transduced with various vectors to respond to immobilized anti-mouse CD3 antibody, only the T cells engineered with KDR1121-CARs responded specifically to plate-bound target VEGFR-2 protein, as measured by proliferation. Further, the cells transduced with KDR1121 CARs proliferated in vitro in response to plate-bound target VEGFR-2 both with and without the 4-1BB signaling sequences.

This example demonstrated that KDR1121-CD28Z and KDR1121-CD828BBZ CAR modified T cells proliferate in vitro in response to stimulation by VEGFR-2 protein.

Example 18

This example demonstrates that KDR1121-CD28Z and KDR1121-CD828BBZ CAR modified T cells are effective in generating an antigen-specific response in vitro as measured by IFN-γ secretion.

Transduced human PBLs were tested for specific reactivity against plate-bound VEGFR-2 protein as well as target cells expressing VEGFR-2 in IFN-γ release assays. Human PBL were transduced as described in Example 5 with retroviral vectors: KDR1121-CD828BBZ or KDR1121-CD28Z or were mock transduced. The transduced cells were cultured on antigen-coated microtiter plates as described in Example 7 in 200 μl CM. Cell culture supernatants were harvested after 1 or 2 days (mouse T cells) or after 1 day (human T cells) and were analyzed by enzyme-linked immunosorbent assay (ELISA) for IFN-γ using commercially available ELISA kits (Endogen, Rockford, Ill.). The assays were performed in triplicate wells. The results are shown in FIG. 9 (values are represented as mean±SEM).

As shown in FIG. 9, while there were no differences between T cells transduced with various vectors to respond to immobilized anti-mouse CD3 antibody, only the T cells engineered with KDR1121-CARs responded specifically to plate-bound target VEGFR-2 protein, as measured by IFN-γ secretion. Further, the cells transduced with KDR1121CARs secreted IFN-γ in vitro in response to plate-bound target VEGFR-2 both with and without the 4-1BB signaling sequences.

This example demonstrated that KDR1121-CD28Z and KDR1121-CD828BBZ CAR modified T cells secrete IFN-γ in vitro in response to stimulation by VEGFR-2 protein.

Example 19

This example demonstrates that human PBLs transduced with KDR1121-CD828BBZ and KDR1121-CD28Z generate an antigen-specific response in vitro when co-cultured with VEGFR-2 (KDR)-expressing target cells, as measured by IFN-γ secretion.

The ability of KDR CAR modified T cells in recognizing cells expressing KDR protein was tested. PBLs from 3 different donors were transduced with KDR1121-CD828BBZ and KDR1121-CD28Z CAR as described in Example 5 or were mock transduced. Eight days post-transduction, the transduced cells were cultured alone or were cocultured for 24 hours with KDR negative 293 cells or 293-KDR cells, a stable transfectant expressing high levels of KDR protein as described in Example 9. Culture supernatants were analyzed for IFN-γ secretion as described in Example 8. The results are shown in FIG. 10.

As shown in FIG. 10, both the KDR1121-CD828BBZ and KDR1121-CD28Z vectors conferred a similar level of specificity and functionality to the transduced human T cells, as evidenced from their ability to specifically recognize only the KDR expressing 293-KDR cells and not the 293 cells.

This example demonstrated that KDR1121-CD28Z and KDR1121-CD828BBZ CAR modified T cells secrete IFN-γ in vitro in response to stimulation by VEGFR-2 (KDR)-expressing cells.

Example 20

This example demonstrates that KDR-1121 CAR modified T cells secrete IFN-γ in vitro in response to stimulation by VEGFR-2-expressing cells in vitro.

A panel of normal primary human endothelial and epithelial cells from different tissue origins and muscle myoblasts (293A2, HMVEC-Dermal, HMVEC-Lung, HUVEC, skin fibroblasts, SAEC, HBEC, HRE, HMEC, PrEC, HSMM) cultured in vitro for a short period, were examined for KDR expression by flow cytometry. The KDR protein was readily detectable only transduced cells (293A2-KDR) and in cultured primary endothelial cells (i.e., HMVEC-D, HMVEC-L, and HUVEC) and not in any of the primary epithelial cells and myoblasts tested. The intensity of KDR expression was higher in skin-derived human dermal microvascular endothelial cells (HMVEC-D) compared to lung-derived HMVEC (HMVEC-L) or HUVECs.

Human PBLs transduced as described in Example 5 with KDR1121-CD828BBZ or mock-transduced. Four days later, target cells were cultured alone, transduced cells were cultured alone, or transduced cells were co-cultured with one of the following cell lines in 200 µl CM: 293A2, HMVEC-Dermal, HMVEC-Lung, HUVEC, skin fibroblasts, SAEC, HBEC, HRE, HMEC, PrEC, HSMM or 293A2-KDR. IFN-γ secretion was assayed as described in Example 8. The results are shown in FIG. 11 (presented as the mean values±SEM of triplicate wells).

As shown in FIG. 11, the KDR CAR-transduced cells secreted IFN-γ only in response to KDR positive cells (HMVEC-D, 293-KDR cells, HMVEC-L, and HUVEC) irrespective of their tissue origin and failed to recognize any of the other primary cells tested.

Consistent with these results, in cytotoxicity assays, the KDR1121-hCD828BBZ and KDR1121-hCD28Z CAR modified T cells specifically lysed the KDR positive target cells but not the KDR negative cell types, whereas the mock or SP6-CAR transduced T cells were unable to lyse any of the target cells tested (FIG. 19).

This example demonstrated that KDR1121-CD28Z and KDR1121-CD828BBZ CAR modified T cells secrete IFN-γ in vitro in response to stimulation by VEGFR-2 (KDR)-expressing cells in vitro, regardless of tissue origin.

Example 21

This example demonstrates that primary mouse T cells modified to express VEGFR-2 CAR specifically lyse mouse cells expressing VEGFR-2.

Primary mouse T cells, mock transduced or transduced with an empty vector or with a retroviral vector expressing SP6-CD828BBZ, DC101-CD8, DC101-CD828Z or DC101-CD828BBZ were incubated with target cells (SVEC4-10EHR1, 4T1, RENCA, MB49, bEND.3, MC38, MC17-51, MB49-Flk1, MS1, CT26, B16-F10, 3T3, SVR, MCA205, C1498, 3T3-Flk1) at varying effector-to-target ratios (50, 17, 5.6, 1.9) and cell lysis was determined by using the standard $Cr^{51}$ release assay.

Consistent with the results obtained in Example 9 and as shown in FIG. 13, in the cytotoxicity assays, the DC101-CAR modified T cells specifically lysed the VEGFR-2 positive target cells but did not lyse the VEGFR-2 negative cell types. In contrast, the mock, empty vector, or SP6-CAR transduced T cells were unable to lyse any of the target cells tested (FIG. 13).

Example 22

This example demonstrates that DC101-CAR expressing T cells generate an anti-tumor response in the presence or absence of host preconditioning with irradiation.

Depletion of host immune cells prior to adoptive cell transfer (ACT) can enhance the anti-tumor efficacy of transferred antigen-specific T cells by eliminating immune suppressor cells as well as lymphocytes that compete with the transferred cells for homeostatic cytokines. Therefore, in previous adoptive T cell therapy experiments, mice received 5 Gy total body irradiation (TBI) prior to cell transfer. Irradiation, however, could potentially adversely alter or damage tumor vasculature and/or skew the expression of the target antigen, VEGFR-2.

Therefore the in vivo anti-tumor activity of DC101-CAR engineered T cells was tested in mice with or without host lymphodepletion prior to adoptive T cell transfer. C57BL/6 mice bearing subcutaneous B16-F10$^7$ tumors received 2×10 syngeneic T cells transduced with DC101-CAR, SP6-CAR, or an empty vector plus rhIL-2, or were not treated with T cells, with or without 5 Gy TBI prior to T cell transfer.

Consistent with the findings from previous experiments, the DC101-CAR expressing T cells again reproducibly generated an anti-tumor response in lymphodepleted mice compared to those engineered with SP6-CAR or empty vector (FIG. 17, P=0.009). The tumor inhibitory effect was statistically indistinguishable between the treatment groups that received DC101-CAR T cells either in the presence or absence of host preconditioning with irradiation (P=0.251).

This example demonstrated that DC101-CAR expressing T cells generate an anti-tumor response with or without prior host lymphodepletion.

Example 23

This example demonstrates that toxicities observed with the adoptively transferred VEGFR-2 CAR transduced T cells can be reduced by administering reduced numbers of T cells or purified CD8$^+$ T cells transduced with DC101-CAR.

In the tumor treatment studies performed in a total of 135 C57BL/6 mice bearing established subcutaneous tumors of different histologies, the adoptively transferred syngeneic T cells contained greater than 90% CD8$^+$ T cells. No treatment related morbidity or mortalities were documented in those mice that received 5 Gy total body irradiation, up to 2×10$^7$ T cells transduced with either DC101-CD828BBZ or DC101-CD828Z CAR, and high dose IL-2. Histopathologic analysis of various organs in C57BL/6 mice treated with maximum numbers (2×10$^7$) of VEGFR-2 CAR modified T cells showed no evidence of treatment related toxicity, despite reports of low levels of VEGFR-2 expression in vascularized tissues such as kidney, retina, and pancreas.

In contrast, severe toxicity was seen in tumor bearing BALB/c mice treated similarly with 2×10$^7$ DC101-CAR transduced syngeneic T cells. However, in BALB/c mice with established CT26 or RENCA tumor, comparable anti-tumor effects were achieved without any treatment related toxicities if the number of administered T cells was reduced to 5×10$^6$ or by administering 2×10$^7$ purified syngeneic CD8$^+$ T cells transduced with DC101-CAR (FIGS. 18A and 18B). Histopathologic analysis of BALB/c mice treated with 2×10$^7$ DC101-CAR transduced T cells and IL-2 revealed findings characteristic of cytokine induced hypotension including multifocal mild coagulation necrosis in the liver and mild hepatic pericholangitis and pulmonary perivasculitis, villous atrophy, villous blunting, and crypt epithelial hyperplasia of the small intestine and colon. No abnormalities in the gross appearance of the heart, lungs, liver, kidneys, spleen, pancreas, uterus, ovaries, or brain were seen.

The differences in toxicity seen in C57BL/6 compared to BALB/c mice were apparently due to the increased numbers of CD4$^+$ T cells present in the final cell product used in adoptive transfer. Although the CD3$^+$ T cells obtained from BALB/c spleens were cultured similarly to that of the C57BL/6 mice, the final BALB/c cell product (cultured for 5-6 days) contained approximately 60% CD8$^+$ T cells and 40% CD4$^+$ T cells at the time of adoptive transfer. No toxicity was seen in BALB/c mice (in 3 independent experiments involving 15 tumor bearing mice) treated with reduced numbers ($5\times10^6$) of unseparated T cells or $2\times10^7$ purified CD8$^+$ T cells transduced with DC101-CAR, while mice receiving $2\times10^7$ DC101-CAR modified T cells containing both CD8$^+$ T cells (~60%) and CD4$^+$ (~40%) T cells showed morbidity and mortality in the same experiment presented in FIGS. 18A and 18B. These findings were further evaluated in B16 tumor bearing C57BL/6 mice, in which morbidity and mortalities were evidenced if the mice were treated with purified CD4$^+$ T cells transduced with VEGFR-2 CAR or $2\times10^7$ T cells containing a 1:1 mixture of $1\times10^7$ purified CD8$^+$ and $1\times10^7$ CD4$^+$ T cells, both transduced with CAR. Whereas, effective tumor treatment was achieved with no adverse effects, in mice treated with either $2\times10^7$ unseparated CD3$^+$ T cells (>90% CD8$^+$ T cells) or purified CD8$^+$ T cells transduced with VEGFR-2 CAR (FIG. 18C).

In multiple experiments, treatment of non-tumor bearing BALB/c or C57BL/6 mice with $2\times10^7$ CAR transduced T cells containing equal numbers of CD4$^+$ and CD8$^+$ T cells was well tolerated with no adverse effect or toxicities. Thus, the cause of the toxicities observed with the adoptively transferred VEGFR-2 CAR transduced T cells appears to be restricted to the CD4$^+$ T cell recognition of the target antigen VEGFR-2 in the tumor vascular network and subsequent downstream molecular events rather than their off target cell-mediated cytotoxicities to normal vessels or tissues.

This example demonstrated that administering reduced numbers of T cells or purified CD8$^+$ T cells transduced with DC101-CAR can reduce toxicities observed with adoptively transferred VEGFR-2 CAR transduced T cells.

Example 24

This example demonstrates a method of administering a population of cells expressing an anti-VEGFR2CAR to human patients with metastatic cancer.

Cell Preparation

PBMC will be obtained by leukapheresis (approximately $1\times10^{10}$ cells). Whole PBMC will be cultured in the presence of anti-CD3 (OKT3) and aldesleukin in order to stimulate T-cell growth. Transduction is initiated by exposure of approximately $1\times10^7$ to $5\times10^8$ cells to supernatant containing the anti-VEGFR2CAR retroviral vector (comprising KDR1121-hCD828BBZ nucleotide sequence SEQ ID NO: 16). These transduced cells will be expanded and tested for their anti-tumor activity. Successful CAR gene transfer will be determined by FACS analysis for the CAR protein and anti-VEGFR2 reactivity will be tested by cytokine release as measured on transfected cells. Successful CAR gene transfer for each transduced PBL population will be defined as >10% CAR positive cells and for biological activity, gamma-interferon secretion will be at least 200 pg/ml.

Phase 1—Dose Escalation:

The initial portion of this protocol will proceed in a phase 1 dose escalation design, with three cohorts of a minimum of 3 patients per cohort. The total number of anti-VEGFR2 engineered cells transferred for each cohort will be: Cohort 1: $10^8$ cells; Cohort 2: $10^9$ cells; Cohort 3: $10^{10}$ cells; and Cohort 4: $5\times10^{10}$ cells.

Prior to receiving the engineered PBL cells, patients will receive a nonmyeloablative lymphocyte depleting preparative regimen of cyclophosphamide and fludarabine followed in one to four days by intravenous infusion of in vitro tumor reactive, CAR gene-transduced PBL plus IV aldesleukin (720,000 IU/kg q8h for a maximum of 15 doses).

Phase 2 Portion

Similar to the Phase 1 portion, prior to receiving the engineered PBL cells, patients in the phase 2 portion will receive a nonmyeloablative lymphocyte depleting preparative regimen of cyclophosphamide and fludarabine followed in one to four days by intravenous infusion of in vitro tumor reactive, CAR gene-transduced PBL plus IV aldesleukin (720,000 IU/kg q8h for a maximum of 15 doses).

The phase 2 portion of the protocol will proceed utilizing the maximum tolerated dose (MTD) of anti-VEGFR2 engineered cells as determined in the phase 1 portion. Patients will be entered into two cohorts based on histology: cohort 1 will include patients with metastatic melanoma and renal cancer and cohort 2 will include all other cancer types.

Drug Administration

Drugs will be administered as set forth in Table 9. Day 0 is the day of cell infusion.

TABLE 9

| Therapy | Day | | | | | | | | | | | |
|---|---|---|---|---|---|---|---|---|---|---|---|---|
| | −7 | −6 | −5 | −4 | −3 | −2 | −1 | 0[1] | 1 | 2 | 3 | 4 |
| 1.0 Cyclophosphamide (60 mg/kg) | X | X | | | | | | | | | | |
| Fludarabine (25 mg/m$^2$) | | | X | X | X | X | X | | | | | |
| Anti-VEGFR2 CAR PBL | | | | | | | | X[1] | | | | |
| Aldesleukin (720,000 IU/kg) | | | | | | | | X[2] | X | X | X | X |
| Filgrastim[3] (5 mcg/kg/day) | | | | | | | | | X | X | X | X |
| trimethoprim and sulfamethoxazole (TMP/SMX)[4] 160 mg/800 mg (example) | X | X | X | X | X | X | X | X | X | X | X | X |
| Fluconazole[5] (400 mg po) | | | | | | | | X | X | X | X | X |
| Valacyclovir po or Acyclovir IV[6] | | | | | | | | X | X | X | X | X |

[1]One to four days after the last dose of fludarabine
[2]Initiate within 24 hours after cell infusion
[3]Continue until neutrophils count >1 × 10$^9$/L for 3 consecutive days or >5 × 10$^9$/L.
[4]The TMP/SMX schedule should be adjusted to QD three times per week (Monday, Wednesday, Friday) and continue for at least six months and until CD4 >200 × 2
[5]Continue until ANC >1000/mm$^3$
[6]In patients positive for herpes simplex virus (HSV) continue until absolute neutrophil count (ANC) is greater than 1000/mm$^3$ Cell Infusion and Aldesleukin Administration Cells are delivered to the patient care unit by a staff member from the Tumor Immunology Cell Processing Laboratory. Prior to infusion, the cell product identity label is double-checked by two authorized staff (medical doctor or registered nurse), an identification of the product and documentation of administration are entered in the patient's chart, as is done for blood banking protocols. The cells are to be infused intravenously over 20-30 minutes via non-filtered tubing, gently agitating the bag during infusion to prevent cell clumping.

Blood Product Support

Using daily CBC's as a guide, the patient will receive platelets and packed red blood cells (PRBC's) as needed. Attempts will be made to keep hemoglobin >8.0 gm/dl, and platelets >20,000/mm3. All blood products with the exception of the stem cell product will be irradiated. Leukocyte filters will be utilized for all blood and platelet transfusions to decrease sensitization to transfused WBC's and decrease the risk of CMV infection.

On-Study Evaluation

Post Cell Infusion Evaluations (No More than 450 mL/6 Weeks)

Once total lymphocyte count is greater than 200/mm$^3$, the following samples will be drawn and sent to the TIL lab on Monday, Wednesday and Friday (while the patient is hospitalized): 5 CPT tubes (10 ml each) and 1 SST tube (10 ml).

At other time points, patient peripheral blood lymphocytes (PBL) will be obtained from whole blood by purification using centrifugation on a Ficoll cushion. Aliquots of these PBMC will be 1) cryopreserved for immunological monitoring of cell function and 2) subjected to DNA and RNA extraction for PCR analysis of CAR and vector copy number estimation.

Biopsies

Biopsies of tumor tissue or lymph nodes may be performed but are not required during the course of therapy. These biopsies will only be performed if minimal morbidity is expected based on the procedure performed and the granulocyte and platelet count. Biopsy tissue will be processed in the Surgery Branch Cell Production Facility in the presence of a Pathology Laboratory pathologist and part of all biopsy tissue will go to the Laboratory of Pathology. Studies will be performed to evaluate the antigen expression by the tumor and to evaluate the reactivity of lymphocytes grown from these biopsies. In addition the presence of transduced cells will be quantitated using RT-PCR for vector sequences.

Immunological Testing:

Apheresis will be performed, prior to and 4-6 weeks after the treatment. At other time points, patient peripheral blood lymphocytes (PBL) will be obtained from whole blood by purification using centrifugation on a Ficoll cushion. Aliquots of these PBMC will be: cryopreserved for immunological monitoring of cell function and subjected to DNA and RNA extraction for PCR analysis of CAR and vector copy number estimation.

Lymphocytes will be tested directly and following in vitro culture. Direct immunological monitoring will quantify T cells reactive with Her-2 by FACS analysis using tetramer staining. Ex vivo immunological assays will include cytokine release by bulk PBL (+/− peptide stimulation) and other experimental studies such as cytolysis if sufficient cells are available. If cell numbers are limiting, preference will be given to the direct analysis of immunological activity. Immunological assays will be standardized by the inclusion of 1) pre-infusion PBMC and 2) an aliquot of the engineered PBL cryopreserved at the time of infusion. In general, differences of 2 to 3 fold in these assays are indicative of true biologic differences. Foxp3 levels will be analyzed by semiquantitative RT-PCR to evaluate for mRNA on PBL samples obtained prior to cell infusion and at the follow up time point.

Monitoring Gene Therapy Trials: Persistence and Replication-Competent Retrovirus (RCR):

Engineered cell survival: CAR and vector presence will be quantitated in PBMC samples using established PCR techniques. Immunological monitoring using both tetramer analysis and staining for the CAR will be used to augment PCR-based analysis. This will provide data to estimate the in vivo survival of lymphocytes derived from the infused cells. In addition, measurement of CD4 and CD8 T-cells will be conducted and studies of these T-cell subsets in the circulation will be determined by using specific PCR assays capable of detecting the unique DNA sequence for each retroviral vector engineered T-cell.

Patient blood samples will be obtained and undergo analysis for detection of RCR by PCR prior to cell infusion and RCR PCR will be performed at 3 and 6 months, and at one year post cell administration. Blood samples will be archived annually thereafter if all previous testing has been negative with a brief clinical history. If a patient dies or develops neoplasms during this trial, efforts will be made to assay a biopsy sample for RCR. If any post-treatment samples are positive, further analysis of the RCR and more extensive patient follow-up will be undertaken, in consultation with the FDA. RCR PCR assays detect the GaLV envelope gene and are performed under contract by the National Gene Vector Laboratory at Indiana University. The results of these tests are maintained by the contractor performing the RCR tests and by the Surgery Branch research team.

Due to nature of these studies, it is possible that expansion of specific T-cell clones will be observed as tumor reactive T-cells proliferating in response to tumor antigens. Therefore, care will be taken to track T-cell persistence both immunologically and molecularly. Blood samples (5-10 mL) for persistence of CAR transduced cells will be obtained 1 month after cell infusion, then at 3, 6, 12 months, and then annually thereafter. If any patient shows a high level of persistence of CAR gene transduced cells at month 6 (by semi quantitative DNA-PCR using primers specific for vector sequences) the previously archived samples will be subjected to techniques that would allow the identification of clonality of persisting CAR gene transduced cells. Such techniques may include T cell cloning or LAM-PCR 30. If a predominant or monoclonal T cell clone derived from CAR gene transduced cells is identified during the follow-up, the integration site and sequence will be identified and subsequently analyzed against human genome database to determine whether the sequences are associated with any known human cancers. If a predominant integration site is observed, the T cell cloning or LAM-PCR test will be used at an interval of no more than three months after the first observation to see if the clone persists or is transient. In all instances where monoclonality is persistent and particularly in instances where there is expansion of the clone, regardless of whether or not the sequence is known to be associated with a known human cancer, the subject should be monitored closely for signs of malignancy, so that treatment, if available, may be initiated early.

Post Study Evaluation (Follow-Up):

Patients will be evaluated 4 to 6 weeks after the initial treatment regimen (defined as the end of the last aldesleukin dose) in accordance with Table 10.

TABLE 10

Physical examination
Chem 20: (Sodium (Na), Potassium (K), Chloride (Cl), Total CO$^2$ (bicarbonate), Creatinine, Glucose, Urea nitrogen (BUN), Albumin, Calcium total, Magnesium total (Mg), Inorganic Phosphorus, Alkaline Phosphatase, ALT/GPT, AST/GOT, Total Bilirubin, Direct Bilirubin, TABLE 10-continued LD, Total Protein, Total CK, Uric Acid), complete blood count and thyroid panel
Toxicity assessment
Computed tomography (CT) of the chest, abdomen and pelvis. This end of course evaluation
will be used to determine tumor response. If clinically indicated, other scans or x-rays may be
performed, e.g. brain magnetic resonance imaging (MRI), bone scan.
Visual symptoms will be evaluated and if changes have occurred from baseline, i.e. changes
in visual acuity, an ophthalmologic consult will be performed.
A 5 liter apheresis will be performed. Subsequently, 60 ml of blood will be obtained at
follow up visits (approximately monthly) for at least 3 months. Peripheral blood mononuclear
cells will be cryopreserved so that immunologic testing may be performed.
Left ventricular ejection fraction (LVEF) evaluation as assessed by either echocardiogram or
Multi Gated Acquisition (MUGA) scan will be conducted at each follow-up evaluation.
If the patient has SD or tumor shrinkage, repeat complete evaluations will be performed
monthly for approximately 3-4 months, and then every 3-4 months until off study criteria are
met.
Detection of RCR and persistence of CAR gene transduced cells:
Long-term follow up of patients receiving gene transfer: Physical examinations will be
performed and documented annually for 5 years following cell infusion to evaluate long-term
safety. After 5 years, health status data will be obtained from surviving patients via
telephone contact or mailed questionnaires. The long term follow up period for retroviral
vectors is 15 years.

Data will be collected and evaluated as detailed below. Evaluation of target lesions will be as follows: All measurable lesions up to a maximum of 10 lesions representative of all involved organs should be identified as target lesions and recorded and measured at baseline. Target lesions should be selected on the basis of their size (lesions with the longest diameter) and their suitability for accurate repetitive measurements (either by imaging techniques or clinically). A sum of the longest diameter (LD) for all target lesions will be calculated and reported as the baseline sum LD. The baseline sum LD will be used as reference to further characterize the objective tumor response of the measurable dimension of the disease. Response criteria for the evaluation of target lesions will be as set forth in Table 11.

TABLE 11

| | |
|---|---|
| Complete Response (CR) | Disappearance of all target lesions |
| Partial Response (PR) | At least a 30% decrease in the sum of the longest diameter (LD) of target lesions taking as reference the baseline sum LD. |
| Progression (PD) | At least a 20% increase in the sum of LD of target lesions taking as reference the smallest sum LD recorded since the treatment started or the appearance of one or more new lesions. |
| Stable Disease (SD) | Neither sufficient shrinkage to qualify for PR nor sufficient increase to qualify for PD taking as references the smallest sum LD. |

Evaluation of non-target lesions will be as follows: All other lesions (or sites of disease) should be identified as non-target lesions and should also be recorded at baseline. Measurements are not required, and these lesions should be followed as "present" or "absent." Response criteria for the evaluation of target lesions will be as set forth in Table 12.

TABLE 12

| | |
|---|---|
| Complete Response (CR) | Disappearance of all non-target lesions and normalization of tumor marker level. |
| Non-Complete Response | Persistence of one or more non-target lesions |
| Progression (PD) | Appearance of one or more new lesions. Unequivocal progression of existing non-target lesions. |

Evaluation of Best Overall Response

The best overall response (Table 13) is the best response recorded from the start of the treatment until disease progression/recurrence (taking as reference for progressive disease the smallest measurements recorded since the treatment started). The patient's best response assignment will depend on the achievement of both measurement and confirmation criteria.

TABLE 13

| Target Lesions | Non-Target Lesions | New Lesions | Overall Response |
|---|---|---|---|
| CR | CR | No | CR |
| CR | Non-CR/Non-PD | No | PR |
| PR | Non-PD | No | PR |
| SD | Non-PD | No | SD |
| PD | Any | Yes or No | PD |
| Any | PD | Yes or No | PD |
| Any | Any | Yes | PD |

Confirmatory Measurement/Duration of Response

Confirmation: To be assigned a status of PR or CR, changes in tumor measurements will be confirmed by repeat studies that should be performed at least 4 weeks after the criteria for response are first met. In the case of SD, follow-up measurements will have met the SD criteria at least once after study entry at a minimum interval of 6-8 weeks.

Duration of Overall Response: The duration of overall response is measured from the time measurement criteria are met for CR/PR (whichever is first recorded) until the first date that recurrent or progressive disease is objectively documented (taking as reference for progressive disease the smallest measurements recorded since the treatment started). The duration of overall complete response is measured from the time measurement criteria are first met for CR until the first date that recurrent disease is objectively documented.

Duration of Stable Disease: Stable disease is measured from the start of the treatment until the criteria for progression are met, taking as reference the smallest measurements recorded since the treatment started.

This example demonstrated a method of administering a population of cells expressing an anti-VEGFR2CAR to human cancer patients.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A nucleic acid comprising a nucleotide sequence encoding a chimeric antigen receptor (CAR) comprising
   (a) an antigen binding domain of a KDR-1121 or DC101 antibody, wherein the antigen binding domain comprises an amino acid sequence comprising SEQ ID NO: 1 or 2;
   (b) an amino acid sequence comprising SEQ ID NO: 3, 4, or 7; and
   (c) an amino acid sequence comprising SEQ ID NO: 5, 6, 8, or 9.

2. The nucleic acid according to claim 1, comprising a nucleotide sequence selected from the group consisting of SEQ ID NOs: 16-21.

3. A recombinant expression vector comprising the nucleic acid of claim 1.

4. An isolated host cell comprising the recombinant expression vector of claim 3.

5. A population of cells comprising at least one host cell of claim 4.

6. A pharmaceutical composition comprising the host cell of claim 4, and a pharmaceutically acceptable carrier.

7. A method of detecting the presence of cancer in a host, the method comprising:
   (a) contacting a sample comprising one or more cells from the host with the host cell of claim 4, thereby forming a complex, and
   (b) detecting the complex, wherein detection of the complex is indicative of the presence of cancer in the host, wherein
      (i) the host is a human and the CAR comprises SEQ ID NO: 1, or
      (ii) the host is a mouse and the CAR comprises SEQ ID NO: 2.

8. The nucleic acid according to claim 1, wherein the antigen binding domain comprises an amino acid sequence comprising SEQ ID NO: 1.

9. The nucleic acid according to claim 1, comprising a nucleotide sequence encoding
    (a) SEQ ID NOs: 1, 3, and 5;
    (b) SEQ ID NOs: 1, 7, and 8;
    (c) SEQ ID NOs: 2, 4, and 6;
    (d) SEQ ID NOs: 2, 4, and 9;
    (e) SEQ ID NOs: 2, 3, and 5; or
    (f) SEQ ID NOs: 2, 7, and 8.

10. The nucleic acid according to claim 1, comprising a nucleotide sequence encoding an amino acid sequence selected from the group consisting of SEQ ID NOs: 10-15.

11. A host cell comprising a recombinant expression vector comprising the nucleic acid of claim 2.

12. The nucleic acid of claim 1 comprising a nucleotide sequence encoding a CAR comprising
    (a) an antigen binding domain of a KDR-1121 antibody, wherein the antigen binding domain comprises an amino acid sequence comprising SEQ ID NO: 1;
    (b) an amino acid sequence comprising SEQ ID NO: 3 or 7; and
    (c) an amino acid sequence comprising SEQ ID NO: 5 or 8.

13. The nucleic acid of claim 9 comprising a nucleotide sequence encoding
    (a) SEQ ID NOs: 1, 3, and 5; or
    (b) SEQ ID NOs: 1, 7, and 8.

14. The nucleic acid of claim 2 comprising SEQ ID NO: 16 or 17.

15. The nucleic acid of claim 10 comprising a nucleotide sequence encoding SEQ ID NO: 10 or 11.

16. A host cell comprising a recombinant expression vector comprising the nucleic acid of claim 10.

17. A host cell comprising a recombinant expression vector comprising the nucleic acid of claim 12.

18. A host cell comprising a recombinant expression vector comprising the nucleic acid of claim 14.

19. A host cell comprising a recombinant expression vector comprising the nucleic acid of claim 15.

* * * * *

SEQUENCE LISTING

```
<160> NUMBER OF SEQ ID NOS: 72

<210> SEQ ID NO 1
<211> LENGTH: 260
<212> TYPE: PRT
<213> ORGANISM: Artificial Sequence
<220> FEATURE:
<223> OTHER INFORMATION: Synthetic

<400> SEQUENCE: 1

Met Asp Phe Gln Val Gln Ile Phe Ser Phe Leu Leu Ile Ser Ala Ser
1               5                   10                  15

Val Ile Met Ser Arg Gly Asp Ile Gln Met Thr Gln Ser Pro Ser Ser
            20                  25                  30

Val Ser Ala Ser Ile Gly Asp Arg Val Thr Ile Thr Cys Arg Ala Ser
        35                  40                  45

Gln Gly Ile Asp Asn Trp Leu Gly Trp Tyr Gln Gln Lys Pro Gly Lys
    50                  55                  60

Ala Pro Lys Leu Leu Ile Tyr Asp Ala Ser Asn Leu Asp Thr Gly Val
65                  70                  75                  80

Pro Ser Arg Phe Ser Gly Ser Gly Ser Gly Thr Tyr Phe Thr Leu Thr
                85                  90                  95

Ile Ser Ser Leu Gln Ala Glu Asp Phe Ala Val Tyr Phe Cys Gln Gln
            100                 105                 110

Ala Lys Ala Phe Pro Pro Thr Phe Gly Gly Gly Thr Lys Val Asp Ile
        115                 120                 125

Lys Gly Ser Thr Ser Gly Ser Gly Lys Pro Gly Ser Gly Glu Gly Ser
    130                 135                 140

Glu Val Gln Leu Val Gln Ser Gly Gly Gly Leu Val Lys Pro Gly Gly
145                 150                 155                 160

Ser Leu Arg Leu Ser Cys Ala Ala Ser Gly Phe Thr Phe Ser Ser Tyr
                165                 170                 175

Ser Met Asn Trp Val Arg Gln Ala Pro Gly Lys Gly Leu Glu Trp Val
            180                 185                 190

Ser Ser Ile Ser Ser Ser Ser Tyr Ile Tyr Tyr Ala Asp Ser Val
        195                 200                 205

Lys Gly Arg Phe Thr Ile Ser Arg Asp Asn Ala Lys Asn Ser Leu Tyr
    210                 215                 220
```

```
Leu Gln Met Asn Ser Leu Arg Ala Glu Asp Thr Ala Val Tyr Tyr Cys
225                 230                 235                 240

Ala Arg Val Thr Asp Ala Phe Asp Ile Trp Gly Gln Gly Thr Met Val
                245                 250                 255

Thr Val Ser Ser
            260

<210> SEQ ID NO 2
<211> LENGTH: 265
<212> TYPE: PRT
<213> ORGANISM: Artificial Sequence
<220> FEATURE:
<223> OTHER INFORMATION: Synthetic

<400> SEQUENCE: 2

Met Gly Trp Ser Cys Ile Ile Leu Phe Leu Val Ala Thr Ala Thr Gly
1               5                   10                  15

Val His Ser Glu Val Gln Leu Val Glu Thr Gly Gly Gly Leu Val Gln
            20                  25                  30

Pro Gly Asn Ser Leu Lys Leu Ser Cys Ala Thr Ser Gly Phe Ile Phe
        35                  40                  45

Ser Thr Thr Trp Met Asn Trp Ile Arg Gln Thr Pro Gly Lys Arg Leu
50                  55                  60

Glu Trp Leu Ala Gln Ile Glu Asp Lys Ser Asn Asn Tyr Phe Ile Ser
65                  70                  75                  80

Tyr Ser Glu Ser Val Lys Gly Arg Phe Thr Ile Ser Arg Asp Asp Ser
                85                  90                  95

Lys Ser Ser Val Tyr Leu Gln Met Asn Asn Leu Lys Glu Glu Asp Thr
            100                 105                 110

Ala Ile Tyr Tyr Cys Ser Trp Lys Tyr Arg Ser Asn Tyr Tyr Phe Asp
        115                 120                 125

Tyr Trp Gly Gln Gly Val Met Val Thr Val Ser Ser Gly Ser Thr Ser
130                 135                 140

Gly Ser Gly Lys Pro Gly Ser Gly Glu Gly Ser Asp Ile Val Leu Thr
145                 150                 155                 160

Gln Ser Pro Ala Leu Ala Val Ser Leu Glu Gln Arg Ala Thr Ile Ser
                165                 170                 175

Cys Lys Thr Ser Gln Asn Val Asp Tyr Tyr Gly Ile Ser Tyr Leu His
            180                 185                 190

Trp Tyr Gln Gln Lys Pro Gly Gln Gln Pro Lys Leu Leu Ile Tyr Glu
        195                 200                 205

Gly Ser Asn Leu Ala Ser Gly Ile Pro Ala Arg Phe Ser Gly Ser Gly
210                 215                 220

Ser Gly Thr Asp Phe Thr Leu Thr Ile Asp Pro Val Glu Ala Asp Asp
225                 230                 235                 240

Ile Val Thr Tyr Tyr Cys Gln Gln Ser Lys Asp Tyr Pro Tyr Thr Phe
                245                 250                 255

Gly Ala Gly Thr Lys Leu Glu Leu Lys
            260                 265

<210> SEQ ID NO 3
<211> LENGTH: 83
<212> TYPE: PRT
<213> ORGANISM: Homo sapiens

<400> SEQUENCE: 3
```

-continued

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
            35                  40                  45

Gly Leu Asp Phe Ala Cys Asp Ile Tyr Ile Trp Ala Pro Leu Ala Gly
        50                  55                  60

Thr Cys Gly Val Leu Leu Leu Ser Leu Val Ile Thr Leu Tyr Cys Asn
65                  70                  75                  80

His Arg Asn

<210> SEQ ID NO 4
<211> LENGTH: 72
<212> TYPE: PRT
<213> ORGANISM: Mus musculus

<400> SEQUENCE: 4

Thr Thr Thr Lys Pro Val Leu Arg Thr Pro Ser Val His Pro Thr
1               5                   10                  15

Gly Thr Ser Gln Pro Gln Arg Pro Glu Asp Cys Arg Pro Arg Gly Ser
            20                  25                  30

Val Lys Gly Thr Gly Leu Asp Phe Ala Cys Asp Ile Tyr Ile Trp Ala
        35                  40                  45

Pro Leu Ala Gly Ile Cys Val Ala Leu Leu Leu Ser Leu Ile Ile Thr
    50                  55                  60

Leu Ile Cys Tyr His Arg Ser Arg
65                  70

<210> SEQ ID NO 5
<211> LENGTH: 200
<212> TYPE: PRT
<213> ORGANISM: Artificial Sequence
<220> FEATURE:
<223> OTHER INFORMATION: Synthetic

<400> SEQUENCE: 5

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Phe Ser Val Val Lys Arg
            35                  40                  45

Gly Arg Lys Lys Leu Leu Tyr Ile Phe Lys Gln Pro Phe Met Arg Pro
        50                  55                  60

Val Gln Thr Thr Gln Glu Asp Gly Cys Ser Cys Arg Phe Pro Glu
65                  70                  75                  80

Glu Glu Glu Gly Gly Cys Glu Leu Arg Val Lys Phe Ser Arg Ser Ala
                85                  90                  95

Asp Ala Pro Ala Tyr Gln Gln Gly Gln Asn Gln Leu Tyr Asn Glu Leu
            100                 105                 110

Asn Leu Gly Arg Arg Glu Glu Tyr Asp Val Leu Asp Lys Arg Arg Gly
        115                 120                 125

Arg Asp Pro Glu Met Gly Gly Lys Pro Arg Arg Lys Asn Pro Gln Glu
    130                 135                 140

Gly Leu Tyr Asn Glu Leu Gln Lys Asp Lys Met Ala Glu Ala Tyr Ser
145                 150                 155                 160

Glu Ile Gly Met Lys Gly Glu Arg Arg Gly Lys Gly His Asp Gly
                165                 170                 175

Leu Tyr Gln Gly Leu Ser Thr Ala Thr Lys Asp Thr Tyr Asp Ala Leu
            180                 185                 190

His Met Gln Ala Leu Pro Pro Arg
        195                 200

<210> SEQ ID NO 6
<211> LENGTH: 199
<212> TYPE: PRT
<213> ORGANISM: Artificial Sequence
<220> FEATURE:
<223> OTHER INFORMATION: Synthetic

<400> SEQUENCE: 6

Asn Ser Arg Arg Asn Arg Leu Leu Gln Val Thr Thr Met Asn Met Thr
1               5                   10                  15

Pro Arg Arg Pro Gly Leu Thr Arg Lys Pro Tyr Gln Pro Tyr Ala Pro
            20                  25                  30

Ala Arg Asp Phe Ala Ala Tyr Arg Pro Lys Trp Ile Arg Lys Lys Phe
        35                  40                  45

Pro His Ile Phe Lys Gln Pro Phe Lys Lys Thr Thr Gly Ala Ala Gln
    50                  55                  60

Glu Glu Asp Ala Cys Ser Cys Arg Cys Pro Gln Glu Glu Glu Gly Gly
65                  70                  75                  80

Gly Gly Gly Tyr Glu Leu Arg Ala Lys Phe Ser Arg Ser Ala Glu Thr
                85                  90                  95

Ala Ala Asn Leu Gln Asp Pro Asn Gln Leu Tyr Asn Glu Leu Asn Leu
            100                 105                 110

Gly Arg Arg Glu Glu Tyr Asp Val Leu Glu Lys Lys Arg Ala Arg Asp
        115                 120                 125

Pro Glu Met Gly Gly Lys Gln Gln Arg Arg Arg Asn Pro Gln Glu Gly
    130                 135                 140

Val Tyr Asn Ala Leu Gln Lys Asp Lys Met Ala Glu Ala Tyr Ser Glu
145                 150                 155                 160

Ile Gly Thr Lys Gly Glu Arg Arg Gly Lys Gly His Asp Gly Leu
                165                 170                 175

Tyr Gln Gly Leu Ser Thr Ala Thr Lys Asp Thr Tyr Asp Ala Leu His
            180                 185                 190

Met Gln Thr Leu Ala Pro Arg
        195

<210> SEQ ID NO 7
<211> LENGTH: 106
<212> TYPE: PRT
<213> ORGANISM: Homo sapiens

<400> SEQUENCE: 7

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

```
Trp Arg Ser Lys Arg Ser Arg Leu Leu His Ser Asp Tyr Met Asn Met
 65                  70                  75                  80

Thr Pro Arg Arg Pro Gly Pro Thr Arg Lys His Tyr Gln Pro Tyr Ala
                 85                  90                  95

Pro Pro Arg Asp Phe Ala Ala Tyr Arg Ser
            100                 105

<210> SEQ ID NO 8
<211> LENGTH: 112
<212> TYPE: PRT
<213> ORGANISM: Homo sapiens

<400> SEQUENCE: 8

Arg Val Lys Phe Ser Arg Ser Ala Asp Ala Pro Ala Tyr Gln Gln Gly
  1               5                  10                  15

Gln Asn Gln Leu Tyr Asn Glu Leu Asn Leu Gly Arg Arg Glu Glu Tyr
                 20                  25                  30

Asp Val Leu Asp Lys Arg Arg Gly Arg Asp Pro Glu Met Gly Gly Lys
             35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110

<210> SEQ ID NO 9
<211> LENGTH: 154
<212> TYPE: PRT
<213> ORGANISM: Artificial Sequence
<220> FEATURE:
<223> OTHER INFORMATION: Synthetic

<400> SEQUENCE: 9

Asn Ser Arg Arg Asn Arg Leu Leu Gln Val Thr Thr Met Asn Met Thr
  1               5                  10                  15

Pro Arg Arg Pro Gly Leu Thr Arg Lys Pro Tyr Gln Pro Tyr Ala Pro
                 20                  25                  30

Ala Arg Asp Phe Ala Ala Tyr Arg Pro Arg Ala Lys Phe Ser Arg Ser
             35                  40                  45

Ala Glu Thr Ala Ala Asn Leu Gln Asp Pro Asn Gln Leu Tyr Asn Glu
 50                  55                  60

Leu Asn Leu Gly Arg Arg Glu Glu Tyr Asp Val Leu Glu Lys Lys Arg
 65                  70                  75                  80

Ala Arg Asp Pro Glu Met Gly Gly Lys Gln Gln Arg Arg Asn Pro
                 85                  90                  95

Gln Glu Gly Val Tyr Asn Ala Leu Gln Lys Asp Lys Met Ala Glu Ala
                100                 105                 110

Tyr Ser Glu Ile Gly Thr Lys Gly Glu Arg Arg Gly Lys Gly His
                115                 120                 125

Asp Gly Leu Tyr Gln Gly Leu Ser Thr Ala Thr Lys Asp Thr Tyr Asp
            130                 135                 140

Ala Leu His Met Gln Thr Leu Ala Pro Arg
145                 150
```

<210> SEQ ID NO 10
<211> LENGTH: 546
<212> TYPE: PRT
<213> ORGANISM: Artificial Sequence
<220> FEATURE:
<223> OTHER INFORMATION: Synthetic

<400> SEQUENCE: 10

```
Met Asp Phe Gln Val Gln Ile Phe Ser Phe Leu Leu Ile Ser Ala Ser
1               5                   10                  15

Val Ile Met Ser Arg Gly Asp Ile Gln Met Thr Gln Ser Pro Ser Ser
            20                  25                  30

Val Ser Ala Ser Ile Gly Asp Arg Val Thr Ile Thr Cys Arg Ala Ser
        35                  40                  45

Gln Gly Ile Asp Asn Trp Leu Gly Trp Tyr Gln Gln Lys Pro Gly Lys
    50                  55                  60

Ala Pro Lys Leu Leu Ile Tyr Asp Ala Ser Asn Leu Asp Thr Gly Val
65                  70                  75                  80

Pro Ser Arg Phe Ser Gly Ser Gly Ser Gly Thr Tyr Phe Thr Leu Thr
                85                  90                  95

Ile Ser Ser Leu Gln Ala Glu Asp Phe Ala Val Tyr Phe Cys Gln Gln
            100                 105                 110

Ala Lys Ala Phe Pro Pro Thr Phe Gly Gly Gly Thr Lys Val Asp Ile
        115                 120                 125

Lys Gly Ser Thr Ser Gly Ser Gly Lys Pro Gly Ser Gly Glu Gly Ser
    130                 135                 140

Glu Val Gln Leu Val Gln Ser Gly Gly Gly Leu Val Lys Pro Gly Gly
145                 150                 155                 160

Ser Leu Arg Leu Ser Cys Ala Ala Ser Gly Phe Thr Phe Ser Ser Tyr
                165                 170                 175

Ser Met Asn Trp Val Arg Gln Ala Pro Gly Lys Gly Leu Glu Trp Val
            180                 185                 190

Ser Ser Ile Ser Ser Ser Ser Tyr Ile Tyr Tyr Ala Asp Ser Val
        195                 200                 205

Lys Gly Arg Phe Thr Ile Ser Arg Asp Asn Ala Lys Asn Ser Leu Tyr
    210                 215                 220

Leu Gln Met Asn Ser Leu Arg Ala Glu Asp Thr Ala Val Tyr Tyr Cys
225                 230                 235                 240

Ala Arg Val Thr Asp Ala Phe Asp Ile Trp Gly Gln Gly Thr Met Val
                245                 250                 255

Thr Val Ser Ser Ala Ala Ala Phe Val Pro Val Phe Leu Pro Ala Lys
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn His Arg Asn Arg Ser Lys Arg Ser Arg
            340                 345                 350

Leu Leu His Ser Asp Tyr Met Asn Met Thr Pro Arg Arg Pro Gly Pro
        355                 360                 365

Thr Arg Lys His Tyr Gln Pro Tyr Ala Pro Pro Arg Asp Phe Ala Ala
```

```
                370                 375                 380
Tyr Arg Ser Arg Phe Ser Val Val Lys Arg Gly Arg Lys Lys Leu Leu
385                 390                 395                 400

Tyr Ile Phe Lys Gln Pro Phe Met Arg Pro Val Gln Thr Thr Gln Glu
                405                 410                 415

Glu Asp Gly Cys Ser Cys Arg Phe Pro Glu Glu Glu Glu Gly Gly Cys
                420                 425                 430

Glu Leu Arg Val Lys Phe Ser Arg Ser Ala Asp Ala Pro Ala Tyr Gln
                435                 440                 445

Gln Gly Gln Asn Gln Leu Tyr Asn Glu Leu Asn Leu Gly Arg Arg Glu
                450                 455                 460

Glu Tyr Asp Val Leu Asp Lys Arg Arg Gly Arg Asp Pro Glu Met Gly
465                 470                 475                 480

Gly Lys Pro Arg Arg Lys Asn Pro Gln Glu Gly Leu Tyr Asn Glu Leu
                485                 490                 495

Gln Lys Asp Lys Met Ala Glu Ala Tyr Ser Glu Ile Gly Met Lys Gly
                500                 505                 510

Glu Arg Arg Arg Gly Lys Gly His Asp Gly Leu Tyr Gln Gly Leu Ser
                515                 520                 525

Thr Ala Thr Lys Asp Thr Tyr Asp Ala Leu His Met Gln Ala Leu Pro
                530                 535                 540

Pro Arg
545

<210> SEQ ID NO 11
<211> LENGTH: 481
<212> TYPE: PRT
<213> ORGANISM: Artificial Sequence
<220> FEATURE:
<223> OTHER INFORMATION: Synthetic

<400> SEQUENCE: 11

Met Asp Phe Gln Val Gln Ile Phe Ser Phe Leu Leu Ile Ser Ala Ser
1               5                   10                  15

Val Ile Met Ser Arg Gly Asp Ile Gln Met Thr Gln Ser Pro Ser Ser
                20                  25                  30

Val Ser Ala Ser Ile Gly Asp Arg Val Thr Ile Thr Cys Arg Ala Ser
                35                  40                  45

Gln Gly Ile Asp Asn Trp Leu Gly Trp Tyr Gln Gln Lys Pro Gly Lys
                50                  55                  60

Ala Pro Lys Leu Leu Ile Tyr Asp Ala Ser Asn Leu Asp Thr Gly Val
65                  70                  75                  80

Pro Ser Arg Phe Ser Gly Ser Gly Ser Gly Thr Tyr Phe Thr Leu Thr
                85                  90                  95

Ile Ser Ser Leu Gln Ala Glu Asp Phe Ala Val Tyr Phe Cys Gln Gln
                100                 105                 110

Ala Lys Ala Phe Pro Pro Thr Phe Gly Gly Gly Thr Lys Val Asp Ile
                115                 120                 125

Lys Gly Ser Thr Ser Gly Ser Gly Lys Pro Gly Ser Gly Glu Gly Ser
                130                 135                 140

Glu Val Gln Leu Val Gln Ser Gly Gly Gly Leu Val Lys Pro Gly Gly
145                 150                 155                 160

Ser Leu Arg Leu Ser Cys Ala Ala Ser Gly Phe Thr Phe Ser Ser Tyr
                165                 170                 175

Ser Met Asn Trp Val Arg Gln Ala Pro Gly Lys Gly Leu Glu Trp Val
```

```
                    180                 185                 190
Ser Ser Ile Ser Ser Ser Ser Tyr Ile Tyr Tyr Ala Asp Ser Val
            195                 200                 205

Lys Gly Arg Phe Thr Ile Ser Arg Asp Asn Ala Lys Asn Ser Leu Tyr
210                 215                 220

Leu Gln Met Asn Ser Leu Arg Ala Glu Asp Thr Ala Val Tyr Tyr Cys
225                 230                 235                 240

Ala Arg Val Thr Asp Ala Phe Asp Ile Trp Gly Gln Gly Thr Met Val
                245                 250                 255

Thr Val Ser Ser Ala Ala Ile Glu Val Met Tyr Pro Pro Pro Tyr
            260                 265                 270

Leu Asp Asn Glu Lys Ser Asn Gly Thr Ile Ile His Val Lys Gly Lys
            275                 280                 285

His Leu Cys Pro Ser Pro Leu Phe Pro Gly Pro Ser Lys Pro Phe Trp
        290                 295                 300

Val Leu Val Val Val Gly Gly Val Leu Ala Cys Tyr Ser Leu Leu Val
305                 310                 315                 320

Thr Val Ala Phe Ile Ile Phe Trp Arg Ser Lys Arg Ser Arg Leu Leu
                325                 330                 335

His Ser Asp Tyr Met Asn Met Thr Pro Arg Arg Pro Gly Pro Thr Arg
                340                 345                 350

Lys His Tyr Gln Pro Tyr Ala Pro Pro Arg Asp Phe Ala Ala Tyr Arg
            355                 360                 365

Ser Arg Val Lys Phe Ser Arg Ser Ala Asp Ala Pro Ala Tyr Gln Gln
        370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg

<210> SEQ ID NO 12
<211> LENGTH: 539
<212> TYPE: PRT
<213> ORGANISM: Artificial Sequence
<220> FEATURE:
<223> OTHER INFORMATION: Synthetic

<400> SEQUENCE: 12

Met Gly Trp Ser Cys Ile Ile Leu Phe Leu Val Ala Thr Ala Thr Gly
1               5                   10                  15

Val His Ser Glu Val Gln Leu Val Glu Thr Gly Gly Gly Leu Val Gln
                20                  25                  30

Pro Gly Asn Ser Leu Lys Leu Ser Cys Ala Thr Ser Gly Phe Ile Phe
            35                  40                  45

Ser Thr Thr Trp Met Asn Trp Ile Arg Gln Thr Pro Gly Lys Arg Leu
        50                  55                  60
```

```
Glu Trp Leu Ala Gln Ile Glu Asp Lys Ser Asn Asn Tyr Phe Ile Ser
 65                  70                  75                  80

Tyr Ser Glu Ser Val Lys Gly Arg Phe Thr Ile Ser Arg Asp Asp Ser
                 85                  90                  95

Lys Ser Ser Val Tyr Leu Gln Met Asn Asn Leu Lys Glu Glu Asp Thr
            100                 105                 110

Ala Ile Tyr Tyr Cys Ser Trp Lys Tyr Arg Ser Asn Tyr Tyr Phe Asp
        115                 120                 125

Tyr Trp Gly Gln Gly Val Met Val Thr Val Ser Ser Gly Ser Thr Ser
    130                 135                 140

Gly Ser Gly Lys Pro Gly Ser Gly Glu Gly Ser Asp Ile Val Leu Thr
145                 150                 155                 160

Gln Ser Pro Ala Leu Ala Val Ser Leu Glu Gln Arg Ala Thr Ile Ser
                165                 170                 175

Cys Lys Thr Ser Gln Asn Val Asp Tyr Tyr Gly Ile Ser Tyr Leu His
            180                 185                 190

Trp Tyr Gln Gln Lys Pro Gly Gln Gln Pro Lys Leu Leu Ile Tyr Glu
        195                 200                 205

Gly Ser Asn Leu Ala Ser Gly Ile Pro Ala Arg Phe Ser Gly Ser Gly
    210                 215                 220

Ser Gly Thr Asp Phe Thr Leu Thr Ile Asp Pro Val Glu Ala Asp Asp
225                 230                 235                 240

Ile Val Thr Tyr Tyr Cys Gln Gln Ser Lys Asp Tyr Pro Tyr Thr Phe
                245                 250                 255

Gly Ala Gly Thr Lys Leu Glu Leu Lys Ala Ala Ala Thr Thr Thr Lys
            260                 265                 270

Pro Val Leu Arg Thr Pro Ser Pro Val His Pro Thr Gly Thr Ser Gln
        275                 280                 285

Pro Gln Arg Pro Glu Asp Cys Arg Pro Arg Gly Ser Val Lys Gly Thr
    290                 295                 300

Gly Leu Asp Phe Ala Cys Asp Ile Tyr Ile Trp Ala Pro Leu Ala Gly
305                 310                 315                 320

Ile Cys Val Ala Leu Leu Leu Ser Leu Ile Ile Thr Leu Ile Cys Tyr
                325                 330                 335

His Arg Ser Arg Asn Ser Arg Arg Asn Arg Leu Leu Gln Val Thr Thr
            340                 345                 350

Met Asn Met Thr Pro Arg Arg Pro Gly Leu Thr Arg Lys Pro Tyr Gln
        355                 360                 365

Pro Tyr Ala Pro Ala Arg Asp Phe Ala Ala Tyr Arg Pro Lys Trp Ile
    370                 375                 380

Arg Lys Lys Phe Pro His Ile Phe Lys Gln Pro Phe Lys Lys Thr Thr
385                 390                 395                 400

Gly Ala Ala Gln Glu Glu Asp Ala Cys Ser Cys Arg Cys Pro Gln Glu
                405                 410                 415

Glu Glu Gly Gly Gly Gly Gly Tyr Glu Leu Arg Ala Lys Phe Ser Arg
            420                 425                 430

Ser Ala Glu Thr Ala Ala Asn Leu Gln Asp Pro Asn Gln Leu Tyr Asn
        435                 440                 445

Glu Leu Asn Leu Gly Arg Arg Glu Glu Tyr Asp Val Leu Glu Lys Lys
    450                 455                 460

Arg Ala Arg Asp Pro Glu Met Gly Gly Lys Gln Gln Arg Arg Arg Asn
465                 470                 475                 480
```

```
Pro Gln Glu Gly Val Tyr Asn Ala Leu Gln Lys Asp Lys Met Ala Glu
                485                 490                 495

Ala Tyr Ser Glu Ile Gly Thr Lys Gly Glu Arg Arg Arg Gly Lys Gly
            500                 505                 510

His Asp Gly Leu Tyr Gln Gly Leu Ser Thr Ala Thr Lys Asp Thr Tyr
        515                 520                 525

Asp Ala Leu His Met Gln Thr Leu Ala Pro Arg
    530                 535

<210> SEQ ID NO 13
<211> LENGTH: 494
<212> TYPE: PRT
<213> ORGANISM: Artificial Sequence
<220> FEATURE:
<223> OTHER INFORMATION: Synthetic

<400> SEQUENCE: 13

Met Gly Trp Ser Cys Ile Ile Leu Phe Leu Val Ala Thr Ala Thr Gly
1               5                   10                  15

Val His Ser Glu Val Gln Leu Val Glu Thr Gly Gly Gly Leu Val Gln
            20                  25                  30

Pro Gly Asn Ser Leu Lys Leu Ser Cys Ala Thr Ser Gly Phe Ile Phe
        35                  40                  45

Ser Thr Thr Trp Met Asn Trp Ile Arg Gln Pro Gly Lys Arg Leu
50                  55                  60

Glu Trp Leu Ala Gln Ile Glu Asp Lys Ser Asn Asn Tyr Phe Ile Ser
65                  70                  75                  80

Tyr Ser Glu Ser Val Lys Gly Arg Phe Thr Ile Ser Arg Asp Asp Ser
                85                  90                  95

Lys Ser Ser Val Tyr Leu Gln Met Asn Asn Leu Lys Glu Glu Asp Thr
            100                 105                 110

Ala Ile Tyr Tyr Cys Ser Trp Lys Tyr Arg Ser Asn Tyr Tyr Phe Asp
        115                 120                 125

Tyr Trp Gly Gln Gly Val Met Val Thr Val Ser Ser Gly Ser Thr Ser
    130                 135                 140

Gly Ser Gly Lys Pro Gly Ser Gly Glu Gly Ser Asp Ile Val Leu Thr
145                 150                 155                 160

Gln Ser Pro Ala Leu Ala Val Ser Leu Glu Gln Arg Ala Thr Ile Ser
                165                 170                 175

Cys Lys Thr Ser Gln Asn Val Asp Tyr Tyr Gly Ile Ser Tyr Leu His
            180                 185                 190

Trp Tyr Gln Gln Lys Pro Gly Gln Pro Lys Leu Leu Ile Tyr Glu
        195                 200                 205

Gly Ser Asn Leu Ala Ser Gly Ile Pro Ala Arg Phe Ser Gly Ser Gly
    210                 215                 220

Ser Gly Thr Asp Phe Thr Leu Thr Ile Asp Pro Val Glu Ala Asp Asp
225                 230                 235                 240

Ile Val Thr Tyr Tyr Cys Gln Gln Ser Lys Asp Tyr Pro Tyr Thr Phe
                245                 250                 255

Gly Ala Gly Thr Lys Leu Glu Leu Lys Ala Ala Ala Thr Thr Thr Lys
            260                 265                 270

Pro Val Leu Arg Thr Pro Ser Pro Val His Pro Thr Gly Thr Ser Gln
        275                 280                 285

Pro Gln Arg Pro Glu Asp Cys Arg Pro Arg Gly Ser Val Lys Gly Thr
    290                 295                 300
```

```
Gly Leu Asp Phe Ala Cys Asp Ile Tyr Ile Trp Ala Pro Leu Ala Gly
305                 310                 315                 320

Ile Cys Val Ala Leu Leu Leu Ser Leu Ile Ile Thr Leu Ile Cys Tyr
            325                 330                 335

His Arg Ser Arg Asn Ser Arg Arg Asn Arg Leu Leu Gln Val Thr Thr
        340                 345                 350

Met Asn Met Thr Pro Arg Arg Pro Gly Leu Thr Arg Lys Pro Tyr Gln
    355                 360                 365

Pro Tyr Ala Pro Ala Arg Asp Phe Ala Ala Tyr Arg Pro Arg Ala Lys
370                 375                 380

Phe Ser Arg Ser Ala Glu Thr Ala Ala Asn Leu Gln Asp Pro Asn Gln
385                 390                 395                 400

Leu Tyr Asn Glu Leu Asn Leu Gly Arg Arg Glu Glu Tyr Asp Val Leu
                405                 410                 415

Glu Lys Lys Arg Ala Arg Asp Pro Glu Met Gly Gly Lys Gln Gln Arg
            420                 425                 430

Arg Arg Asn Pro Gln Glu Gly Val Tyr Asn Ala Leu Gln Lys Asp Lys
        435                 440                 445

Met Ala Glu Ala Tyr Ser Glu Ile Gly Thr Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Thr Leu Ala Pro Arg
                485                 490
```

<210> SEQ ID NO 14
<211> LENGTH: 551
<212> TYPE: PRT
<213> ORGANISM: Artificial Sequence
<220> FEATURE:
<223> OTHER INFORMATION: Synthetic

<400> SEQUENCE: 14

```
Met Gly Trp Ser Cys Ile Ile Leu Phe Leu Val Ala Thr Ala Thr Gly
1               5                   10                  15

Val His Ser Glu Val Gln Leu Val Glu Thr Gly Gly Gly Leu Val Gln
            20                  25                  30

Pro Gly Asn Ser Leu Lys Leu Ser Cys Ala Thr Ser Gly Phe Ile Phe
        35                  40                  45

Ser Thr Thr Trp Met Asn Trp Ile Arg Gln Thr Pro Gly Lys Arg Leu
    50                  55                  60

Glu Trp Leu Ala Gln Ile Glu Asp Lys Ser Asn Asn Tyr Phe Ile Ser
65                  70                  75                  80

Tyr Ser Glu Ser Val Lys Gly Arg Phe Thr Ile Ser Arg Asp Asp Ser
                85                  90                  95

Lys Ser Ser Val Tyr Leu Gln Met Asn Asn Leu Lys Glu Glu Asp Thr
            100                 105                 110

Ala Ile Tyr Tyr Cys Ser Trp Lys Tyr Arg Ser Asn Tyr Phe Asp
        115                 120                 125

Tyr Trp Gly Gln Gly Val Met Val Thr Val Ser Ser Gly Ser Thr Ser
130                 135                 140

Gly Ser Gly Lys Pro Gly Ser Gly Glu Gly Ser Asp Ile Val Leu Thr
145                 150                 155                 160

Gln Ser Pro Ala Leu Ala Val Ser Leu Glu Gln Arg Ala Thr Ile Ser
                165                 170                 175
```

```
Cys Lys Thr Ser Gln Asn Val Asp Tyr Tyr Gly Ile Ser Tyr Leu His
            180                 185                 190

Trp Tyr Gln Gln Lys Pro Gly Gln Gln Pro Lys Leu Leu Ile Tyr Glu
        195                 200                 205

Gly Ser Asn Leu Ala Ser Gly Ile Pro Ala Arg Phe Ser Gly Ser Gly
        210                 215                 220

Ser Gly Thr Asp Phe Thr Leu Thr Ile Asp Pro Val Glu Ala Asp Asp
225                 230                 235                 240

Ile Val Thr Tyr Tyr Cys Gln Gln Ser Lys Asp Tyr Pro Tyr Thr Phe
                245                 250                 255

Gly Ala Gly Thr Lys Leu Glu Leu Lys Ala Ala Phe Val Pro Val
            260                 265                 270

Phe Leu Pro Ala Lys Pro Thr Thr Thr Pro Ala Pro Arg Pro Pro Thr
        275                 280                 285

Pro Ala Pro Thr Ile Ala Ser Gln Pro Leu Ser Leu Arg Pro Glu Ala
        290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Asn His Arg Asn Arg
            340                 345                 350

Ser Lys Arg Ser Arg Leu Leu His Ser Asp Tyr Met Asn Met Thr Pro
        355                 360                 365

Arg Arg Pro Gly Pro Thr Arg Lys His Tyr Gln Pro Tyr Ala Pro Pro
370                 375                 380

Arg Asp Phe Ala Ala Tyr Arg Ser Arg Phe Ser Val Val Lys Arg Gly
385                 390                 395                 400

Arg Lys Lys Leu Leu Tyr Ile Phe Lys Gln Pro Phe Met Arg Pro Val
                405                 410                 415

Gln Thr Thr Gln Glu Glu Asp Gly Cys Ser Cys Arg Phe Pro Glu Glu
            420                 425                 430

Glu Glu Gly Gly Cys Glu Leu Arg Val Lys Phe Ser Arg Ser Ala Asp
        435                 440                 445

Ala Pro Ala Tyr Gln Gln Gly Gln Asn Gln Leu Tyr Asn Glu Leu Asn
450                 455                 460

Leu Gly Arg Arg Glu Glu Tyr Asp Val Leu Asp Lys Arg Arg Gly Arg
465                 470                 475                 480

Asp Pro Glu Met Gly Gly Lys Pro Arg Arg Lys Asn Pro Gln Glu Gly
                485                 490                 495

Leu Tyr Asn Glu Leu Gln Lys Asp Lys Met Ala Glu Ala Tyr Ser Glu
            500                 505                 510

Ile Gly Met Lys Gly Glu Arg Arg Arg Gly Lys Gly His Asp Gly Leu
        515                 520                 525

Tyr Gln Gly Leu Ser Thr Ala Thr Lys Asp Thr Tyr Asp Ala Leu His
530                 535                 540

Met Gln Ala Leu Pro Pro Arg
545                 550

<210> SEQ ID NO 15
<211> LENGTH: 487
<212> TYPE: PRT
<213> ORGANISM: Artificial Sequence
<220> FEATURE:
<223> OTHER INFORMATION: Synthetic
```

<400> SEQUENCE: 15

| Met | Gly | Trp | Ser | Cys | Ile | Ile | Leu | Phe | Leu | Val | Ala | Thr | Ala | Thr | Gly |
|---|---|---|---|---|---|---|---|---|---|---|---|---|---|---|---|
| 1 | | | | 5 | | | | | 10 | | | | | 15 | |

| Val | His | Ser | Glu | Val | Gln | Leu | Val | Glu | Thr | Gly | Gly | Gly | Leu | Val | Gln |
|---|---|---|---|---|---|---|---|---|---|---|---|---|---|---|---|
| | | | 20 | | | | | 25 | | | | | 30 | | |

| Pro | Gly | Asn | Ser | Leu | Lys | Leu | Ser | Cys | Ala | Thr | Ser | Gly | Phe | Ile | Phe |
|---|---|---|---|---|---|---|---|---|---|---|---|---|---|---|---|
| | | | 35 | | | | | 40 | | | | | 45 | | |

| Ser | Thr | Thr | Trp | Met | Asn | Trp | Ile | Arg | Gln | Thr | Pro | Gly | Lys | Arg | Leu |
|---|---|---|---|---|---|---|---|---|---|---|---|---|---|---|---|
| | 50 | | | | | 55 | | | | | 60 | | | | |

| Glu | Trp | Leu | Ala | Gln | Ile | Glu | Asp | Lys | Ser | Asn | Asn | Tyr | Phe | Ile | Ser |
|---|---|---|---|---|---|---|---|---|---|---|---|---|---|---|---|
| 65 | | | | | 70 | | | | | 75 | | | | | 80 |

| Tyr | Ser | Glu | Ser | Val | Lys | Gly | Arg | Phe | Thr | Ile | Ser | Arg | Asp | Asp | Ser |
|---|---|---|---|---|---|---|---|---|---|---|---|---|---|---|---|
| | | | | 85 | | | | | 90 | | | | | 95 | |

| Lys | Ser | Ser | Val | Tyr | Leu | Gln | Met | Asn | Asn | Leu | Lys | Glu | Glu | Asp | Thr |
|---|---|---|---|---|---|---|---|---|---|---|---|---|---|---|---|
| | | | 100 | | | | | 105 | | | | | 110 | | |

| Ala | Ile | Tyr | Tyr | Cys | Ser | Trp | Lys | Tyr | Arg | Ser | Asn | Tyr | Tyr | Phe | Asp |
|---|---|---|---|---|---|---|---|---|---|---|---|---|---|---|---|
| | | | 115 | | | | | 120 | | | | | 125 | | |

| Tyr | Trp | Gly | Gln | Gly | Val | Met | Val | Thr | Val | Ser | Ser | Gly | Ser | Thr | Ser |
|---|---|---|---|---|---|---|---|---|---|---|---|---|---|---|---|
| | 130 | | | | | 135 | | | | | 140 | | | | |

| Gly | Ser | Gly | Lys | Pro | Gly | Ser | Gly | Glu | Gly | Ser | Asp | Ile | Val | Leu | Thr |
|---|---|---|---|---|---|---|---|---|---|---|---|---|---|---|---|
| 145 | | | | | 150 | | | | | 155 | | | | | 160 |

| Gln | Ser | Pro | Ala | Leu | Ala | Val | Ser | Leu | Glu | Gln | Arg | Ala | Thr | Ile | Ser |
|---|---|---|---|---|---|---|---|---|---|---|---|---|---|---|---|
| | | | | 165 | | | | | 170 | | | | | 175 | |

| Cys | Lys | Thr | Ser | Gln | Asn | Val | Asp | Tyr | Tyr | Gly | Ile | Ser | Tyr | Leu | His |
|---|---|---|---|---|---|---|---|---|---|---|---|---|---|---|---|
| | | | 180 | | | | | 185 | | | | | 190 | | |

| Trp | Tyr | Gln | Gln | Lys | Pro | Gly | Gln | Gln | Pro | Lys | Leu | Leu | Ile | Tyr | Glu |
|---|---|---|---|---|---|---|---|---|---|---|---|---|---|---|---|
| | | | 195 | | | | | 200 | | | | | 205 | | |

| Gly | Ser | Asn | Leu | Ala | Ser | Gly | Ile | Pro | Ala | Arg | Phe | Ser | Gly | Ser | Gly |
|---|---|---|---|---|---|---|---|---|---|---|---|---|---|---|---|
| | 210 | | | | | 215 | | | | | 220 | | | | |

| Ser | Gly | Thr | Asp | Phe | Thr | Leu | Thr | Ile | Asp | Pro | Val | Glu | Ala | Asp | Asp |
|---|---|---|---|---|---|---|---|---|---|---|---|---|---|---|---|
| 225 | | | | | 230 | | | | | 235 | | | | | 240 |

| Ile | Val | Thr | Tyr | Tyr | Cys | Gln | Gln | Ser | Lys | Asp | Tyr | Pro | Tyr | Thr | Phe |
|---|---|---|---|---|---|---|---|---|---|---|---|---|---|---|---|
| | | | | 245 | | | | | 250 | | | | | 255 | |

| Gly | Ala | Gly | Thr | Lys | Leu | Glu | Leu | Lys | Ala | Ala | Ala | Ile | Glu | Val | Met |
|---|---|---|---|---|---|---|---|---|---|---|---|---|---|---|---|
| | | | 260 | | | | | 265 | | | | | 270 | | |

| Tyr | Pro | Pro | Pro | Tyr | Leu | Asp | Asn | Glu | Lys | Ser | Asn | Gly | Thr | Ile | Ile |
|---|---|---|---|---|---|---|---|---|---|---|---|---|---|---|---|
| | | | 275 | | | | | 280 | | | | | 285 | | |

| His | Val | Lys | Gly | Lys | His | Leu | Cys | Pro | Ser | Pro | Leu | Phe | Pro | Gly | Pro |
|---|---|---|---|---|---|---|---|---|---|---|---|---|---|---|---|
| | 290 | | | | | 295 | | | | | 300 | | | | |

| Ser | Lys | Pro | Phe | Trp | Val | Leu | Val | Val | Gly | Gly | Val | Leu | Ala | Cys |
|---|---|---|---|---|---|---|---|---|---|---|---|---|---|---|
| 305 | | | | | 310 | | | | | 315 | | | | 320 |

| Tyr | Ser | Leu | Leu | Val | Thr | Val | Ala | Phe | Ile | Ile | Phe | Trp | Val | Arg | Ser |
|---|---|---|---|---|---|---|---|---|---|---|---|---|---|---|---|
| | | | | 325 | | | | | 330 | | | | | 335 | |

| Lys | Arg | Ser | Arg | Leu | Leu | His | Ser | Asp | Tyr | Met | Asn | Met | Thr | Pro | Arg |
|---|---|---|---|---|---|---|---|---|---|---|---|---|---|---|---|
| | | | 340 | | | | | 345 | | | | | 350 | | |

| Arg | Pro | Gly | Pro | Thr | Arg | Lys | His | Tyr | Gln | Pro | Tyr | Ala | Pro | Pro | Arg |
|---|---|---|---|---|---|---|---|---|---|---|---|---|---|---|---|
| | | | 355 | | | | | 360 | | | | | 365 | | |

| Asp | Phe | Ala | Ala | Tyr | Arg | Ser | Arg | Val | Lys | Phe | Ser | Arg | Ser | Ala | Asp |
|---|---|---|---|---|---|---|---|---|---|---|---|---|---|---|---|
| | | | 370 | | | | | 375 | | | | | 380 | | |

| Ala | Pro | Ala | Tyr | Gln | Gln | Gly | Gln | Asn | Gln | Leu | Tyr | Asn | Glu | Leu | Asn |
|---|---|---|---|---|---|---|---|---|---|---|---|---|---|---|---|
| 385 | | | | | 390 | | | | | 395 | | | | | 400 |

| Leu | Gly | Arg | Arg | Glu | Glu | Tyr | Asp | Val | Leu | Asp | Lys | Arg | Arg | Gly | Arg |
|---|---|---|---|---|---|---|---|---|---|---|---|---|---|---|---|

```
                    405                 410                 415
Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 16
<211> LENGTH: 1641
<212> TYPE: DNA
<213> ORGANISM: Artificial Sequence
<220> FEATURE:
<223> OTHER INFORMATION: Synthetic

<400> SEQUENCE: 16
atggacttcc aggtgcagat cttctctttc ctgctgatta gtgcctccgt catcatgtcc    60
agaggcgata tccagatgac acagtccccc agttcagtgt ccgcgtccat cggggaccgt   120
gtcaccatta cctgtcgcgc cagtcaaggc atcgacaact ggctgggggtg gtaccagcaa   180 aagccaggga aggcgccaaa actgctgatc tatgatgcga gcaacctcga cactggagtc   240
cccagtaggt tctccggatc ggggtccggc acgtacttca ccttgaccat ctccagcctc   300
caggccgagg atttcgctgt ttacttctgc agcaggcaa aagcgtttcc gcccaccttc   360
ggcgggggca ccaaggtgga cataaaaggc agtaccagcg atccggcaa gccgggctct   420 ggcgaaggtt ccgaagtcca gttggtgcag tccggtggtg gcctggtcaa gccgggtggg   480
agtctcaggc tctcctgcgc cgcttcaggg ttcacattct cttcgtattc catgaactgg   540
gtgcgccagg cgccaggcaa ggggctggag tgggtcagtt cgatttcaag ttcgtcctcc   600
tacatctatt acgccgactc agtcaagggc cgcttcacaa tctccagaga caacgctaag   660
aactcgctgt acctccaaat gaactcgctg cgcgccgaag acaccgccgt gtactattgc   720
gcgagagtga ctgatgcctt cgacatatgg ggcagggaa cgatggtgac cgtgagtagt   780
gcggccgcat tcgtgccggt cttcctgcca gcgaagccca ccacgacgcc agcgccgcga   840
ccaccaacac cggcgcccac catcgcgtcg cagcccctgt ccctgcgccc agaggcgtgc   900
cggccagcgc ggggggcgc agtgcacacg agggggctgg acttcgcctg tgatatctac   960
atctgggcgc ccttggccgg acttgtgggg gtccttctcc tgtcactggt tatcaccctt  1020
tactgcaacc acaggaacag gagtaagagg agcaggctcc tgcacagtga ctacatgaac  1080
atgactcccc gccgccccgg gcccacccgc aagcattacc agccctatgc cccaccacgc  1140
gacttcgcag cctatcgctc ccgtttctct gttgttaaac ggggcagaaa gaaactcctg  1200
tatatattca acaaccatt tatgagacca gtacaaacta ctcaagagga gatggctgt   1260 agctgccgat ttccagaaga agaagaagga ggatgtgaac tgagagtgaa gttcagcagg  1320
agcgcagacg ccccccgcgta ccagcagggc cagaaccagc tctataacga gctcaatcta  1380
ggacgaagag aggagtacga tgttttggac aagagacgtg gccgggaccc tgagatgggg  1440
ggaaagccga aggaagaa ccctcaggaa ggcctgtaca atgaactgca gaaagataag  1500
atggcggagg cctacagtga gattgggatg aaaggcgagc gccggagggg caaggggcac  1560
```

```
gatggccttt accagggtct cagtacagcc accaaggaca cctacgacgc ccttcacatg    1620
caggccctgc cccctcgcta a                                              1641

<210> SEQ ID NO 17
<211> LENGTH: 1444
<212> TYPE: DNA
<213> ORGANISM: Artificial Sequence
<220> FEATURE:
<223> OTHER INFORMATION: Synthetic

<400> SEQUENCE: 17
atggacttcc aggtgcagat cttctctttc ctgctgatta gtgcctccgt catcatgtcc      60
agaggcgata tccagatgac acagtccccc agttcagtgt ccgcgtccat cggggaccgt     120
gtcaccatta cctgtcgcgc cagtcaaggc atcgacaact ggctggggtg gtaccagcaa     180
aagccaggga aggcgccaaa actgctgatc tatgatgcga gcaacctcga cactggagtc     240
cccagtaggt tctccggatc ggggtccggc acgtacttca ccttgaccat ctccagcctc     300
caggccgagg atttcgctgt ttacttctgc agcaggcaa aagcgtttcc gcccaccttc      360
ggcgggggca ccaaggtgga cataaaaggc agtaccagcg gatccggcaa gccgggctct     420
ggcgaaggtt ccgaagtcca gttggtgcag tccgtggtg gcctggtcaa gccgggtggg      480
agtctcaggc tctcctgcgc cgcttcaggg ttcacattct cttcgtattc catgaactgg     540
gtgcgccagg cgccagcaa ggggctggag tgggtcagtt cgatttcaag ttcgtcctcc      600
tacatctatt acgccgactc agtcaagggc cgcttcacaa tctccagaga caacgctaag     660
aactcgctgt acctccaaat gaactcgctg cgcgccgaag acaccgccgt gtactattgc     720
gcgagagtga ctgatgcctt cgacatatgg ggccagggaa cgatggtgac cgtgagtagt     780
gcggccgcaa ttgaagttat gtatcctcct ccttacctag acaatgagaa gagcaatgga     840
accattatcc atgtgaaagg gaaacacctt tgtccaagtc cctatttcc ggaccttct       900 aagccctttt gggtgctggt ggtggttggt ggagtcctgg cttgctatag cttgctagta     960
acagtggcct ttattatttt ctgaggagta agaggagcag gctcctgcac agtgactaca    1020
tgaacatgac tccccgccgc cccgggccca ccgcaagca ttaccagccc tatgccccac     1080
cacgcgactt cgcagcctat cgctccagag tgaagttcag caggagcgca gacgcccccg    1140
cgtaccagca gggccagaac cagctctata cgagctcat ctaggacgaa gagaggagta     1200
cgatgttttg acaagagac gtggccggga ccctgagatg ggggaaagc cgagaaggaa      1260 gaaccctcag gaaggcctgt acaatgaact gcagaaagat aagatggcgg aggcctacag    1320
tgagattggg atgaaaggcg agcgccggag gggcaagggg cacgatggcc tttaccaggg    1380
tctcagtaca gccaccaagg acacctacga cgcccttcac atgcaggccc tgcccctcg    1440 ctaa                                                                 1444

<210> SEQ ID NO 18
<211> LENGTH: 1620
<212> TYPE: DNA
<213> ORGANISM: Artificial Sequence
<220> FEATURE:
<223> OTHER INFORMATION: Synthetic

<400> SEQUENCE: 18
atgggatggt catgtatcat ccttttttctg gtagcaactg caactggagt acattcagag     60
gtgcagctgg tggagacagg aggaggcttg gtacagcctg gaaattccct aaagctttcc    120
tgtgccacct caggattcat tttcagtaca acttggatga actggatccg ccagactcca    180
```

```
gggaaaagac tggagtggct tgctcaaatt gaagacaaat ctaataatta ttttatatca      240
tattcggagt ctgtgaaagg aagattcacc atttcaagag atgattccaa aagcagcgtt      300
tacctgcaga tgaacaactt aaaagaggag acactgcca tttattactg tagttggaaa       360
tataggtcca actattactt tgattactgg ggccaaggag tcatggtcac agtctcctca      420
gggtctacat ctggatctgg gaagccgggt tctggtgagg gttctgacat tgtgctgacc      480
cagtctcctg ctttggctgt gtctctagag cagagagcca ccatctcttg caaaaccagc      540
cagaatgtcg attattatgg cattagttat ttgcactggt accaacagaa accaggacag      600
caacccaaac tcctcatcta tgaagggtcc aacttagcat ctgggatccc tgccaggttc      660
agtggcagtg ggtctgggac agacttcacc ctcaccatcg atcctgtgga ggctgatgat      720
attgtaacct attactgtca gcagagtaag gattatccgt acacgtttgg agctgggacc      780
aagctggaac tgaaagcggc cgcaactact accaagccag tgctgcgaac tccctcacct      840
gtgcacccta ccgggacatc tcagcccag agaccagaag attgtcggcc ccgtggctca       900
gtgaagggga ccggattgga cttcgcctgt gatatttaca tctgggcacc cttggccgga      960
atctgcgtgg cccttctgct gtccttgatc atcactctca tctgctacca caggagccga     1020
aatagtagaa ggaacagact ccttcaagtg actaccatga acatgactcc ccggaggcct     1080
gggctcactc gaaagcctta ccagcccta cgcccctgcca gagactttgc agcgtaccgc     1140
cccaaatgga tcaggaaaaa attcccccac atattcaagc aaccatttaa gaagaccact     1200
ggagcagctc aagaggaaga tgcttgtagc tgccgatgtc cacaggaaga agaaggagga     1260
ggaggaggct atgagctgag agcaaaattc agcaggagtg cagagactgc tgccaacctg     1320
caggacccca accagctcta caatgagctc aatctagggc gaagagagga atatgacgtc     1380
ttggagaaga gcgggctcg cgatccagag atgggaggca acagcagag gaggaggaac       1440 ccccaggaag gcgtatacaa tgcactgcag aaagacaaga tggcagaagc ctacagtgag     1500
atcggcacaa aaggcgagag gcggagaggc aaggggcacg atggcctta ccagggtctc      1560 agcactgcca ccaaggacac ctatgatgcc ctgcatatgc agaccctggc ccctcgctaa     1620
```

<210> SEQ ID NO 19
<211> LENGTH: 1485
<212> TYPE: DNA
<213> ORGANISM: Artificial Sequence
<220> FEATURE:
<223> OTHER INFORMATION: Synthetic

<400> SEQUENCE: 19

```
atgggatggt catgtatcat cctttttctg gtagcaactg caactggagt acattcagag       60
gtgcagctgg tggagacagg aggaggcttg gtacagcctg gaaattccct aaagcttcc      120 tgtgccacct caggattcat tttcagtaca acttggatga actggatccg ccagactcca      180
gggaaaagac tggagtggct tgctcaaatt gaagacaaat ctaataatta ttttatatca      240
tattcggagt ctgtgaaagg aagattcacc atttcaagag atgattccaa aagcagcgtt      300
tacctgcaga tgaacaactt aaaagaggag acactgcca tttattactg tagttggaaa       360
tataggtcca actattactt tgattactgg ggccaaggag tcatggtcac agtctcctca      420
gggtctacat ctggatctgg gaagccgggt tctggtgagg gttctgacat tgtgctgacc      480
cagtctcctg ctttggctgt gtctctagag cagagagcca ccatctcttg caaaaccagc      540
cagaatgtcg attattatgg cattagttat ttgcactggt accaacagaa accaggacag      600
```

```
caacccaaac tcctcatcta tgaagggtcc aacttagcat ctgggatccc tgccaggttc    660
agtggcagtg ggtctgggac agacttcacc ctcaccatcg atcctgtgga ggctgatgat    720
attgtaacct attactgtca gcagagtaag gattatccgt acacgtttgg agctgggacc    780
aagctggaac tgaaagcggc cgcaactact accaagccag tgctgcgaac tccctcacct    840
gtgcacccta ccgggacatc tcagccccag agaccagaag attgtcggcc ccgtggctca    900
gtgaagggga ccggattgga cttcgcctgt gatatttaca tctgggcacc cttggccgga    960
atctgcgtgg cccttctgct gtccttgatc atcactctca tctgctacca caggagccga   1020
aatagtagaa ggaacagact ccttcaagtg actaccatga acatgactcc ccggaggcct   1080
gggctcactc gaaagcctta ccagccctac gcccctgcca gagactttgc agcgtaccgc   1140
cccagagcaa aattcagcag gagtgcagag actgctgcca acctgcagga ccccaaccag   1200
ctctacaatg agctcaatct agggcgaaga gaggaatatg acgtcttgga gaagaagcgg   1260
gctcgcgatc cagagatggg aggcaaacag cagaggagga ggaaccccca ggaaggcgta   1320
tacaatgcac tgcagaaaga caagatggca gaagcctaca gtgagatcgg cacaaaaggc   1380
gagaggcgga gaggcaaggg gcacgatggc ctttaccagg gtctcagcac tgccaccaag   1440
gacacctatg atgccctgca tatgcagacc ctggcccctc gctaa                    1485

<210> SEQ ID NO 20
<211> LENGTH: 1656
<212> TYPE: DNA
<213> ORGANISM: Artificial Sequence
<220> FEATURE:
<223> OTHER INFORMATION: Synthetic

<400> SEQUENCE: 20
atgggatggt catgtatcat cctttttctg gtagcaactg caactggagt acattcagag     60
gtgcagctgg tggagacagg aggaggcttg gtacagcctg gaaattccct aaagctttcc    120
tgtgccacct caggattcat tttcagtaca acttggatga actggatccg ccagactcca    180
gggaaaagac tggagtggct tgctcaaatt gaagacaaat ctaataatta tttttatatca    240 tattcggagt ctgtgaaagg aagattcacc atttcaagag atgattccaa agcagcgtt    300 tacctgcaga tgaacaactt aaaagaggag gacactgcca tttattactg tagttggaaa    360
tataggtcca actattactt tgattactgg ggccaaggag tcatggtcac agtctcctca    420
gggtctacat ctggatctgg gaagccgggt tctggtgagg ttctgacat tgtgctgacc    480 cagtctcctg ctttggctgt gtctctagag cagagagcca ccatctcttg caaaaccagc    540
cagaatgtcg attattatgg cattagttat ttgcactggt accaacagaa accaggacag    600
caacccaaac tcctcatcta tgaagggtcc aacttagcat ctgggatccc tgccaggttc    660
agtggcagtg ggtctgggac agacttcacc ctcaccatcg atcctgtgga ggctgatgat    720
attgtaacct attactgtca gcagagtaag gattatccgt acacgtttgg agctgggacc    780
aagctggaac tgaaagcggc cgcattcgtg ccggtcttcc tgccagcgaa gcccaccacg    840
acgccagcgc cgcgaccacc aacaccggcg cccaccatcg cgtcgcagcc cctgtccctg    900
cgcccagagg cgtgccggcc agcggcgggg ggcgcagtgc acacgagggg gctggacttc    960
gcctgtgata tctacatctg ggcgcccttg gccgggactt gtgggtcct tctcctgtca   1020 ctggttatca cccttttactg caaccacagg aacaggagta agaggagcag gctcctgcac   1080
agtgactaca tgaacatgac tccccgccgc cccgggccca cccgcaagca ttaccagccc   1140
tatgccccac cacgcgactt cgcagcctat cgctcccgtt tctctgttgt taaacggggc   1200
```

| | |
|---|---|
| agaaagaaac tcctgtatat attcaaacaa ccatttatga gaccagtaca aactactcaa | 1260 |
| gaggaagatg gctgtagctg ccgatttcca gaagaagaag aaggaggatg tgaactgaga | 1320 |
| gtgaagttca gcaggagcgc agacgccccc gcgtaccagc agggccagaa ccagctctat | 1380 |
| aacgagctca atctaggacg aagagaggag tacgatgttt tggacaagag acgtggccgg | 1440 |
| gaccctgaga tgggggggaaa gccgagaagg aagaaccctc aggaaggcct gtacaatgaa | 1500 |
| ctgcagaaag ataagatggc ggaggcctac agtgagattg ggatgaaagg cgagcgccgg | 1560 |
| aggggcaagg ggcacgatgg cctttaccag ggtctcagta cagccaccaa ggacacctac | 1620 |
| gacgcccttc acatgcaggc cctgccccct cgctaa | 1656 |

<210> SEQ ID NO 21
<211> LENGTH: 1464
<212> TYPE: DNA
<213> ORGANISM: Artificial Sequence
<220> FEATURE:
<223> OTHER INFORMATION: Synthetic

<400> SEQUENCE: 21

| | |
|---|---|
| atgggatggt catgtatcat ccttttttctg gtagcaactg caactggagt acattcagag | 60 |
| gtgcagctgg tggagacagg aggaggcttg gtacagcctg gaaattccct aaagctttcc | 120 |
| tgtgccacct caggattcat tttcagtaca acttggatga actggatccg ccagactcca | 180 |
| gggaaaagac tggagtggct tgctcaaatt gaagacaaat ctaataatta ttttatatca | 240 |
| tattcggagt ctgtgaaagg aagattcacc atttcaagag atgattccaa agcagcgtt | 300 |
| tacctgcaga tgaacaactt aaaagaggag gacactgcca tttattactg tagttggaaa | 360 |
| tataggtcca actattactt tgattactgg ggccaaggag tcatggtcac agtctcctca | 420 |
| gggtctacat ctggatctgg gaagccgggt tctggtgagg gttctgacat tgtgctgacc | 480 |
| cagtctcctg ctttggctgt gtctctagag cagagagcca ccatctcttg caaaaccagc | 540 |
| cagaatgtcg attattatgg cattagttat ttgcactggt accaacagaa accaggacag | 600 |
| caacccaaac tcctcatcta tgaagggtcc aacttagcat ctgggatccc tgccaggttc | 660 |
| agtggcagtg ggtctgggac agacttcacc ctcaccatcg atcctgtgga ggctgatgat | 720 |
| attgtaacct attactgtca gcagagtaag gattatccgt acacgtttgg agctgggacc | 780 |
| aagctggaac tgaaagcggc cgcaattgaa gttatgtatc ctcctcctta cctagacaat | 840 |
| gagaagagca atggaaccat tatccatgtg aaagggaaac ctttgtcc aagtccccta | 900 |
| tttcccggac cttctaagcc cttttgggtg ctggtggtgg ttggtggagt cctggcttgc | 960 |
| tatagcttgc tagtaacagt ggcctttatt attttctggg tgaggagtaa gaggagcagg | 1020 |
| ctcctgcaca gtgactacat gaacatgact ccccgccgcc ccgggcccac cgcaagcat | 1080 |
| taccagccct atgccccacc acgcgacttc gcagcctatc gctccagagt gaagttcagc | 1140 |
| aggagcgcag acgccccgc gtaccagcag ggccagaacc agctctataa cgagctcaat | 1200 |
| ctaggacgaa gagaggagta cgatgttttg gacaagagac gtggccggga ccctgagatg | 1260 |
| gggggaaagc cgagaaggaa gaaccctcag gaaggcctgt acaatgaact gcagaaagat | 1320 |
| aagatggcgg aggcctacag tgagattggg atgaaaggcg agcgccggag gggcaagggg | 1380 |
| cacgatggcc tttaccaggg tctcagtaca gccaccaagg acacctacga cgcccttcac | 1440 |
| atgcaggccc tgccccctcg ctaa | 1464 |

<210> SEQ ID NO 22

<211> LENGTH: 31
<212> TYPE: DNA
<213> ORGANISM: Artificial Sequence
<220> FEATURE:
<223> OTHER INFORMATION: Synthetic

<400> SEQUENCE: 22
tcgctcgagg ccgccaccat gggatggtca t                              31

<210> SEQ ID NO 23
<211> LENGTH: 35
<212> TYPE: DNA
<213> ORGANISM: Artificial Sequence
<220> FEATURE:
<223> OTHER INFORMATION: Synthetic

<400> SEQUENCE: 23
tcggcggccg ctttcagttc cagcttggtc ccagc                          35

<210> SEQ ID NO 24
<211> LENGTH: 53
<212> TYPE: DNA
<213> ORGANISM: Artificial Sequence
<220> FEATURE:
<223> OTHER INFORMATION: Synthetic

<400> SEQUENCE: 24
ctgggaagcc gggttctggt gagggttctg acattgtgct gacccagtct cct      53

<210> SEQ ID NO 25
<211> LENGTH: 60
<212> TYPE: DNA
<213> ORGANISM: Artificial Sequence
<220> FEATURE:
<223> OTHER INFORMATION: Synthetic

<400> SEQUENCE: 25
accagaaccc ggcttcccag atccagatgt agaccctgag gagactgtga ccatgactcc   60

<210> SEQ ID NO 26
<211> LENGTH: 35
<212> TYPE: DNA
<213> ORGANISM: Artificial Sequence
<220> FEATURE:
<223> OTHER INFORMATION: Synthetic

<400> SEQUENCE: 26
acggtcgact tatcggctcc tgtggtagca gatga                          35

<210> SEQ ID NO 27
<211> LENGTH: 33
<212> TYPE: DNA
<213> ORGANISM: Artificial Sequence
<220> FEATURE:
<223> OTHER INFORMATION: Synthetic

<400> SEQUENCE: 27
tcgctcgagc tctagaccgc catggatttt cag                            33

<210> SEQ ID NO 28
<211> LENGTH: 33
<212> TYPE: DNA
<213> ORGANISM: Artificial Sequence
<220> FEATURE:
<223> OTHER INFORMATION: Synthetic

<400> SEQUENCE: 28

```
tcggcggccg cggtgaccgt agttccttgg ccc                               33
```

<210> SEQ ID NO 29
<211> LENGTH: 19
<212> TYPE: DNA
<213> ORGANISM: Artificial Sequence
<220> FEATURE:
<223> OTHER INFORMATION: Synthetic

<400> SEQUENCE: 29

```
gtggggtcc tcgaggcca                                                19
```

<210> SEQ ID NO 30
<211> LENGTH: 38
<212> TYPE: DNA
<213> ORGANISM: Artificial Sequence
<220> FEATURE:
<223> OTHER INFORMATION: Synthetic

<400> SEQUENCE: 30

```
ccatggactt ccaggtgcag atcttctctt tcctgctg                          38
```

<210> SEQ ID NO 31
<211> LENGTH: 38
<212> TYPE: DNA
<213> ORGANISM: Artificial Sequence
<220> FEATURE:
<223> OTHER INFORMATION: Synthetic

<400> SEQUENCE: 31

```
attagtgcct ccgtcatcat gtccagaggc gatatcca                          38
```

<210> SEQ ID NO 32
<211> LENGTH: 38
<212> TYPE: DNA
<213> ORGANISM: Artificial Sequence
<220> FEATURE:
<223> OTHER INFORMATION: Synthetic

<400> SEQUENCE: 32

```
gatgacacag tcccccagtt cagtgtccgc gtccatcg                          38
```

<210> SEQ ID NO 33
<211> LENGTH: 38
<212> TYPE: DNA
<213> ORGANISM: Artificial Sequence
<220> FEATURE:
<223> OTHER INFORMATION: Synthetic

<400> SEQUENCE: 33

```
gggaccgtgt caccattacc tgtcgcgcca gtcaaggc                          38
```

<210> SEQ ID NO 34
<211> LENGTH: 38
<212> TYPE: DNA
<213> ORGANISM: Artificial Sequence
<220> FEATURE:
<223> OTHER INFORMATION: Synthetic

<400> SEQUENCE: 34

```
atcgacaact ggctggggtg gtaccagcaa aagccagg                          38
```

<210> SEQ ID NO 35
<211> LENGTH: 38
<212> TYPE: DNA

```
<213> ORGANISM: Artificial Sequence
<220> FEATURE:
<223> OTHER INFORMATION: Synthetic

<400> SEQUENCE: 35
gaaggcgcca aaactgctga tctatgatgc gagcaacc                              38

<210> SEQ ID NO 36
<211> LENGTH: 38
<212> TYPE: DNA
<213> ORGANISM: Artificial Sequence
<220> FEATURE:
<223> OTHER INFORMATION: Synthetic

<400> SEQUENCE: 36
tcgacactgg agtccccagt aggttctccg gatcgggg                              38

<210> SEQ ID NO 37
<211> LENGTH: 38
<212> TYPE: DNA
<213> ORGANISM: Artificial Sequence
<220> FEATURE:
<223> OTHER INFORMATION: Synthetic

<400> SEQUENCE: 37
tccggcacgt acttcacctt gaccatctcc agcctcca                              38

<210> SEQ ID NO 38
<211> LENGTH: 38
<212> TYPE: DNA
<213> ORGANISM: Artificial Sequence
<220> FEATURE:
<223> OTHER INFORMATION: Synthetic

<400> SEQUENCE: 38
ggccgaggat ttcgctgttt acttctgcca gcaggcaa                              38

<210> SEQ ID NO 39
<211> LENGTH: 38
<212> TYPE: DNA
<213> ORGANISM: Artificial Sequence
<220> FEATURE:
<223> OTHER INFORMATION: Synthetic

<400> SEQUENCE: 39
aagcgtttcc gcccaccttc ggcggggca ccaaggtg                               38

<210> SEQ ID NO 40
<211> LENGTH: 38
<212> TYPE: DNA
<213> ORGANISM: Artificial Sequence
<220> FEATURE:
<223> OTHER INFORMATION: Synthetic

<400> SEQUENCE: 40
gacataaaag gcagtaccag cggatccggc aagccggg                              38

<210> SEQ ID NO 41
<211> LENGTH: 38
<212> TYPE: DNA
<213> ORGANISM: Artificial Sequence
<220> FEATURE:
<223> OTHER INFORMATION: Synthetic

<400> SEQUENCE: 41
ctctggcgaa ggttccgaag tccagttggt gcagtccg                              38
```

<210> SEQ ID NO 42
<211> LENGTH: 38
<212> TYPE: DNA
<213> ORGANISM: Artificial Sequence
<220> FEATURE:
<223> OTHER INFORMATION: Synthetic

<400> SEQUENCE: 42
gtggtggcct ggtcaagccg ggtgggagtc tcaggctc                    38

<210> SEQ ID NO 43
<211> LENGTH: 38
<212> TYPE: DNA
<213> ORGANISM: Artificial Sequence
<220> FEATURE:
<223> OTHER INFORMATION: Synthetic

<400> SEQUENCE: 43
tcctgcgccg cttcagggtt cacattctct tcgtattc                    38

<210> SEQ ID NO 44
<211> LENGTH: 38
<212> TYPE: DNA
<213> ORGANISM: Artificial Sequence
<220> FEATURE:
<223> OTHER INFORMATION: Synthetic

<400> SEQUENCE: 44
catgaactgg gtgcgccagg cgccaggcaa ggggctgg                    38

<210> SEQ ID NO 45
<211> LENGTH: 38
<212> TYPE: DNA
<213> ORGANISM: Artificial Sequence
<220> FEATURE:
<223> OTHER INFORMATION: Synthetic

<400> SEQUENCE: 45
agtgggtcag ttcgatttca agttcgtcct cctacatc                    38

<210> SEQ ID NO 46
<211> LENGTH: 38
<212> TYPE: DNA
<213> ORGANISM: Artificial Sequence
<220> FEATURE:
<223> OTHER INFORMATION: Synthetic

<400> SEQUENCE: 46
tattacgccg actcagtcaa gggccgcttc acaatctc                    38

<210> SEQ ID NO 47
<211> LENGTH: 38
<212> TYPE: DNA
<213> ORGANISM: Artificial Sequence
<220> FEATURE:
<223> OTHER INFORMATION: Synthetic

<400> SEQUENCE: 47
cagagacaac gctaagaact cgctgtacct ccaaatga                    38

<210> SEQ ID NO 48
<211> LENGTH: 38
<212> TYPE: DNA
<213> ORGANISM: Artificial Sequence
<220> FEATURE:

<223> OTHER INFORMATION: Synthetic

<400> SEQUENCE: 48
actcgctgcg cgccgaagac accgccgtgt actattgc                                    38

<210> SEQ ID NO 49
<211> LENGTH: 38
<212> TYPE: DNA
<213> ORGANISM: Artificial Sequence
<220> FEATURE:
<223> OTHER INFORMATION: Synthetic

<400> SEQUENCE: 49
gcgagagtga ctgatgcctt cgacatatgg ggccaggg                                    38

<210> SEQ ID NO 50
<211> LENGTH: 38
<212> TYPE: DNA
<213> ORGANISM: Artificial Sequence
<220> FEATURE:
<223> OTHER INFORMATION: Synthetic

<400> SEQUENCE: 50
aacgatggtg accgtgagta gtgcggccgc aagagatc                                    38

<210> SEQ ID NO 51
<211> LENGTH: 19
<212> TYPE: DNA
<213> ORGANISM: Artificial Sequence
<220> FEATURE:
<223> OTHER INFORMATION: Synthetic

<400> SEQUENCE: 51
gatctcttgc ggccgcact                                                         19

<210> SEQ ID NO 52
<211> LENGTH: 38
<212> TYPE: DNA
<213> ORGANISM: Artificial Sequence
<220> FEATURE:
<223> OTHER INFORMATION: Synthetic

<400> SEQUENCE: 52
actcacggtc accatcgttc cctggcccca tatgtcga                                    38

<210> SEQ ID NO 53
<211> LENGTH: 38
<212> TYPE: DNA
<213> ORGANISM: Artificial Sequence
<220> FEATURE:
<223> OTHER INFORMATION: Synthetic

<400> SEQUENCE: 53
aggcatcagt cactctcgcg caatagtaca cggcggtg                                    38

<210> SEQ ID NO 54
<211> LENGTH: 38
<212> TYPE: DNA
<213> ORGANISM: Artificial Sequence
<220> FEATURE:
<223> OTHER INFORMATION: Synthetic

<400> SEQUENCE: 54
tcttcggcgc gcagcgagtt catttggagg tacagcga                                    38

<210> SEQ ID NO 55
<211> LENGTH: 38
<212> TYPE: DNA
<213> ORGANISM: Artificial Sequence
<220> FEATURE:
<223> OTHER INFORMATION: Synthetic

<400> SEQUENCE: 55
gttcttagcg ttgtctctgg agattgtgaa gcggccct					38

<210> SEQ ID NO 56
<211> LENGTH: 38
<212> TYPE: DNA
<213> ORGANISM: Artificial Sequence
<220> FEATURE:
<223> OTHER INFORMATION: Synthetic

<400> SEQUENCE: 56
tgactgagtc ggcgtaatag atgtaggagg acgaactt					38

<210> SEQ ID NO 57
<211> LENGTH: 38
<212> TYPE: DNA
<213> ORGANISM: Artificial Sequence
<220> FEATURE:
<223> OTHER INFORMATION: Synthetic

<400> SEQUENCE: 57
gaaatcgaac tgacccactc cagccccttg cctggcgc					38

<210> SEQ ID NO 58
<211> LENGTH: 38
<212> TYPE: DNA
<213> ORGANISM: Artificial Sequence
<220> FEATURE:
<223> OTHER INFORMATION: Synthetic

<400> SEQUENCE: 58
ctggcgcacc cagttcatgg aatacgaaga gaatgtga					38

<210> SEQ ID NO 59
<211> LENGTH: 38
<212> TYPE: DNA
<213> ORGANISM: Artificial Sequence
<220> FEATURE:
<223> OTHER INFORMATION: Synthetic

<400> SEQUENCE: 59
accctgaagc ggcgcaggag agcctgagac tcccaccc					38

<210> SEQ ID NO 60
<211> LENGTH: 38
<212> TYPE: DNA
<213> ORGANISM: Artificial Sequence
<220> FEATURE:
<223> OTHER INFORMATION: Synthetic

<400> SEQUENCE: 60
ggcttgacca ggccaccacc ggactgcacc aactggac					38

<210> SEQ ID NO 61
<211> LENGTH: 38
<212> TYPE: DNA
<213> ORGANISM: Artificial Sequence
<220> FEATURE:
<223> OTHER INFORMATION: Synthetic

<400> SEQUENCE: 61
ttcggaacct tcgccagagc ccggcttgcc ggatccgc                                38

<210> SEQ ID NO 62
<211> LENGTH: 38
<212> TYPE: DNA
<213> ORGANISM: Artificial Sequence
<220> FEATURE:
<223> OTHER INFORMATION: Synthetic

<400> SEQUENCE: 62
tggtactgcc ttttatgtcc accttggtgc ccccgccg                                38

<210> SEQ ID NO 63
<211> LENGTH: 38
<212> TYPE: DNA
<213> ORGANISM: Artificial Sequence
<220> FEATURE:
<223> OTHER INFORMATION: Synthetic

<400> SEQUENCE: 63
aaggtgggcg gaaacgcttt tgcctgctgg cagaagta                                38

<210> SEQ ID NO 64
<211> LENGTH: 38
<212> TYPE: DNA
<213> ORGANISM: Artificial Sequence
<220> FEATURE:
<223> OTHER INFORMATION: Synthetic

<400> SEQUENCE: 64
aacagcgaaa tcctcggcct ggaggctgga gatggtca                                38

<210> SEQ ID NO 65
<211> LENGTH: 38
<212> TYPE: DNA
<213> ORGANISM: Artificial Sequence
<220> FEATURE:
<223> OTHER INFORMATION: Synthetic

<400> SEQUENCE: 65
aggtgaagta cgtgccggac cccgatccgg agaaccta                                38

<210> SEQ ID NO 66
<211> LENGTH: 38
<212> TYPE: DNA
<213> ORGANISM: Artificial Sequence
<220> FEATURE:
<223> OTHER INFORMATION: Synthetic

<400> SEQUENCE: 66
ctggggactc cagtgtcgag gttgctcgca tcatagat                                38

<210> SEQ ID NO 67
<211> LENGTH: 38
<212> TYPE: DNA
<213> ORGANISM: Artificial Sequence
<220> FEATURE:
<223> OTHER INFORMATION: Synthetic

<400> SEQUENCE: 67
cagcagtttt ggcgccttcc ctggcttttg ctggtacc                                38

<210> SEQ ID NO 68
<211> LENGTH: 38

```
<212> TYPE: DNA
<213> ORGANISM: Artificial Sequence
<220> FEATURE:
<223> OTHER INFORMATION: Synthetic

<400> SEQUENCE: 68
accccagcca gttgtcgatg ccttgactgg cgcgacag                              38

<210> SEQ ID NO 69
<211> LENGTH: 38
<212> TYPE: DNA
<213> ORGANISM: Artificial Sequence
<220> FEATURE:
<223> OTHER INFORMATION: Synthetic

<400> SEQUENCE: 69
gtaatggtga cacggtcccc gatggacgcg gacactga                              38

<210> SEQ ID NO 70
<211> LENGTH: 38
<212> TYPE: DNA
<213> ORGANISM: Artificial Sequence
<220> FEATURE:
<223> OTHER INFORMATION: Synthetic

<400> SEQUENCE: 70
actgggggac tgtgtcatct ggatatcgcc tctggaca                              38

<210> SEQ ID NO 71
<211> LENGTH: 38
<212> TYPE: DNA
<213> ORGANISM: Artificial Sequence
<220> FEATURE:
<223> OTHER INFORMATION: Synthetic

<400> SEQUENCE: 71
tgatgacgga ggcactaatc agcaggaaag agaagatc                              38

<210> SEQ ID NO 72
<211> LENGTH: 38
<212> TYPE: DNA
<213> ORGANISM: Artificial Sequence
<220> FEATURE:
<223> OTHER INFORMATION: Synthetic

<400> SEQUENCE: 72
tgcacctgga agtccatggt ggcctcgagg accccac                               38
```